(12) United States Patent
Rabkin et al.

(10) Patent No.: US 6,676,692 B2
(45) Date of Patent: Jan. 13, 2004

(54) APPARATUS FOR DELIVERING, REPOSITIONING AND/OR RETRIEVING SELF-EXPANDING STENTS

(75) Inventors: Dmitry Rabkin, Chestnut Hill, MA (US); Eyal Morag, East Hampton, MA (US); Ophir Perelson, Beverly Hills, CA (US)

(73) Assignee: InTek Technology L.L.C., Wilmington, DE (US)

( * ) Notice: Subject to any disclaimer, the term of this patent is extended or adjusted under 35 U.S.C. 154(b) by 0 days.

(21) Appl. No.: 09/845,098

(22) Filed: Apr. 27, 2001

(65) Prior Publication Data

US 2002/0161377 A1 Oct. 31, 2002

(51) Int. Cl.⁷ .......................... A61F 2/06; A61M 29/00
(52) U.S. Cl. ........................ 623/1.11; 606/191; 604/104
(58) Field of Search .................... 623/1.11; 606/198, 606/195, 194, 192, 108; 604/93.01, 96.01, 97.01, 103.08, 113, 104

(56) References Cited

U.S. PATENT DOCUMENTS

| | | | | | |
|---|---|---|---|---|---|
| 5,002,556 A | * | 3/1991 | Ishida et al. | ................ | 606/191 |
| 5,569,295 A | * | 10/1996 | Lam | ........................... | 606/198 |
| 5,616,149 A | * | 4/1997 | Barath | ........................ | 606/159 |
| 5,776,141 A | * | 7/1998 | Klein et al. | .................. | 606/108 |
| 5,902,268 A | * | 5/1999 | Saab | ........................... | 604/96 |
| 5,910,144 A | * | 6/1999 | Hayashi | ..................... | 606/108 |
| 6,217,585 B1 | * | 4/2001 | Houser et al. | .............. | 606/108 |
| 6,319,251 B1 | * | 11/2001 | Tu et al. | ...................... | 606/41 |

FOREIGN PATENT DOCUMENTS

EP          0778010          6/1997

* cited by examiner

*Primary Examiner*—Corrine McDermott
*Assistant Examiner*—Alvin Stewart
(74) *Attorney, Agent, or Firm*—Steinberg & Raskin, P.C.

(57) ABSTRACT

Apparatus for delivering and deploying a stent formed of a shape memory alloy to a desired position in a tubular area of the body, and/or for repositioning and/or retrieving a stent formed of a two-way shape memory alloy. An arrangement is provided by which the temperature of the stent is locally adjusted during delivery, repositioning and/or retrieval in a safe and controlled manner by engagement with an expandable and collapsible thermal transfer member situated on a catheter assembly.

25 Claims, 48 Drawing Sheets

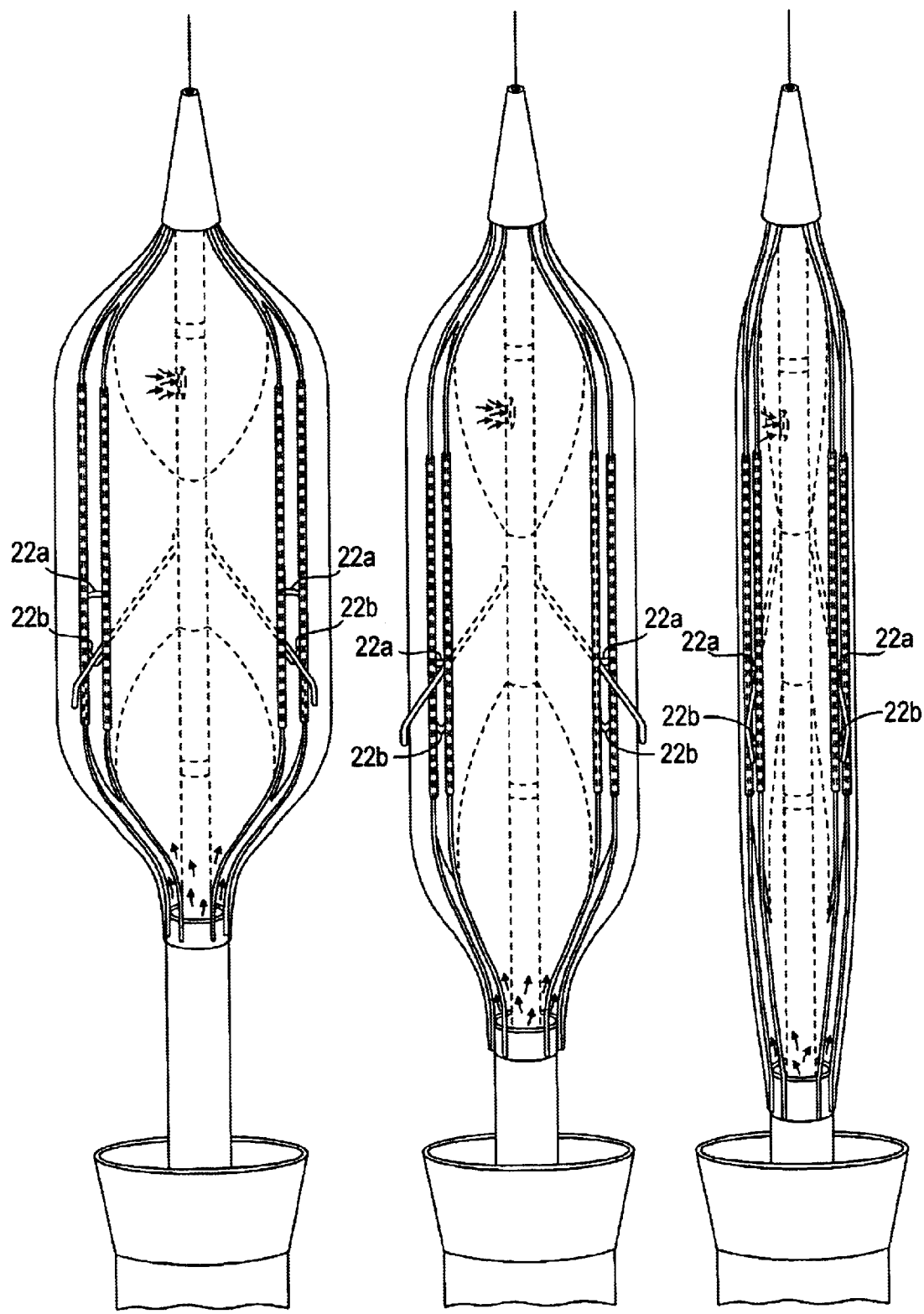
*FIG. 20a*   *FIG. 20b*   *FIG. 20c*

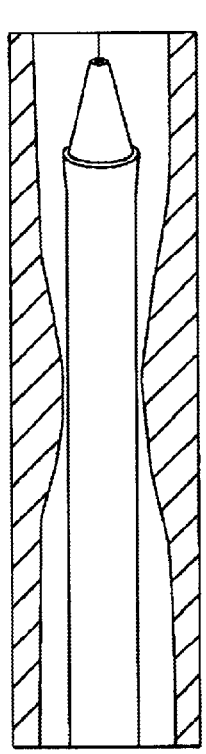
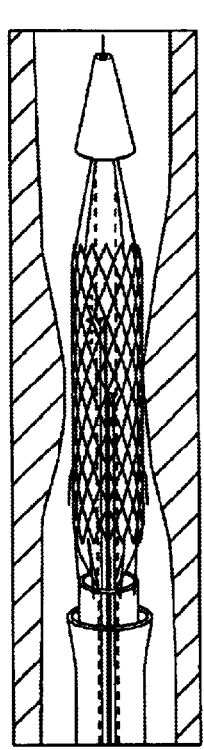
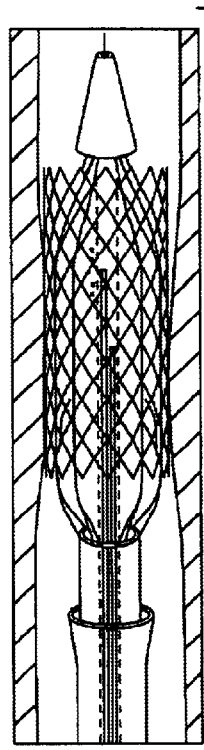
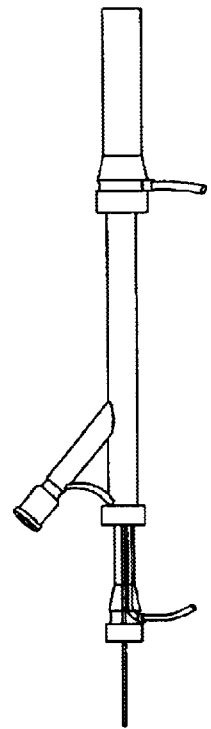
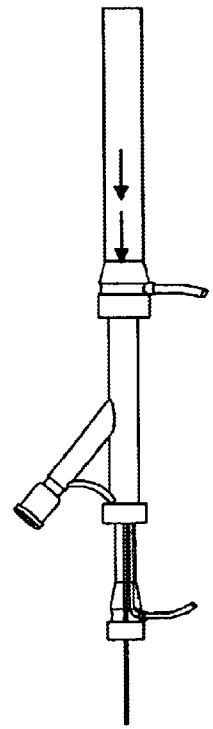
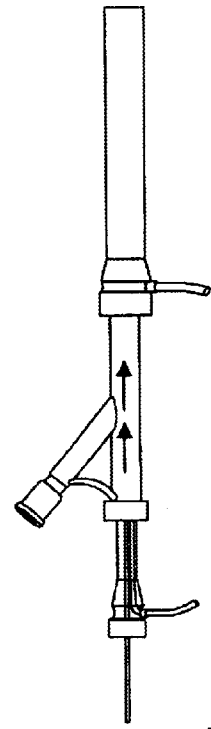
FIG. 21a
FIG. 21b
FIG. 21c

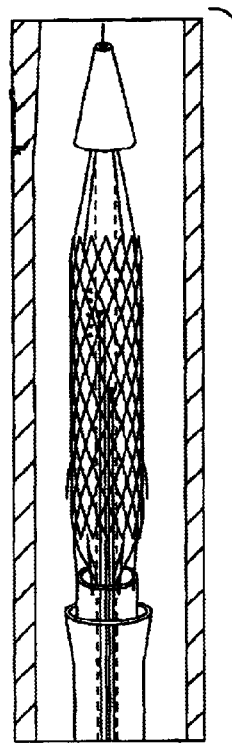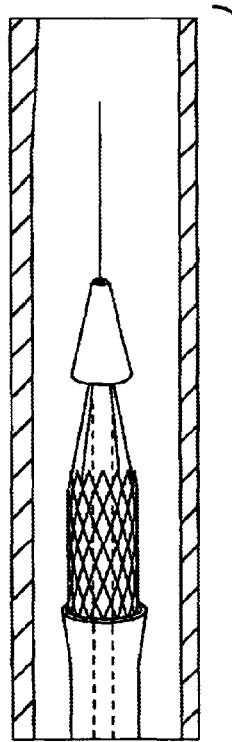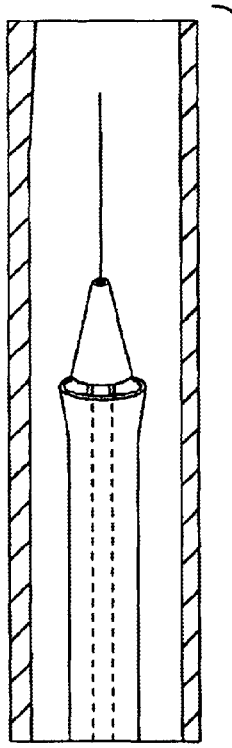
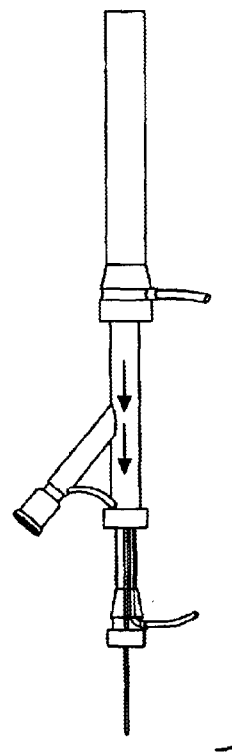
FIG. 22e
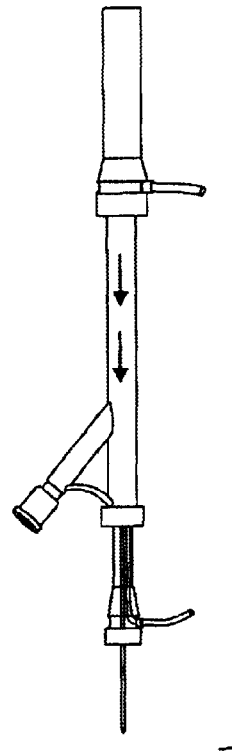
FIG. 22f
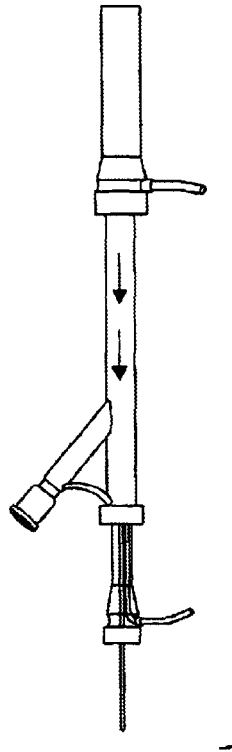
FIG. 22g

APPARATUS FOR DELIVERING, REPOSITIONING AND/OR RETRIEVING SELF-EXPANDING STENTS

FIELD OF THE INVENTION

The present invention generally relates to advanced medical endoluminal devices and methods of minimally invasive treatment of blockages of the blood vessels and other tubular organs. More particularly, the present invention relates to apparatus for delivering, repositioning and/or retrieving self-expanding stents for internal reinforcing of diseased tubular structure and/or for local delivery of pharmacological or radioactive agents having a beneficial advantage of reduction of re-stenosis.

BACKGROUND OF THE INVENTION

Reference is made to a related application entitled Methods for Delivery Repositioning and/or Retrieving Self-Expanding Stents filed concurrently with this application.

A stent is a generally longitudinal cylindrical device formed of biocompatible material, such as a metal or plastic, which is used in the treatment of stenosis, strictures, or aneurysms in body blood vessels and other tubular body structures, such as the esophagus, bile ducts, urinary tract, intestines or tracheo-bronchial tree. References hereafter to "blood vessels" and "vessels" will be understood to refer to all such tubular body structures. A stent is held in a reduced diameter state during its passage through a low profile catheter until delivered to the desired location in the blood vessel, whereupon the stent radially expands to an expanded diameter state in the larger diameter vessel to hold the vessel open. As discussed below, radial expansion of the stent may be accomplished by an inflatable balloon attached to a catheter, or the stent may be of the self-expanding type that will radially expand once deployed from the end portion of a delivery catheter.

Non-diseased vessels that are stented have a tendency to develop more aggressive intimal hyperplasia than diseased vessels. Intimal hyperplasia is part of the endothelialization process by which the stent becomes incorporated into the vessel wall as a result of the vessel's reaction to a foreign body, and is characterized by deposition of cell layers covering the stent. It eventually results in formation of a neointima, which coats the stent and buries it completely in the vessel wall.

Endothelialization generally improves patency rates and the more complete the apposition of the stent to the vessel wall, the more uniform and optimal is the degree of endothelialization. Of course, a fundamental concern is that the stent be deployed in the correct desired location in the vessel as precisely as possible in the first place. This is important when delivering radiation or medication to a particular location using the stent.

Therefore, firstly, it is important that a stent be deployed in the correct desired position in the blood vessel and, secondly that the stent be as completely apposed to the vessel wall as possible.

Stents fall into one of two categories based on their mechanism of deployment and radial expansion, namely, balloon-expandable stents and self-expanding stents.

Balloon-expandable stents (BES) are mounted in their reduced diameter state on nylon or polyethylene balloons, usually by manual crimping, while others are available pre-mounted. One example of a BE is shown in U.S. Pat. No. 4,733,665 to Palmaz. BES rely solely on balloon dilation to attain the desired expanded configuration or state. This enables BES to be deployed in a relatively controlled gradual manner. BES in general have more strength than self-expanding stents and initially resist deformation as well as recoil. BES behave elastically but eventually yield and become irreversibly, i.e. plastically, deformed under external force. Most BES are less flexible than self-expanding stents and are therefore less capable of being delivered through tortuous vessels and, when a BES is deployed in a tortuous vessel, it often straightens the vessel, forcing the vessel to conform to the shape of the stent rather than vice versa. This generally results in portions of the stent not being completely apposed to the vessel wall which in turn affects endothelialization and overall patency rate.

On the other hand, BES can generally be deployed in a relatively precise manner at the correct desired location in the vessel since they can be deployed in a controlled gradual manner by gradually controlling the inflation of the balloon. This ability to gradually control the expansion of the stent, along with the fact that BES rarely change their position on the balloon during inflation, enable fine adjustments to be made by the operator in the position of the stent within the vessel prior to stent deployment.

Self-expanding stents (SES) are formed of braided stainless steel wire or shape-memory alloy such as nitinol and are generally delivered to desired locations in the body in a reduced diameter state in a low profile catheter while covered by an outer sheath which partially insulates the SES from body temperature and mechanically restrains them.

Nitinol is an alloy comprised of approximately 50% nickel and 50% titanium. Nitinol has properties of superelasticity and shape memory. Superelasticity refers to the enhanced ability of material to be deformed without irreversible change in shape. Shape memory is the ability of a material to regain its shape after deformation at a lower temperature. These physical properties of nitinol allow complex device configurations and high expansion ratios enabling percutaneous delivery through low profile access systems.

Superelasticity and shape memory are based on nitinol's ability to exist in two distinctly different, reversible crystal phases in its solid state at clinically useful temperatures. The alignment of crystals at the higher temperature is called the austenite (A) phase; the alignment of crystals at the lower temperature is called the martensite (M) phase. In between is a temperature interval of gradual transition between the A and M phases.

Under external force, the shape of a nitinol device can be greatly deformed without irreversible damage. Depending on the temperature at which this external force is applied, superelastic or shape memory effects prevail. In close vicinity to or above the temperature defining transition into the full A state, superelasticity results: as soon as the deforming force is released, the device immediately assumes it original shape. When nitinol is deformed at or below the lower temperature of the complete M transition, the shape memory effect can be exploited. The device retains its deformed shape even after the external force is removed as long as the temperature of the environment stays below the temperature of transition into A phase. Only during heating does the device resume its original shape.

While the shape memory effect is essentially a one-way type phenomena in which shape recovery occurs only upon heating the alloy to a temperature defining transition to the full A phase, by subjecting the alloy itself to a biasing force, i.e. an internal stress formed by dislocations introduced by plastic deformation in the alloy, a two-way shape memory can be imparted to the alloy so that cooling the alloy will induce a shape change.

One type of self-expanding stent is constructed of wire formed of a shape-memory alloy, such as nitinol, having a transition temperature of about body temperature, i.e. 37° C. For example, reference is made to U.S. Pat. No. 5,746,765 to Kleshinski et al. The one-way transition temperature is the temperature of transformation of a nitinol device from its collapsed state into a fully expanded configuration. The stent is preloaded on a low profile catheter by crimping the stent at room temperature (at which it can be plastically deformed) onto the catheter. An outer sheath covers the crimped stent and at least partially thermally insulates the stent as it is delivered to the desired location. Upon reaching the desired location, the sheath is withdrawn and the stent is exposed to body temperature whereupon it is naturally warmed to body temperature and expands to its expanded diameter state in supporting contact with the vessel wall. In a fully expanded state within the human body, the stent is capable of exerting considerable radial force on the surrounding structures, which allows mechanical opening of the vessel lumen and maintaining its long-term patentcy for free passage of flow.

If an alloy is used for which shape recovery occurs above body temperature, the SES must be heated after release into the body. If shape recovery occurs below body temperature, the device may be cooled during the delivery to prevent expansion inside the delivery catheter. If shape recovery occurs at body temperature, no heating or cooling is necessary during the delivery and deployment, provided delivery is relatively speedy. If, however, a tortuous iliac anatomy or other interference delays prompt deployment of a nitinol stent with these characteristics, premature warming to body temperature could cause expansion in the delivery sheath, increase friction, and interfere with delivery. In this instance, flushing with a cool solution has been suggested.

SES do not require any special preparation prior to deployment. SES behave elastically throughout their lifetime, and do not become irreversibly deformed. When deployed, the nominal diameter is purposely selected to be greater that the diameter of the vessel. Therefore, once deployed, an SES exerts continuous outward force on the vessel as it tries to expand to its original dimensions. The ability of an SES to continuously exert an outward force on the vessel coupled with the greater flexibility of SES, generally results in optimal wall apposition, thereby optimizing endothelialization and improving patency rates. Nitinol self-expanding stents have been designed having good radial and hoop strength.

However, while SES are preferable relative to BES in many applications with respect to achieving optimized endothelialization and increased patency rates, currently available arrangements for delivering and deploying SES are not entirely satisfactory. It has generally not been possible to deploy SES in the correct desired location in a vessel as precisely as in the case of BES with currently available delivery arrangements for the reason that the temperature of the SES rapidly increases to body temperature upon withdrawal of the outer sheath and therefore the stent quickly expands into engagement with the vessel wall. Consequently, there is not always enough time to finely adjust the position of the SES as it quickly expands, and it is not uncommon for the distal end of an SES, which is exposed to body temperature first, and which therefore expands before the rest of the SES, to engage and become attached to the vessel wall in the wrong position and in turn inhibit or prevent further adjustments in the position of the SES in the vessel.

Another drawback in conventional arrangements for delivering and deploying SES, as compared to BES, is that during deployment while BES are advantageously pressed against the vessel wall with a relatively large outward force by the dilating balloon in the manner of an angioplasty to insure attachment of the BES to the vessel wall, SES must rely solely on the outward force exerted by the expanding SES to provide initial attachment. It is common to supplement the SES placement with a subsequent balloon angioplasty, which requires exchange of the stent delivery system after completion of stent deployment for a balloon catheter.

Still another drawback in conventional arrangements for delivering and deploying SES is the possibility that when delivery is protracted, the SES is exposed to body temperature inside the delivery system. The deployment process can then become more difficult—the device may open abruptly after being freed from the system and may "jump" beyond the target as the SE expands during deployment. BES cannot be repositioned or retrieved after deployment and while arrangements have been proposed for enabling the repositioning and/or retrieval of SES formed of two-way shape memory material, no practical workable arrangement has been developed.

A malpositioned stent often requires an additional stent placement to correct the mistake and achieve the desired results. The stents will remain in the vessel for the entire life of the patient. In a high percentage of patients, the stent will become the site of recurrent stenosis due to an aggressive neointimal proliferation. These patients require repeated interventions, which often include balloon angioplasty and/or additional stent placement.

The most striking illustration of these problems is seen in cardiac patients. Stents and balloon angioplasty transformed the care of patients with heart disease. Each year, about 700,000 patients in the U.S. undergo angioplasty, in which a balloon is used to clear an obstruction in a coronary artery and a stent is deployed to keep it open. Yet a disturbingly high 15% to 20% of the procedures fail within six months, due to the aggressive neointimal proliferation. These patients will often undergo further major treatments, which might be repeated several times.

The need to be able to reposition and/or retrieve stents from a vessel also arises from the fact that heart researchers and stent manufacturers are developing a new generation of stents that not only prop open the vessel, but which deliver drugs to the site of the blockage in an effort to minimize or eliminate neointimal proliferation and keep the vessel open for long periods of time. Studies have shown that stents coated with a drug called rapamycin, essentially eliminates re-stenosis. Other medications, such as nitric oxide and paclitaxel or similar compounds, also have a potential to prevent proliferation of scar tissue by killing such cells. One concern is whether the drugs might work too well, inhibiting not only re-stenosis, but also the necessary growth of the thin layer of neointima. As previously described, this thin layer of cells, which grows over the stent, smoothes its surface (similar to a layer of Teflon), so blood cells can flow over it without damaging themselves. A damaged blood cell initiates a chemical cascade, which results in clot formation. Therefore an exposed bare metallic stent carries a risk of inducing thrombus formation within it.

The potential of radioactive stents to prevent re-stenosis is an additional area of active research, since local radiation has been shown to inhibit the growth of neointima and halt the progression of atherosclerotic disease.

One can therefore appreciate the benefit of being able to retrieve a stent used for local drug delivery or radiation treatment, after it has achieved its desired effect. This would eliminate potential risk of thrombus formation at the site of the exposed bare stent.

In summary, ideally an optimal stent and associated delivery system should possess and combine all the positive traits mentioned so far in each of the stent categories. The stent should be pre-loaded on the delivery apparatus and should not require special preparation. It should be flexible to enhance apposition to the vessel wall. It should provide a controlled gradual deployment without stent migration to ensure deployment of the stent in the correct location. Lastly, in case of a malpositioned stent, or stent which is deployed for the purpose of its temporary effect, such as for local drug delivery, the system should have the option of enabling repositioning and/or retrieval of the stent.

SES can be preloaded on the delivery apparatus, do not require special preparation and are flexible. However, to date, no satisfactory method or apparatus is available for obtaining a controlled gradual deployment of an SES without stent migration, or for repositioning and/or retrieving a SES. While arrangements have been suggested in the prior art for delivering SES to a correct location in a precise manner and for repositioning and retrieving SES formed of two-way shape memory material, these prior art arrangements all have drawbacks and have not been adopted in practice.

An arrangement for delivering, repositioning and/or retrieving an SES formed of a two-way shape memory alloy capable of expansion or collapsing in the radial direction in accordance with changes in temperature is disclosed in U.S. Pat. No. 5,037,427 to Harada et al. According to Harada et al., a stent is made of nitinol alloy trained to have two-way shape memory. The stent is in an expanded diameter state at about body temperature and in a reduced diameter state at a temperature below body temperature. In delivering the stent, the stent is mounted in the reduced diameter state at the distal end of a catheter over a portion of the catheter having a number of side ports. Cooling water supplied through the catheter flows out from the side hole and is brought into contact with the stent during delivery to maintain the stent below body temperature and therefore in the reduced diameter state. When the SES is positioned at the desired location, the supply of the cooling water is stopped and the stent is warmed by the heat of the body and expands into supporting engagement with the wall of the vessel. The catheter is then withdrawn. In retrieving an already-positioned SES using this system, the distal end portion of the catheter is inserted into the expanded stent lumen and a cooling fluid is introduced into the catheter and discharged through the side ports at the distal end region into the vessel whereupon the stent is cooled and purportedly collapses onto the distal end portion of the catheter. The stent is retrieved by withdrawing the catheter. The patent suggests that the position of the stent can also be changed using this technique.

U.S. Pat. No. 5,746,765 to Kleshinski, Simon, and Rabkin also discloses a stent made from an alloy with two-way shape memory, which expands inside the vessel due to natural heating to body temperature. The stent is covered with an elastic sleeve. When the metal frame is softened by decreased temperature, the sleeve overcomes its radial force and promotes its further contraction for easier retrieval.

However, in both the arrangements disclosed in Harada et al. and Kleshinski et al., a substantial amount of very cold solution must be infused into the vessel in order to reduce the local temperature of the environment surrounding the stent. Cold temperature around the stent must be maintained for some time until the stent is delivered or recovered for retrieval or repositioning. This technique appears to be clinically impractical and not safe due to high risk of potential tissue and blood cell damage.

U.S. Pat. No. 6,077,298 to Tu et al. discloses a retractable stent made from a one-way shape-memory alloy, such as nitinol, that can be deployed into the body by means of dilation with a balloon catheter. For the stent retrieval, a radio frequency current within the range of 50 to 2,000 kHz must be applied directly to the stent to provide partial collapse of the stent after it is heated to a temperature above 43° C. to 90° C. However, if the transition temperature of the stent material is in the range of 43° C.–90° C., the radial force of the device will be greatly reduced at the body temperature of 37° C., and may not be sufficient for therapeutic effect. Heating of the stent to almost a boiling temperature can cause irreversible damage to vascular wall and blood coagulation.

U.S. Pat. No. 5,961,547 to Razavi, U.S. Pat. No. 5,716,410 to Wang et al., U.S. Pat. No. 5,449,372 to Schwaltz et al. and U.S. Pat. No. 5,411,549 to Peters disclose temporary or retractable stents in the shape of a spiral coil or a double helix. Although these stents are made of different materials, such as metal or plastic, and have differences in the techniques of their deployment (heat-activated, self-expanding or balloon expandable), as well as methods of their retrieval (mechanical straightening vs. softening by increasing temperature vs. latch retraction), all of them have one common feature. The stents are connected with a wire extending outside the patient at all times and when they have to be removed, they are simply retracted back into the catheter with or without prior softening of the material. For this reason these stents cannot be left in the human body for more than a couple of days. The connecting wire can traverse the entire body if the stent is placed in the coronary or carotid artery from the femoral approach, increasing risk of thrombus formation around the wire and distal embolization, thrombosis of the femoral artery and infection of the inquinal region.

U.S. Pat. No. 5,941,895 to Myler et al. discloses a removable cardiovascular stent with engagement hooks extending perpendicular to the axis of the stent into the vessel lumen. The stent retrieval technique requires introduction of an extraction catheter, which is adapted to grasp the engagement hooks of the stent with subsequent stent elongation in axial direction and reduction of its cross-sectional diameter. However, the stent with inwardly extending engagement members will likely require a larger delivery system than regular tubular devices. Any manipulation of the catheters and guidewires in the stented area may potentially accidentally engage the hooks of the stent with its subsequent dislodgment and damage of, the vessel. The hooks extending into the vessel lumen will cause turbulence of blood flow around them, leading to activation of the coagulation system and thrombus formation.

U.S. Pat. No. 5,833,707 to McIntyre et al. discloses a stent formed from a thin sheet of metal that has been wound around itself into a general cylindrical tight roll and expands inside the body by heating to body temperature. This stent is designed for predominant use in the human urethra and is not suitable for cardiovascular applications due to very large metal surface that could be thrombogenic and increased size of the delivery system. The stent can be removed from the body with the help of a cannula or pincer grips for grasping the edge of the stent. By rotating the pinched stent, the pincer or cannula cause the stent to telescopically coil into smaller diameter, which can then be retrieved from the urethra. This technique could be too traumatic for cardiovascular applications. The recovery apparatus will likely have a large profile, making this method not practical or feasible for percutaneous use in blood vessels or other tubular organs.

U.S. Pat. No. 5,562,641 to Flomenblit et al. discloses a spiral or cylindrical stent made from alloy with two-way shape memory capabilities. The stent expands inside the body by heating to the temperature of 50° C. to 80° C. with an electric current, injection of hot fluid, external radio frequency irradiation or use of radio frequency antenna inside the catheter. The stent can be removed from the body after cooling to a temperature, ranging from −10° C. to +20° C., at which the stent partially collapses in diameter and can be grasped with a catheter for retrieval. As discussed above, heating of the stent to a temperature over 80° C. could be unsafe, especially with intravascular injection of hot fluid. Use of external radio frequency irradiation will cause heating not only of the stent, but all tissues from the skin surface to the stented vessel deep inside the body and beyond. Cooling the stent to below the freezing temperature by injection of a very cold fluid into a blood circulation for removal is also impractical and not feasible in a real clinical setting.

SUMMARY OF THE INVENTION

Accordingly, it is an object of the present invention to provide new and improved apparatus for delivering stents to desired locations in blood vessels and other tubular body structures.

Another object of the present invention is to provide new and improved apparatus for delivering self-expanding stents to desired locations in body vessels by which the stent can be deployed in a controlled gradual manner to thereby enhance the accuracy of positioning.

Still another object of the present invention is to provide new and improved apparatus for delivering self-expanding stents to desired locations in body vessels by which the stent can be deployed in a controlled gradual manner safely without infusing a cooling liquid into the vessel or otherwise affecting general body temperature or causing systemic affects.

Yet another object of the present invention is to provide new and improved apparatus for delivering self-expanding stents to desired locations in body vessels which eliminate the possibility of migration of the stent during deployment.

A further object of the present invention is to provide new and improved apparatus for repositioning and/or retrieving self-expanding stents in and from a body vessel without infusing a cooling or heating liquid into the vessel or otherwise affecting general body temperature or causing systemic affects.

A still further object of the present invention is to provide new and improved apparatus for repositioning and/or retrieving self-expanding stents which eliminates the possibility of migration of the stent during repositioning.

A still further object of the present invention is to provide new and improved apparatus for providing supplemental balloon angioplasty after stent deployment with the same system, eliminating the need for exchanging catheters.

Briefly, in accordance with one aspect of the present invention, these and other objects are attained by providing an arrangement for delivering a self-expanding stent formed of a shape memory alloy to a desired location in a body vessel by placing the stent in a collapsed condition in contact, or in other local heat transfer relationship, with a thermal transfer device coupled to a catheter assembly, and delivering the stent in its collapsed condition to the region of the desired location in the body vessel while in contact or other local heat transfer relationship with the thermal transfer device. According to the invention, the temperature of the thermal transfer device can be controlled in a safe and non-invasive matter so that the expansion of the stent can be controlled (thereby enabling the precise positioning of the stent) by suitably varying the temperature of the thermal transfer element, and therefore the stent, during delivery and/or deployment.

For example, in the case where the stent is made of a shape memory alloy having a transition temperature such that the stent from which it is formed is in its expanded diameter state at or slightly below body temperature (37° C.), the temperature of the thermal transfer device is maintained below body temperature during delivery of the stent and at the beginning of deployment to allow precise positioning, while in the case where the stent is made of a shape memory alloy having a transition temperature such that the stent obtains its expanded diameter state at a temperature greater than body temperature, the temperature of the thermal transfer element is increased to the higher temperature after the stent in its collapsed state has been precisely positioned at the desired location whereupon the stent expands to its expanded diameter state.

The thermal transfer device is constructed such that the temperature of the stent can be controlled quickly, precisely and non-invasively. Specifically, the temperature of the stent can be changed quickly since the stent is in local heat transfer relationship with the thermal transfer device. For present purposes, "local heat transfer relationship" means either the stent contacts the thermal device or the stent and thermal transfer device are sufficiently close, so that heat is transferred between the stent and the thermal transfer device without materially affecting the temperature of the surrounding tissue. The stent's temperature can be controlled relatively precisely since the temperature of the stent, which has a low mass, will essentially correspond to the temperature of the thermal transfer device, which has a much higher mass. Moreover, no liquid or gas will be infused into the vessel during the entire procedure, such as in the case of Harada et al U.S. Pat. No. 5,037,427.

In preferred embodiments of the invention, the thermal transfer device comprises an arrangement itself capable of controlled radial expansion to about the diameter of a stent in its expanded diameter state, and contraction to a collapsed state. This feature, in some of its embodiments, is not only advantageous with respect to the initial delivery of a self-expanding stent with an option of performing a balloon angioplasty at the same time, but, additionally, makes the arrangement particularly adapted for repositioning and/or retrieving stents formed of two-way shape memory alloys that have already been deployed in a vessel, such as in the repositioning of a misplaced stent, removal of a stent placed for temporary indications, or the removal of a stent that has completed the delivery of mediation or radiation to a particular area. Specifically, for removal and/or repositioning of the stent, the thermal transfer device is structured and arranged to be initially positioned in the lumen of the already deployed stent in a collapsed condition, out of contact or other local heat transfer relationship with the deployed stent, and then expanded into contact, or other local heat transfer relationship with the stent. The temperature of the heat transfer device is adjusted so that the temperature of the deployed stent is reduced to that at which the stent obtains a relaxed, flexible state whereupon it separates from the vessel wall. The stent can then be drawn into the catheter assembly and either removed from the body or repositioned using the initial delivery process described above.

In one embodiment in which the thermal transfer device comprises an inflatable and expandable balloon member, the initial delivery of a stent formed of a shape memory alloy can be assisted in the manner of angioplasty by inflating the balloon to forcibly urge the stent against the vessel walls.

In accordance with another aspect of the invention, the catheter assembly includes a capturing device for releasably coupling the stent to the catheter assembly during deployment, as well as for grasping an already-deployed stent for purposes of retrieval and/or repositioning. The capturing device prevents the stent from being carried away by the bloodstream or from migrating on the catheter, and is also structured and arranged to assist in drawing the stent in its flexible and pliable condition into the catheter assembly for repositioning and retrieval.

In a preferred embodiment, the thermal transfer device comprises a balloon member connected to a catheter assembly defining a contained chamber having an outer wall, at least a part of which constitutes a thermal transfer material. The arrangement further includes apparatus for circulating a thermal transfer fluid from the proximal end region of the catheter assembly into the interior of the chamber and for providing an outflow of the thermal transfer fluid from the interior of the closed chamber to the proximal end region of the catheter assembly. As used herein, the term "fluid" refers to either a liquid or a gas. The temperature of the circulating thermal transfer fluid is controlled either by heating or cooling means situated at the proximal end of the catheter assembly outside of the body, or by heating means situated within the chamber of the thermal transfer device, such as optic fibers for transmitting a laser beam to heat the fluid circulating within the thermal transfer device, an internal ultrasound probe situated within the thermal transfer device, or a spiral resistance heating wire which will be heated by induction of an electric current by applying the power source or magnetic field from an external source. Alternatively, the surface of the balloon can be heated for direct heat transfer to the stent. For example, resistance heating wires may be situated on the outer surface of an expandable balloon, as can a spiral surface wire which can be heated by induction through the application of a power source or magnetic field from an external source, or externally situated optic fibers for transmitting a laser beam along and around the surface of the balloon. The stent is in contact with the heat transfer surface during delivery and depending on the transition temperature of the alloy from which the stent is made, the stent is either cooled, heated, or left at ambient temperature through contact or other local heat transfer relationship during delivery. In capturing an already deployed stent, the balloon in its collapsed condition is situated in the lumen of the already deployed stent, and then expanded into contact with the stent. Cooling liquid is circulated through the balloon which cools the stent causing it to separate from the vessel wall and to become flexible and pliable so that it can be drawn into the catheter assembly.

In another preferred embodiment, the thermal transfer device comprises an expandable frame formed from a plurality of conductive resistance wires. The frame can be expanded by suitable adjustment of the catheter assembly to bow the resistance wires radially outwardly into contact with the stent. The wires are heated by connection to an external source of electricity and are in direct contact heat transfer relationship with the stent.

DESCRIPTION OF THE DRAWINGS

A more complete appreciation of the present invention and many of the attendant advantages thereof will be readily understood by reference to the following detailed description when considered in connection with the accompanying drawings in which:

FIGS. 20a–20c are three perspective views showing sequential steps of the collapse of the second version of the third embodiment of the thermal transfer device from its expanded diameter condition;

FIGS. 21a–21f are six perspective views showing sequential steps of the operation of the second version of the third embodiment of the invention in connection with deploying a stent, and also illustrating the corresponding operation of the catheter assembly at its proximal end;

FIGS. 22a–22g are seven perspective views showing sequential steps of the operation of the second version of the third embodiment of the invention in connection with retrieving the stent, and also illustrating the corresponding operation of the catheter assembly at its proximal end;

DESCRIPTION OF THE PREFERRED EMBODIMENTS

Figure 1:
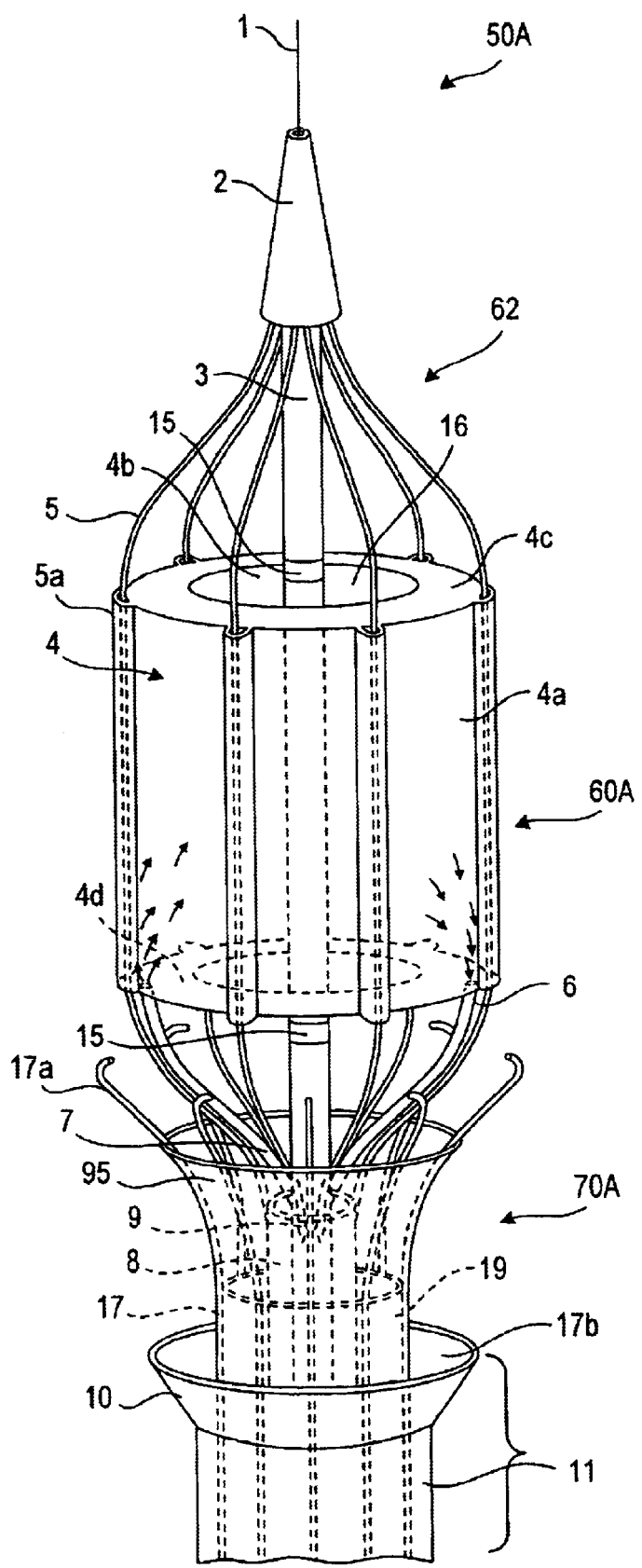
FIG. 1 is a perspective view of a first embodiment of a catheter assembly, including a first version of a hook-type stent capturing device, and an associated sleeve-type thermal transfer device in accordance with the invention, with the thermal transfer device shown in expanded condition.

Various embodiments of apparatus for delivering a self-expanding stent and/or for retrieving and repositioning an already-positioned self-expanding stent in accordance with the invention are described herein. In all cases, where the apparatus is to be used for delivering a stent, the stent may be formed of a shape memory material having either a one-way shape memory or a two-way shape memory. However, in the case where the apparatus is to be used for retrieving and/or repositioning a stent that is already in place, the stent must be formed of a two-way shape memory alloy.

For purposes of describing the invention, except where noted, the stent to be delivered, retrieved and/or repositioned is formed of a two-way shape memory material having or trained to have a second cold memory. When released into the vessel or other tubular structure and naturally warmed to first transition temperature at or below body temperature of 37° C., the stent expands and recovers its previously imprinted intended functional shape at or below body temperature. In a fully expanded state within the human body, the stent is capable of exerting considerable radial force on the surrounding structures, which allows mechanical opening of the vessel lumen and maintaining its long-term patency for free passage of flow. When the fully expanded stent is cooled to a temperature in the range of −10° C. to +35° C., it becomes compliant, has a reduced stress state, and can be compressed into a reduced diameter, small enough to fit within a low profile delivery system for percutaneous insertion.

The stent is constructed of a single continuous thermal shape memory wire, can be cut with laser technology, or formed with a photoetching technique from thermal shape memory tubing to create a mesh-like configuration. The expansive force and the stiffness along the length of the stent can be modulated by changes in the dimensions of the cell geometry. There are no open or sharp edges at either end of the device. This prevents injury to the wall while improving the ability to position, reposition or retrieve the device. Because the wire never overlaps itself, the stent wall thickness is never greater than the wire diameter and both surfaces are smooth. The cells of the stent create an open mesh, which is favorable for maintaining the patency of side branches, and also minimized the length changes, which occur between the collapsed and expanded forms of the device. The shortening of the stent during its expansion depends on the cell geometry, but usually does not exceed 10% of the length of the stent in its completely expanded state. In a preferred embodiment, an intraluminal medical device may include a permanent or temporary implantable stent or stent-graft, a permanent or temporary device impregnated with medications or radioactivity for local therapy, or a temporary retrievable/repositionable device.

For the purpose of non-surgical treatment of vascular aneurysms, acutely bleeding vessels, or other perforated tubular organs (GI tract, bile ducts, tracheo-bronchial tree etc.), the stent can be covered with a graft material or coating. The graft material is anchored at each end to an exposed section of the metallic scaffold of the stent. The design of the device is such that length changes that occur during delivery can be largely limited to the short uncovered stent segments at either end of the device. The stents can also be impregnated with certain medications or provided with a radioactive coating, for local delivery of drugs or radiation to the diseased vessel.

Figure 2:
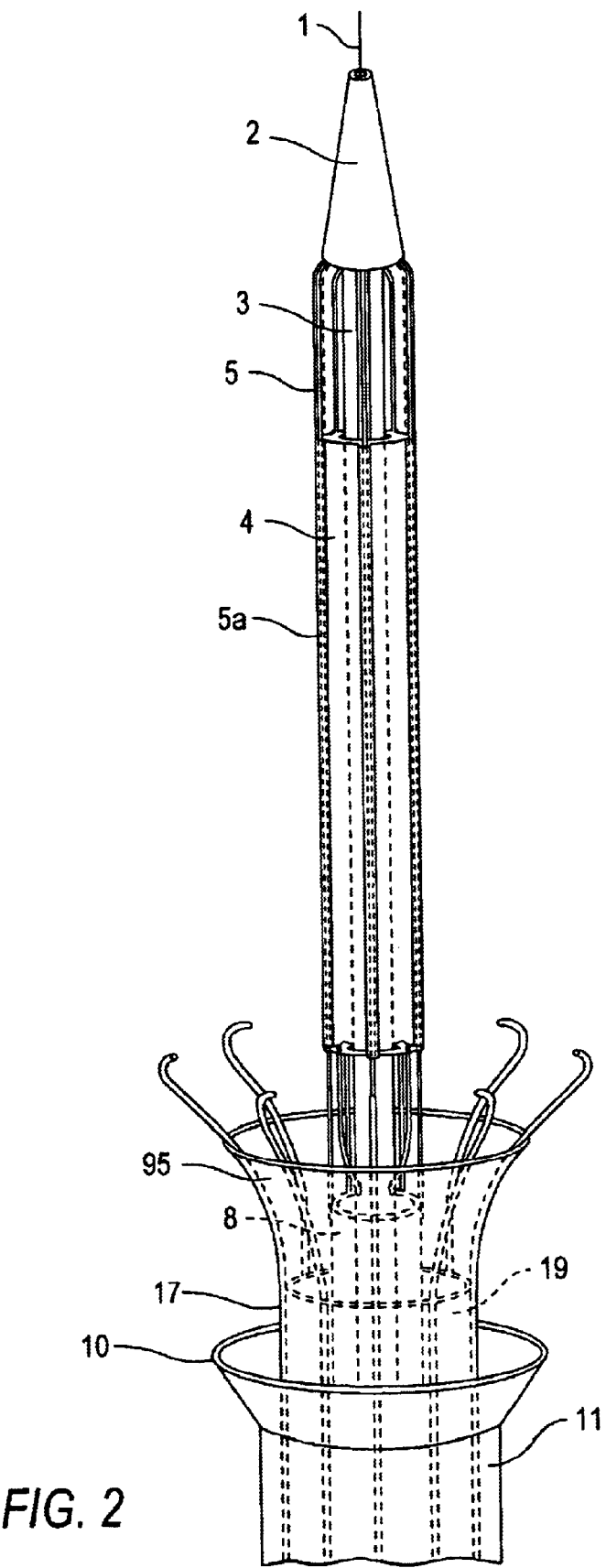
FIG. 2 is a perspective view of the first embodiment with the thermal transfer device in a collapsed condition.
Figure 3:
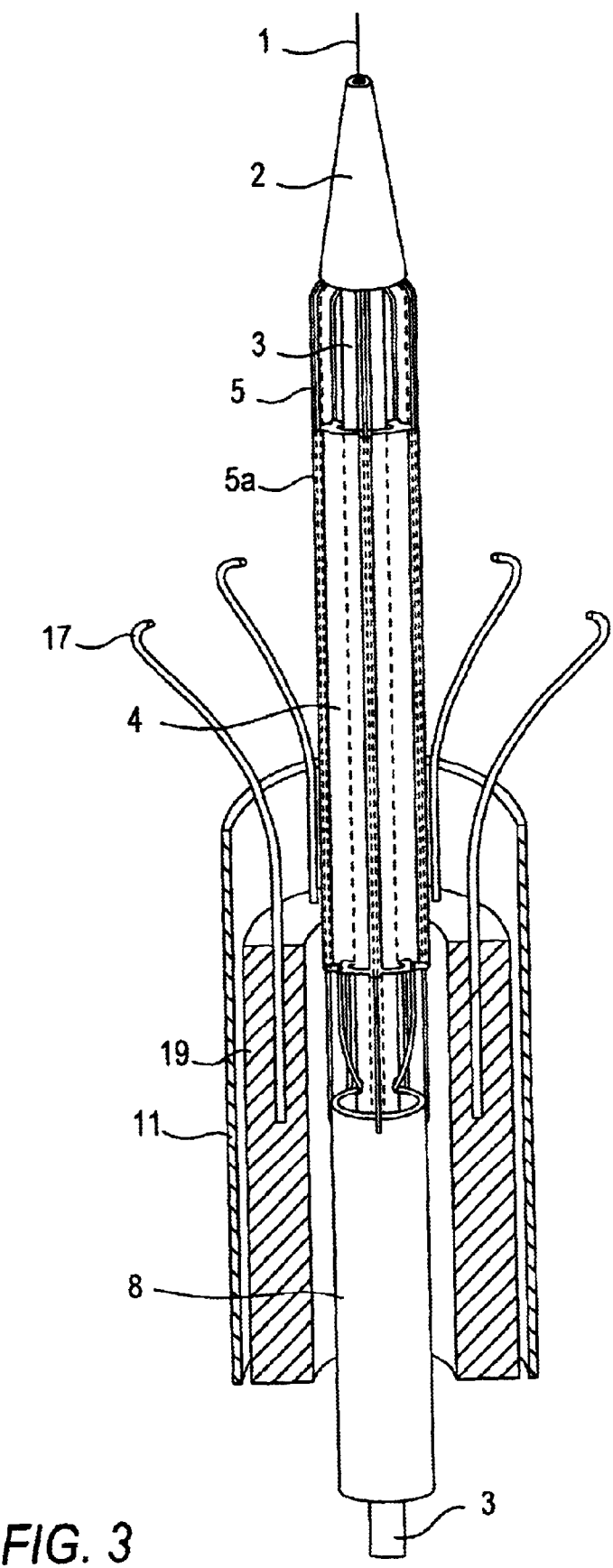
FIG. 3 is a perspective view of the first embodiment, partially broken away to show the hook-type stent capturing device of the catheter assembly according to the invention.
Figure 4:
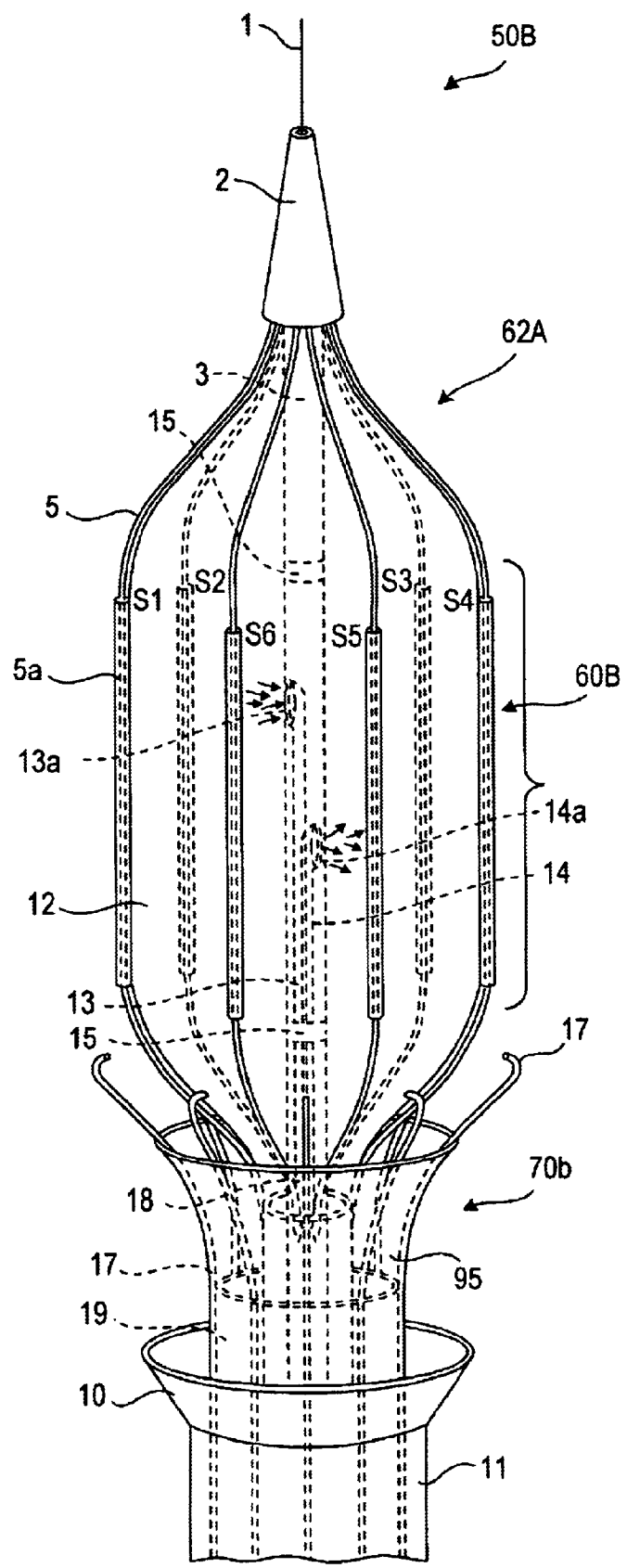
FIG. 4 is a perspective view of a first version of a second embodiment of a catheter assembly and associated "solid" thermal transfer device in an expanded condition in accordance with the invention, with a first version of an arrangement for circulating thermal transfer fluid through the thermal transfer device, and a hook-type stent capturing device.
Figure 5:
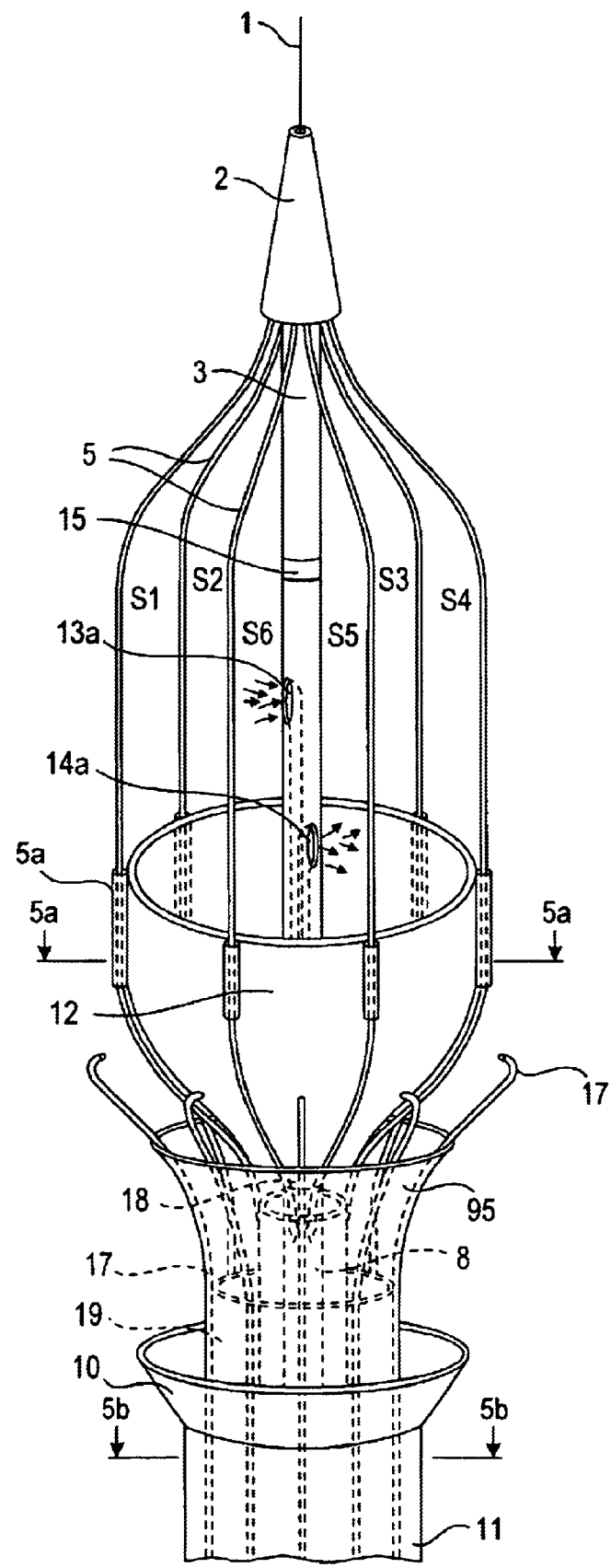
FIG. 5 is a perspective view of a first version of the second embodiment, partially broken away to show the first version of the circulation arrangement.
Figure 5A:
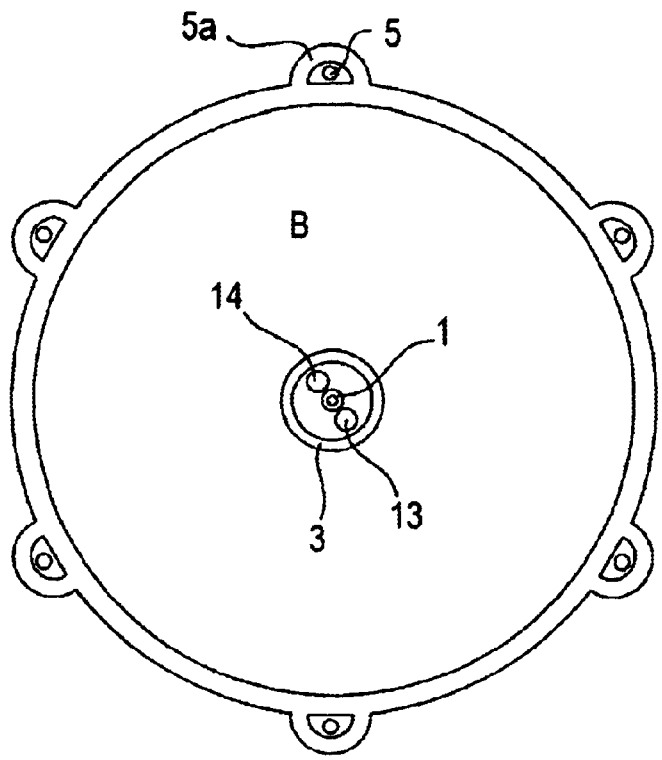
FIG. 5a is a section view taken along line A—A of FIG. 5.
Figure 5B:
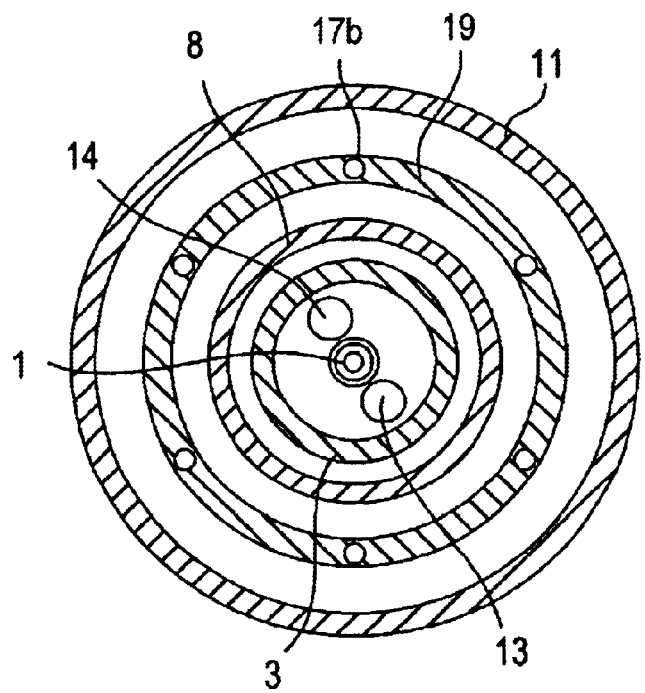
FIG. 5b is a section view taken along line B—B of FIG. 5.
Figure 6:
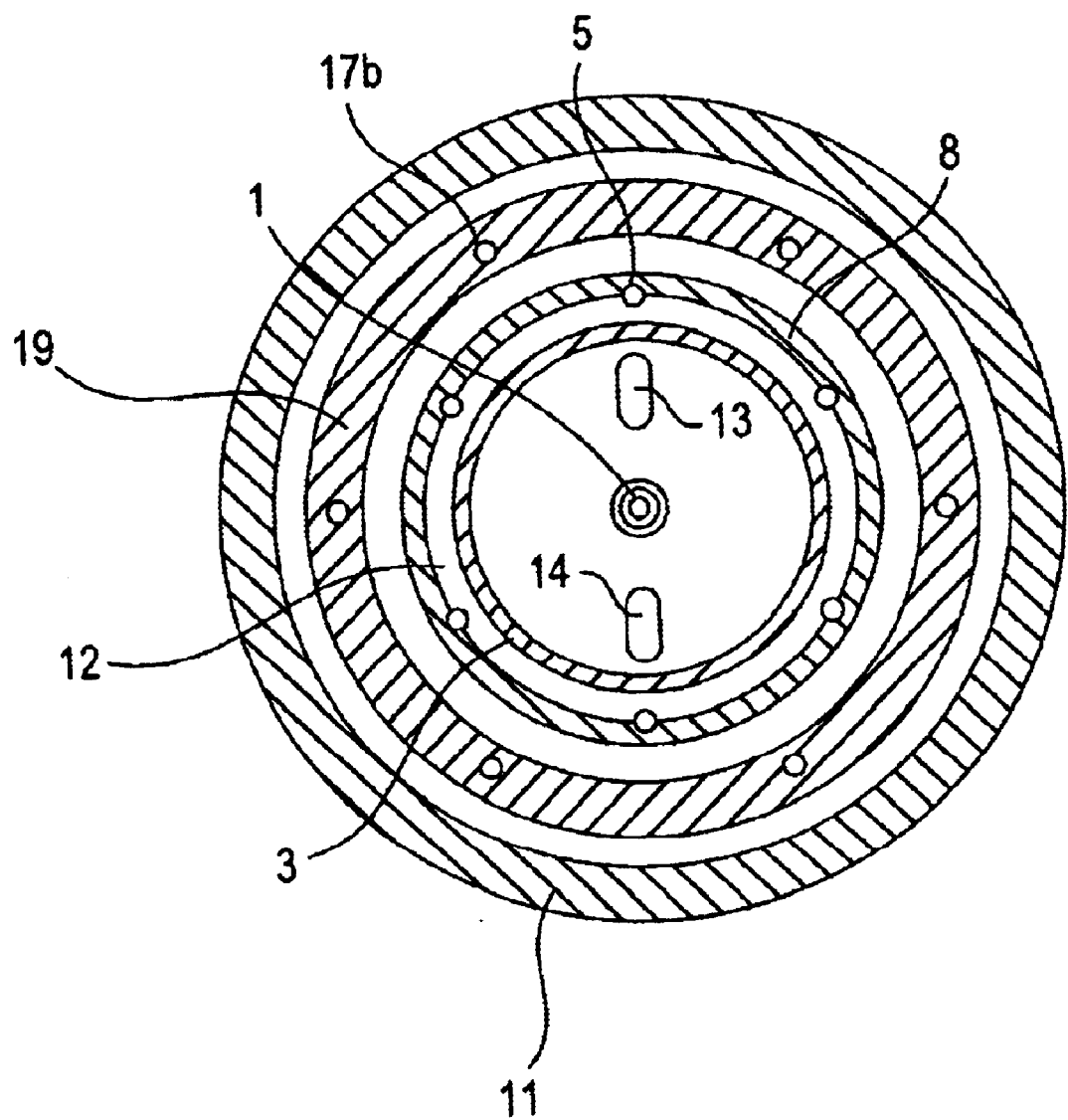
FIG. 6 is a transverse section view of the embodiment of FIG. 5 through the stent-receiving sheath.

Referring now to the drawings in which like reference characters designate identical or corresponding parts throughout the several views, and more particularly to FIGS. 1–3, a first embodiment of apparatus in accordance with the invention comprises a catheter assembly 50A (only the distal end region of which is shown), a thermal transfer device 60A connected to catheter assembly 50A and an associated stent capturing device 70A. Catheter assembly 50A comprises a low profile outer core catheter 8, having an inner movable core catheter 3, an inner stent-capturing sheath 19 situated over the outer core catheter 8, and an outer stent-receiving sheath 11. In this embodiment, the thermal transfer device 60A comprises a frame assembly 62 to which an expandable balloon 4 is connected. Balloon 4 has a sleeve-type configuration, i.e., the balloon 4 has an annular cross-section along its entire length. As discussed below, this shape is advantageous since the flow of blood or other body fluid which normally occurs in the vessel will be maintained during inflation of the balloon through the opening 16 in the center of the balloon 4. As described below, the balloon is formed of material having suitable thermal transfer characteristics, i.e. relatively good heat conductivity. The frame assembly 62 includes a plurality of scaffolding wires 5, each wire 5 having a distal end molded into a conus 2, which has a tapered configuration for easy percutaneous insertion, and a proximal end 9 molded into the outer core catheter 8. The scaffolding wires are preferably formed of a material that exhibits superelastic properties.

The outer core catheter 8 has a distal end which is situated proximally to the distal end of the inner core catheter 3 so that a projecting portion of the inner core catheter 3 extends beyond the distal end of the outer core catheter 8. Each of the scaffolding wires has one end fixed to the distal end of the projecting portion of the inner core catheter 3 at conus 2, another end fixed to the distal end of the outer core catheter 8, and a central region attached to the balloon 4. Thus, the apparatus includes a stent capturing device including at least one elongate member 17 coupled to the catheter assembly 50A at its distal end region and having a free end portion 17a situated proximate to the balloon 4 for releasably holding a stent situated on the balloon during deployment. and for releasably grasping the stent during retrieval and repositioning.

It will be seen that by relative movement of the inner and outer core catheters from the proximal end of the catheter assembly to shorten the projecting portion of the inner core, the wires 5 will bow or bend and therefore expand the balloon to its expanded condition shown in FIG. 1. On the other hand, relative movement of the inner and outer core catheters to lengthen the projecting portion of the inner core straightens the wires and collapses the balloon to its collapsed condition as seen in FIG. 2. The frame assembly can be formed in other manners, such as by the use of elongate plastic members similarly affixed to the inner and outer core catheters.

The sleeve-type balloon 4 is formed of a thin elastic sheet material of the type used for conventional balloon angioplasty catheters, such as polyethylene or other polymer film for having a thickness of about 0.001 inches, or other thin flexible biocompatible material having thermal transfer properties, sufficient for the present purpose. In expanded condition the balloon has an outer cylindrical wall 4a, an inner cylindrical wall 4b, and top and bottom walls 4c and 4d, together defining an interior chamber. The central regions of each of the six scaffolding wires 5 pass through narrow passages 5a formed in the outer surface of the outer wall 4a of balloon 4, to couple the frame assembly 62 to the balloon 4 as seen in FIG. 1 and as noted above, the frame 5 can be stretched and collapsed by advancing the movable inner core 3 forward while the outer core catheter 8 is fixed thereby radially collapsing balloon 4.

The inner core catheter 3 has inflow and outflow fluid channels, formed in its wall extending from the proximal end of the catheter assembly to the distal end thereof. Inflow and outflow channels are fluidly connected at their distal ends to the interior chamber of balloon 4 by connecting inflow and outflow tubes 7 and 6 respectively. A pump or an infusion apparatus (not shown) is situated at the proximal end of the catheter assembly for circulating a thermal transfer fluid, such as a cold or hot saline liquid or gas (i.e. a fluid at a temperature sufficient to achieve the transition temperature of the stent), into the chamber of balloon 4 through inflow fluid channel and inflow tube 7 to fill the chamber, and then out from the balloon chamber through outflow tube 6 and outflow fluid channel. The term "fluid" is used herein in its broad sense and comprises both liquids and gases.

Figure 24A:
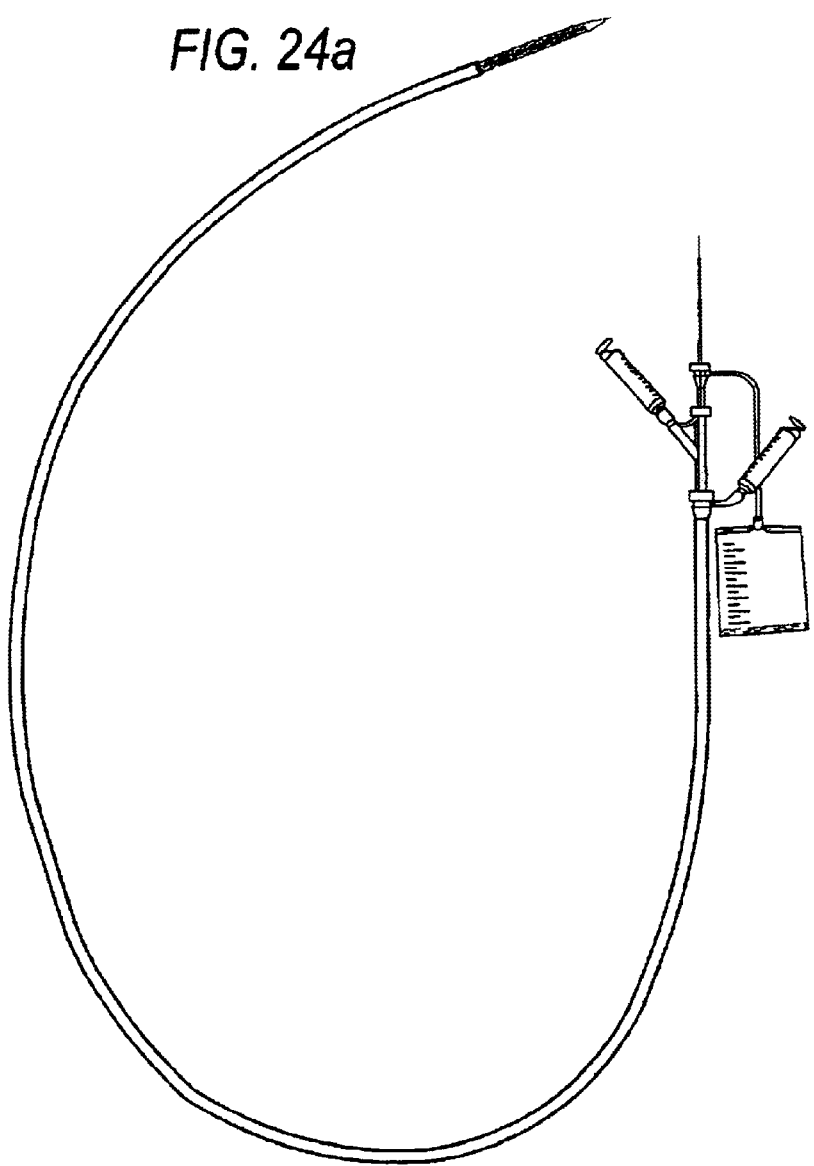
FIG. 24a is an elevation view of the entire third embodiment of the catheter assembly and associated sectored thermal transfer device.

Alternatively, the inflow channel can be connected to a pressurized canister filled with a gas or liquid, hereinafter referred to as a "thermal fluid", at a suitable temperature. Thermal fluid can also be injected by a syringe or by means of a pressure bag. Thermal fluid fills the balloon chamber and before this liquid or gas warms up inside the balloon, escapes into the outflow channel through outflow tube 6 and then to outside the patient at the other end of the system, where it may be collected in a bag (see FIG. 24a). This allows persistent local maintenance of a desired temperature of the outer wall 4a of balloon 4 which constitutes a thermal transfer wall of the thermal transfer device.

As seen in FIGS. 1–3, the stent-capturing device 70A comprises a plurality of resilient stent-capturing hooks 17 having hook portions 17a and shank portions 17b, molded into the wall of the stent capturing sheath 19 moveably situated over the outer core catheter 8. The hook portions 17A are normally spring biased outwardly to the positions shown in FIG. 1. The resilient portions of the hooks 17 can be at least partially covered with a thin membrane 95 to facilitate safe and accurate capturing and holding of the stents as described below. The stent-receiving sheath 11 in its retracted position as seen in FIGS. 1 and 2 has a flared end region 10. The hooks 17 can be opened or closed, i.e., the hook portions 17a moved radially outwardly or inwardly during deployment, retrieval or repositioning of an already deployed stent by advancing or withdrawing, respectively, the stent-receiving sheath 11 whereby the hook portions 17a are controllably engaged by the flared end region 10. Thus, the apparatus includes a stent capturing device including at least one elongate member 17 coupled to the catheter assembly 50A at its distal end region and having a free end portion 17a situated proximate to the balloon 4 for releasably holding a stent situated on the balloon during deployment, and for releasably grasping the stent during retrieval and repositioning.

Figure 11A:
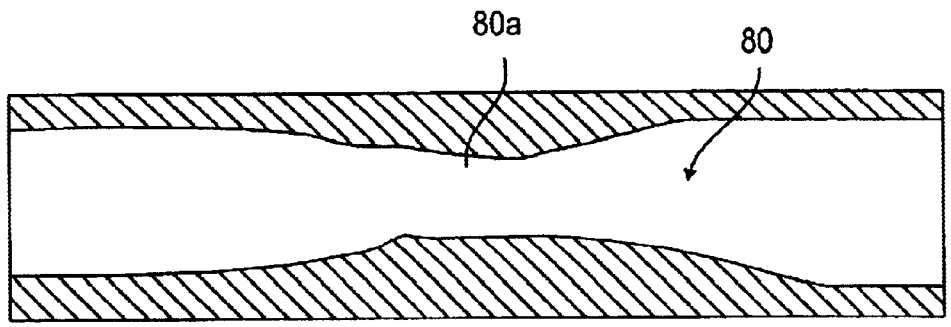
FIGS. 11(a)–11(g) are seven perspective views showing sequential steps of operation of the first and second versions of the second embodiment of the invention in connection with the deployment of the stent.
Figure 11B:
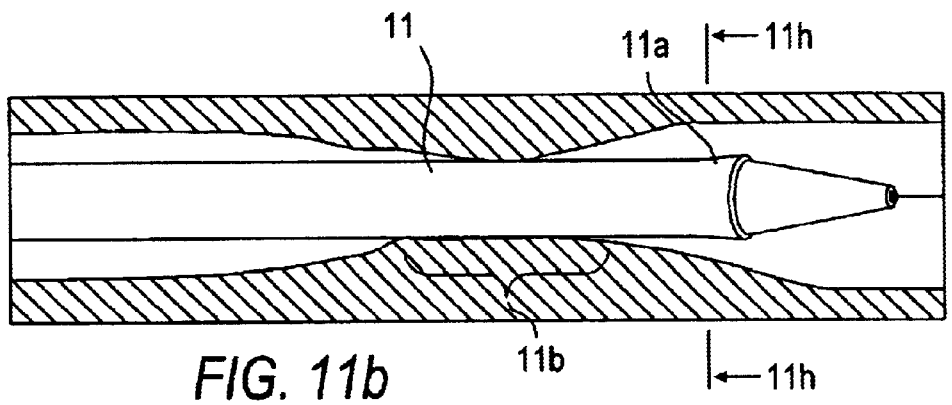
Figure 11C:
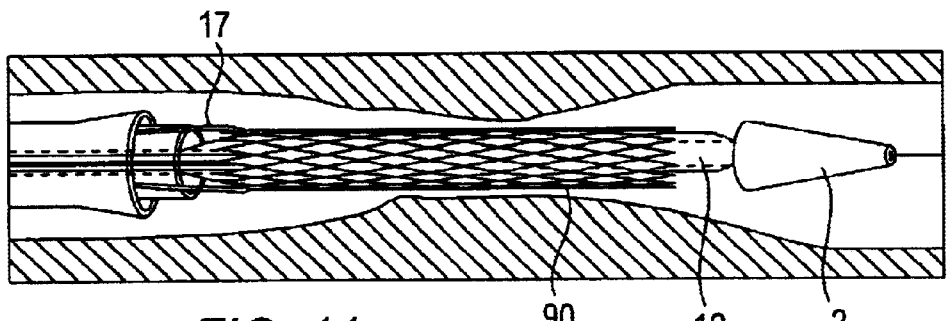
Figure 11D:
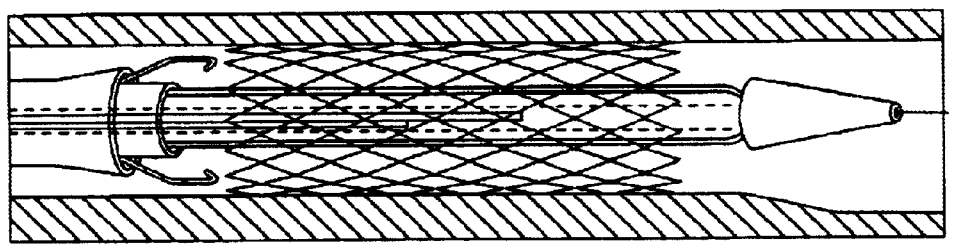
Figure 11E:
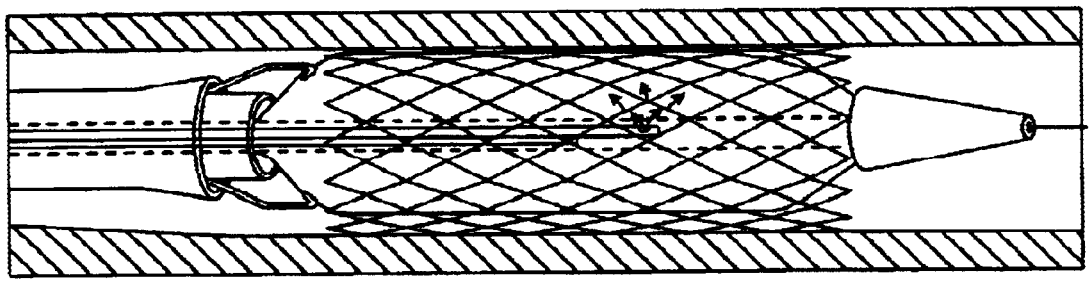
Figure 11F:
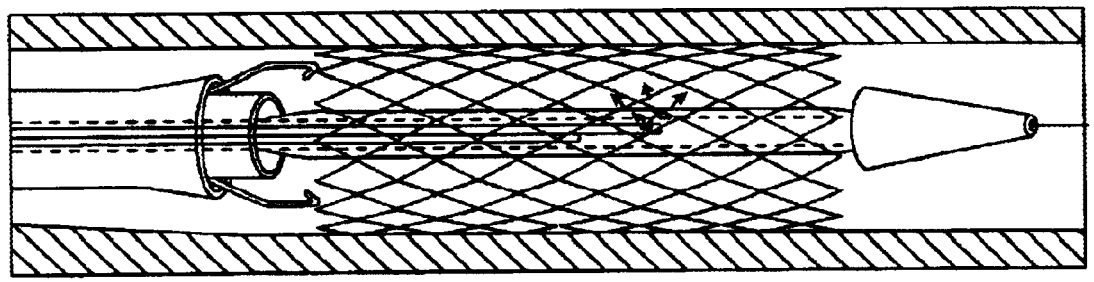
Figure 11G:
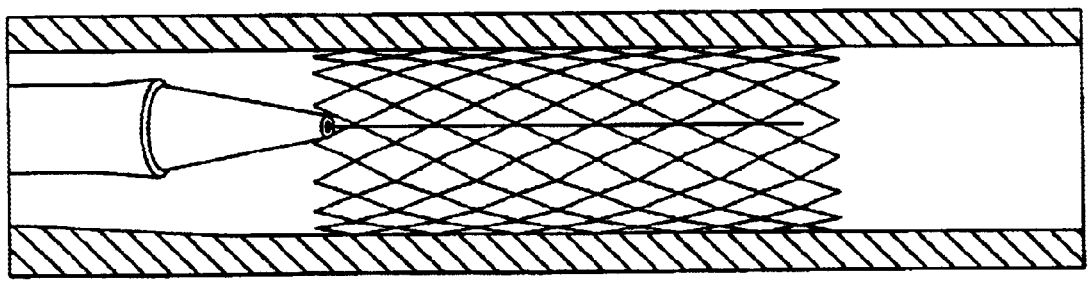
Figure 11H:
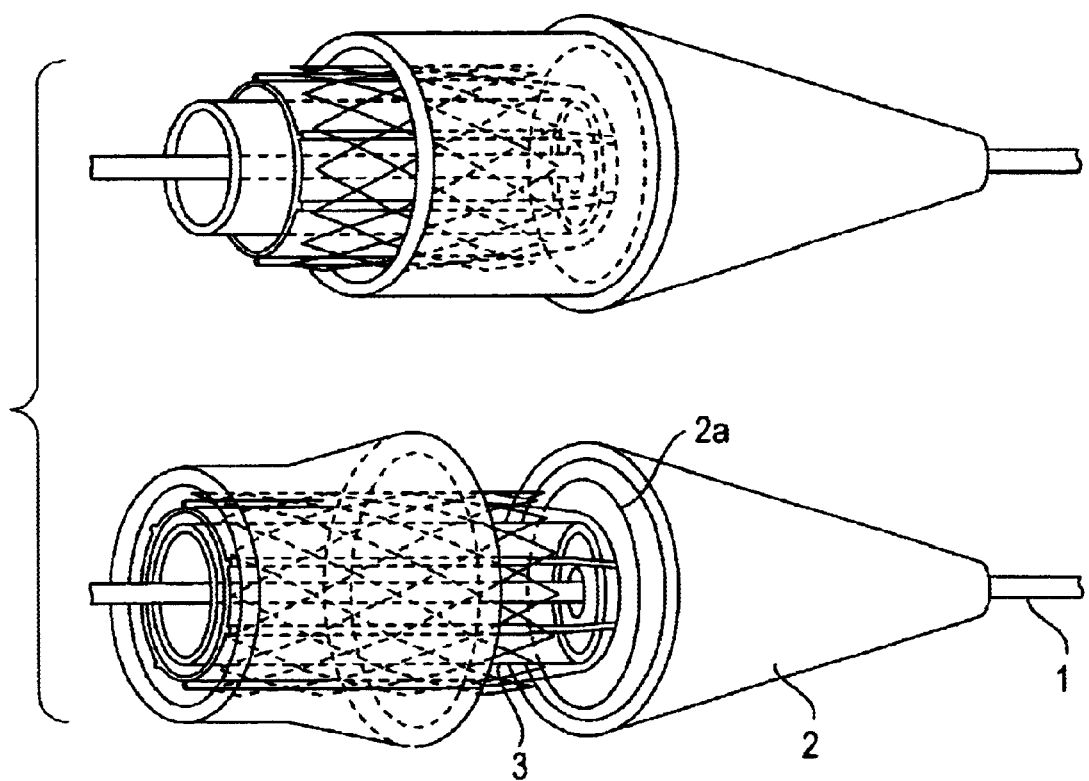
FIG. 11h shows two partial perspective views showing the sequence of withdrawal of the stent-receiving sheath from the conus.

As seen in FIGS. 11b and 11h, when the catheter assembly is introduced into the body, the end region of the stent-receiving sheath is in a closed condition in sealing engagement within a groove 2a formed in the conus 2. When the stent-receiving sheath is withdrawn to expose a preloaded stent or balloon, the tip assumes its flared configuration for facilitating the reception and subsequent removal of the collapsed stent (FIG. 11h).

As described below in connection with FIGS. 11 and 12, the system is introduced into the body with the frame assembly 62 and balloon 4 of thermal transfer device 60A in their collapsed condition and covered by the stent-receiving sheath 11. As seen in FIGS. 1–3 the inner core catheter 3 has a central lumen for receiving a guidewire 1 and two radio-paque markers 15 are provided on the moveable inner core catheter for precise positioning and operation under fluoroscopic guidance.

A first version of a second embodiment of the invention is illustrated in FIGS. 4–7. This embodiment is similar to the embodiment of FIGS. 1–3 in that it includes a catheter assembly 50B, a thermal transfer device 60B and a stent-capturing device 70B operationally connected thereto. The second embodiment differs from the first embodiment mainly in that the thermal transfer device 60B comprises a solid-type balloon 12 rather than the sleeve-type balloon 4 of the first embodiment. In other words, while a transverse cross-section of the sleeve-type balloon 4 is an annulus, the solid balloon has a circular disk-shaped transverse cross-section. The distal end of balloon 12 is sealingly connected to the introducing conus 2 or to the distal end of the inner core catheter 3, while the proximal end of balloon 12 is sealed to the more proximal aspect of the inner core catheter at 18 thereby defining a chamber. The balloon 12 is made of the same type of material as in the case of the first embodiment. The central region 12a of the balloon constitutes a thermal transfer wall as discussed below. Like the first embodiment, the thermal transfer device also includes a frame assembly 62A comprising a plurality of scaffolding wires 5, the distal ends of which are molded in the conus 2 fixed to the distal end of the inner core catheter 3, the proximal ends of which are molded to the outer core catheter 8, and central regions of which extend through passages 5a formed in the outer surface of the balloon 12.

The second embodiment of the invention shown in FIGS. 4–7 also incorporates apparatus for circulating a thermal transfer fluid into and from the interior chamber of balloon 12. While the inner moveable core 3 has a central lumen for the guidewire 1 in the same manner as in the first embodiment, two continuous channels 13 and 14 are provided in the inner core 3. Channels 13 and 14 extend from the proximal end of the inner core catheter 3 and open at respective ports 13a and 14a situated within the chamber of balloon 12. Channel 14 is used for infusion of a thermal fluid into the chamber of balloon 12 while channel 13 is used as an outflow channel. By suitably connecting the proximal end of channel 14 to a pump, or other source of infusion of thermal fluid, and by suitably connecting the proximal end of channel 13 to a collecting container, a constant circulation of the thermal transfer fluid through the balloon 12 is achieved. Alternatively, the thermal fluid can recirculate through a closed circuit pump system. Inflow channel 14 and outflow channel 13 can be interchanged so that channel 14 is used for outflow while channel 13 is used for inflow.

Figure 7:
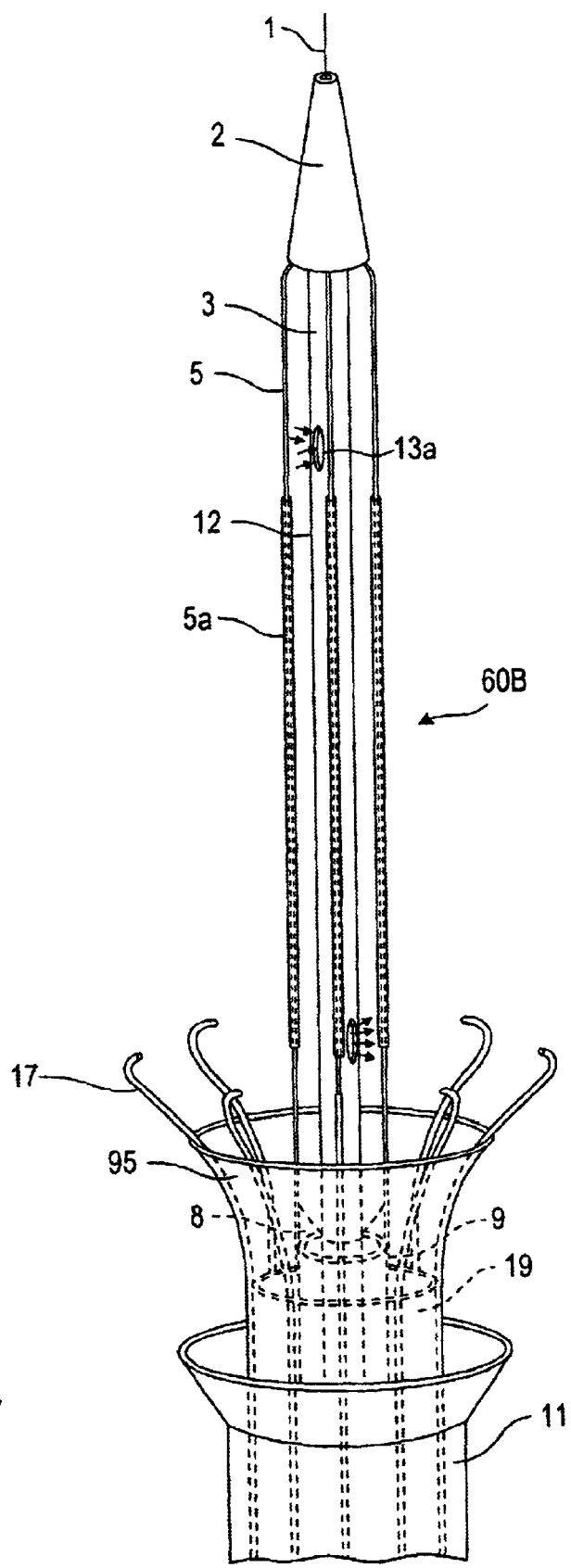
FIG. 7 is a perspective view of the second embodiment with the thermal transfer device in a collapsed condition.

Referring to FIG. 7, as described below in connection with FIGS. 11 and 12, the thermal transfer device 60B can be collapsed in the same manner as thermal transfer device 60A by advancing the moveable core catheter 3 forwardly while holding the outer core 8 fixed. Alternatively, the thermal transfer device 60B can be collapsed by fixing the inner core catheter 3 in place and withdrawing the outer core catheter 8. The stent-capturing device 70B essentially corresponds to the stent-capturing device 70A.

Figure 8:
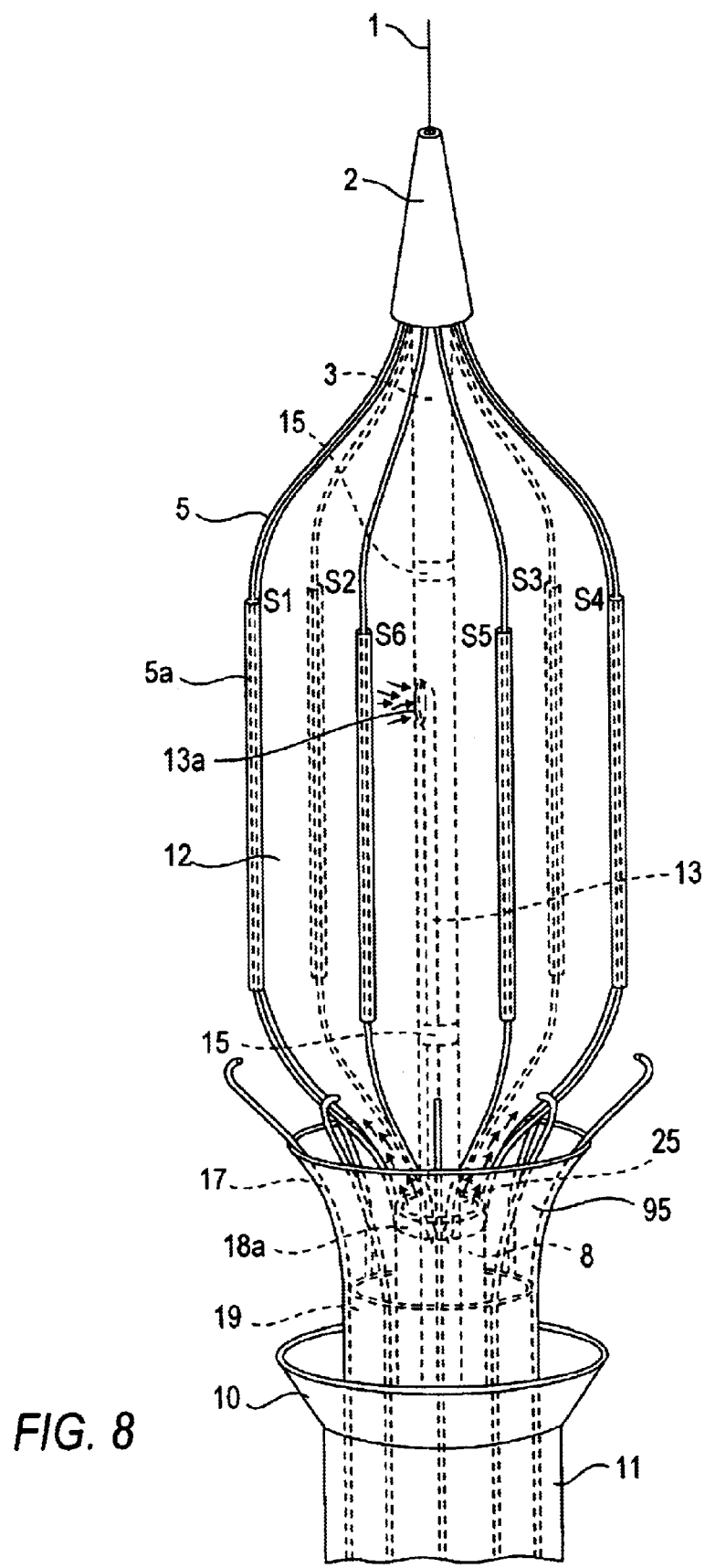
FIG. 8 is a perspective view of a second version of the second embodiment, with a second version of the thermal transfer fluid circulating arrangement.
Figure 9:
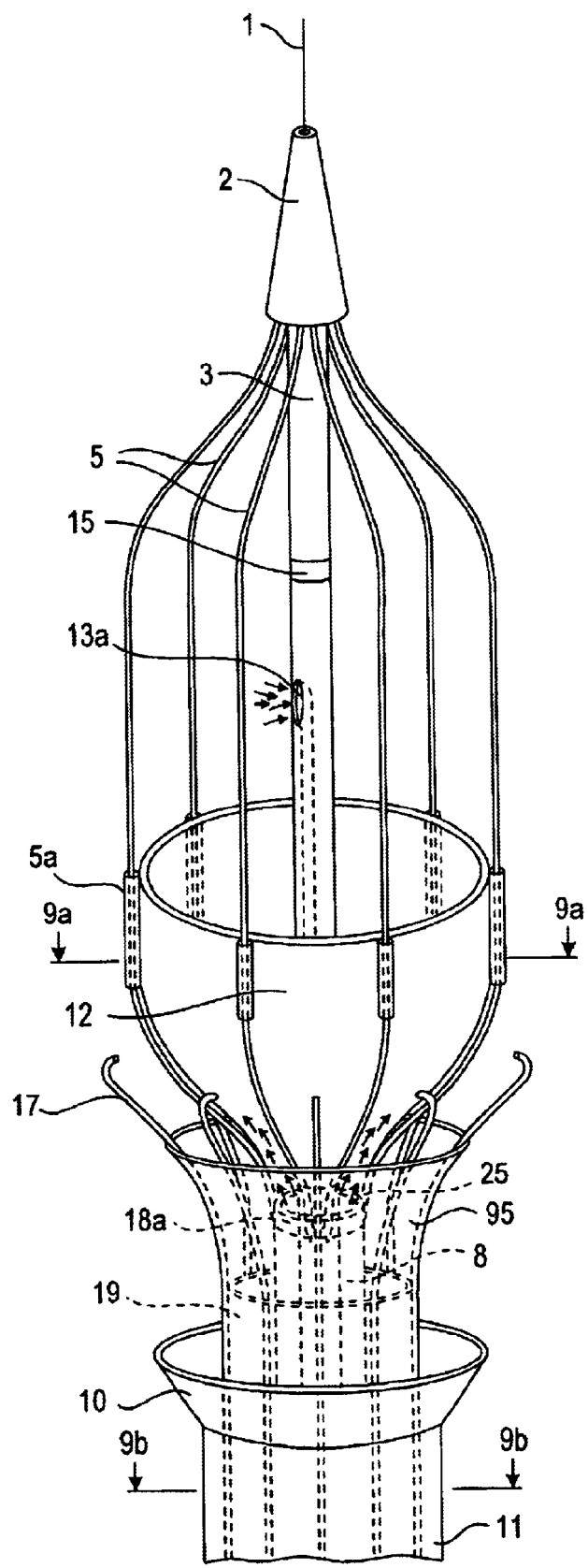
FIG. 9 is a perspective view of the second version of the second embodiment, partially broken away to show the second version of the circulation arrangement.
Figure 9A:
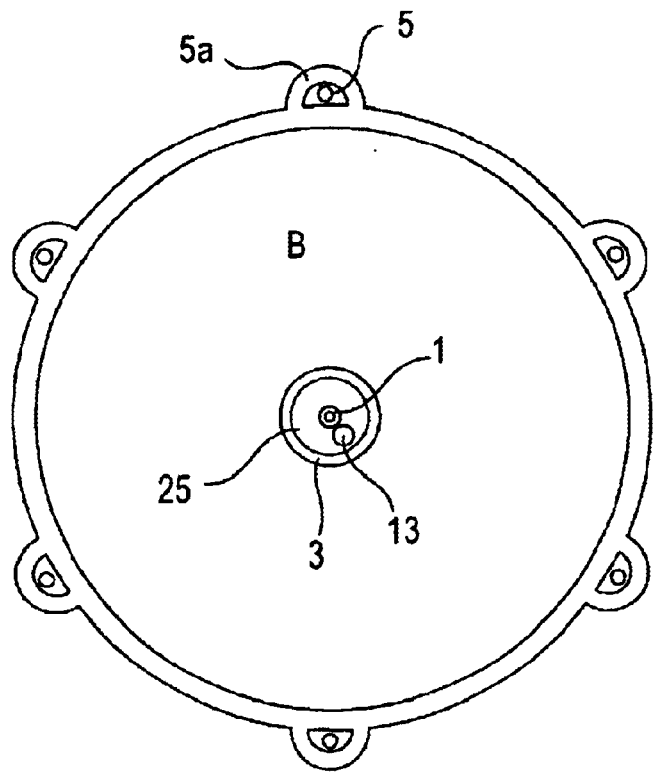
FIG. 9a is a section view taken along line A—A of FIG. 9.
Figure 9B:
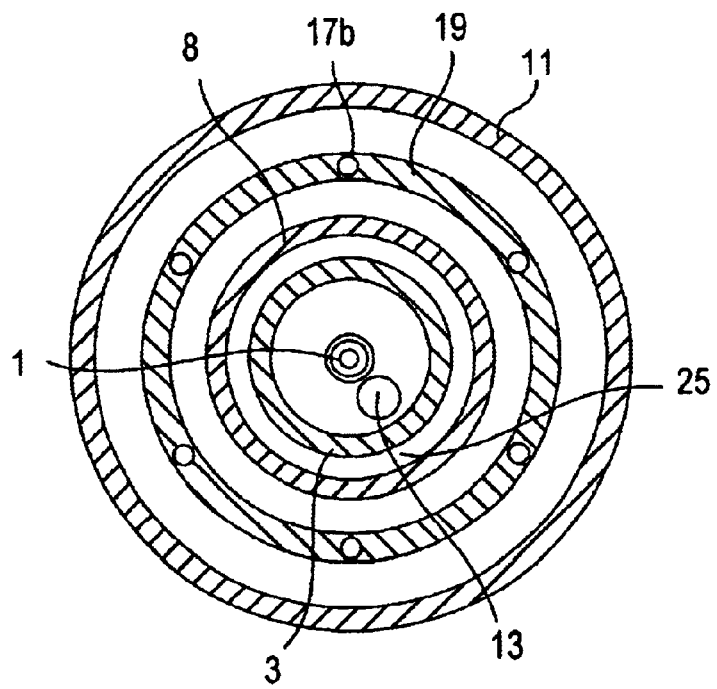
FIG. 9b is a section view taken along line B—B of FIG. 9.
Figure 10:
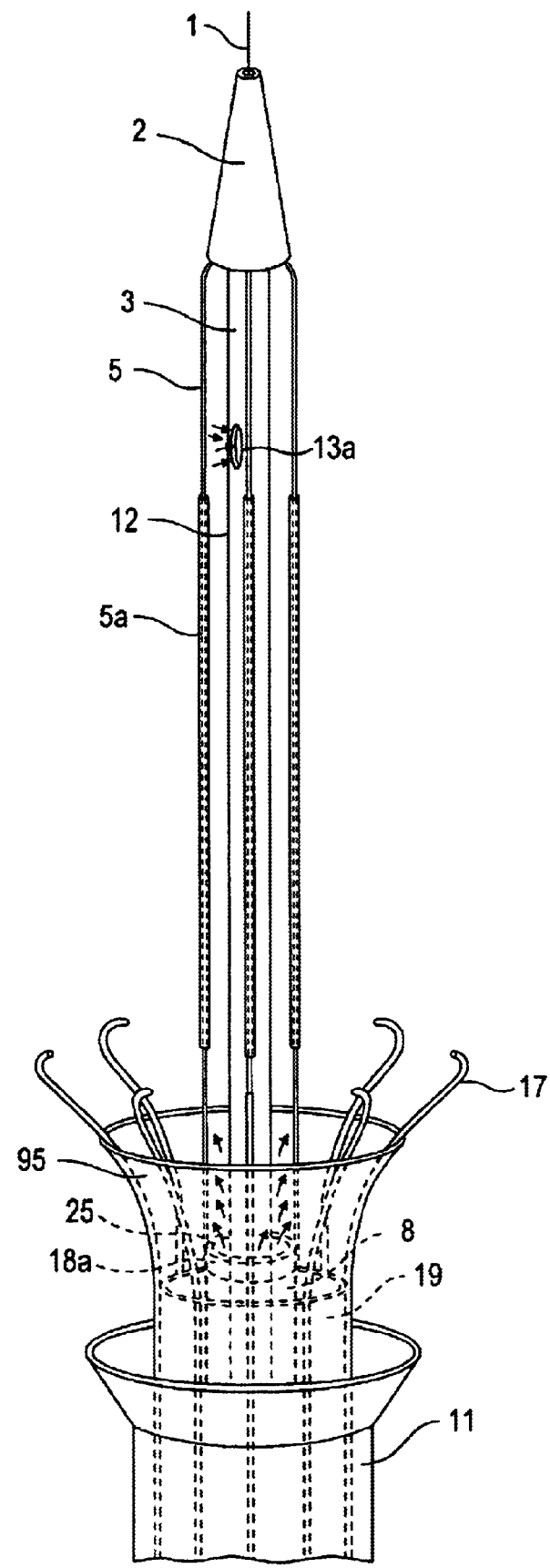
FIG. 10 is a perspective view of the second version of the second embodiment, with the thermal transfer device shown in a collapsed condition.

A second version of the second (solid balloon) embodiment is illustrated in FIGS. 8, 9 and 10. This version essentially differs from the first version of the second embodiment in the construction of the thermal transfer fluid circulation system. The proximal end of balloon 12 is sealingly attached to the outer core catheter 8 at 18a and the space between the outer core catheter 8 and the inner movable core catheter 3 functions as an inflow channel for thermal fluid 25 which opens into the chamber defined by balloon 12. An outflow channel 13 is formed in inner core catheter 3 which terminates at a port 13a communicating with the balloon chamber. In this manner, one of the two channels in the inner core catheter 3 required in the first version of the second embodiment can be eliminated.

Figure 8A:
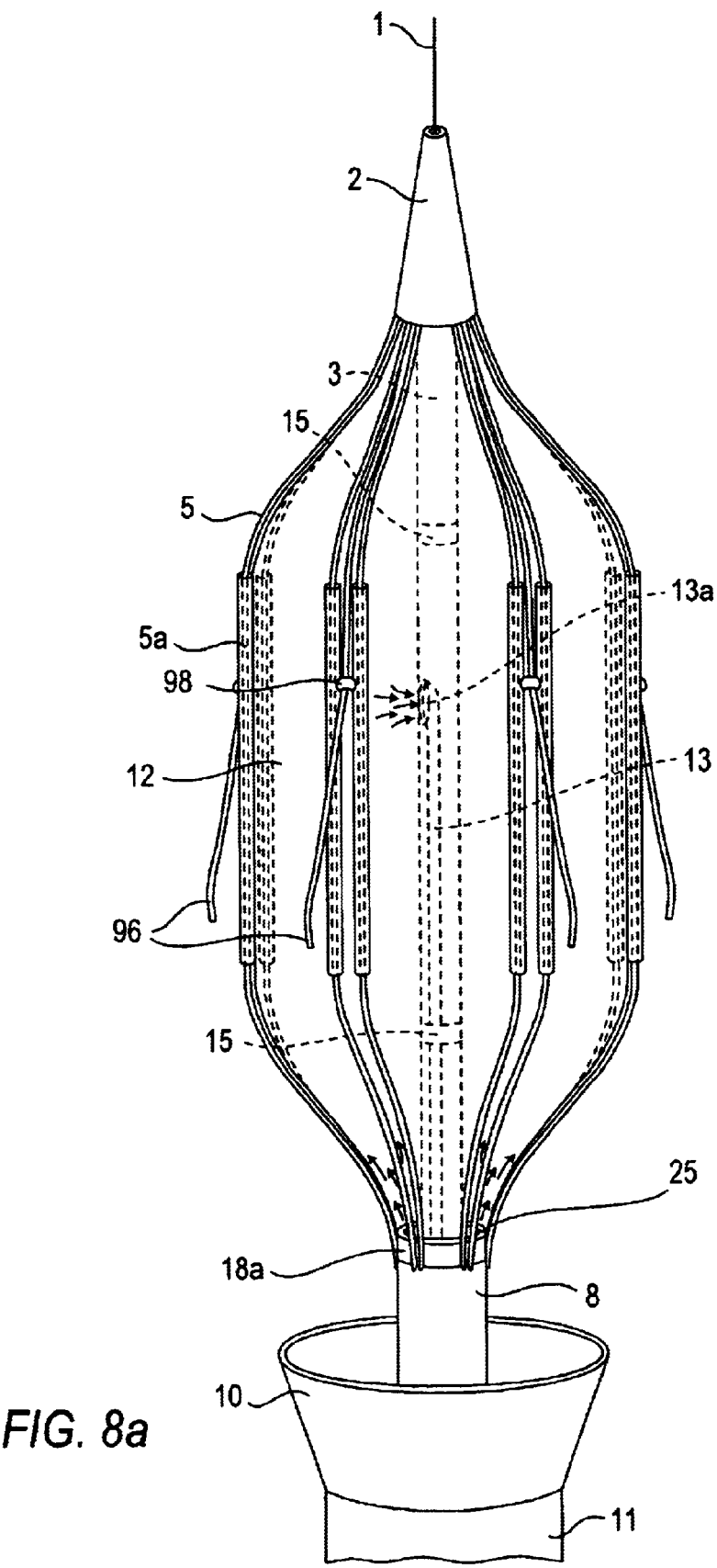
FIG. 8a is perspective view of another version of the second embodiment, with a second version of a stent-capturing device.

A modification of the second version of the second embodiment is shown in FIG. 8a, where the frame wires 5 are paired and interconnected with a single bridging bar 98 in their central portions. The stent-capturing sheath 19 with the capturing hooks are eliminated in this modification. Instead, there are at least four capturing wires 96, which are molded to the inner core catheter 3 at the base of conus 2. The capturing wires 96 extend parallel to the frame wires 5, but outside the balloon 12 and pass under the bridging bars 98 between the central portions of the paired frame wires 5. The relative motion of the movable core 3 and the outer core catheter 8 promotes opening and closing of the capturing wires 96. When the balloon 12 is expanded, capturing wires 96 open with it. When the balloon is slowly deflated, the capturing wires 96 stay open and do not follow the collapsing balloon until the angled portion of the capturing wires become engaged with the bridging bars 98, which will facilitate closing of the capturing wires over the balloon.

Figure 8B:
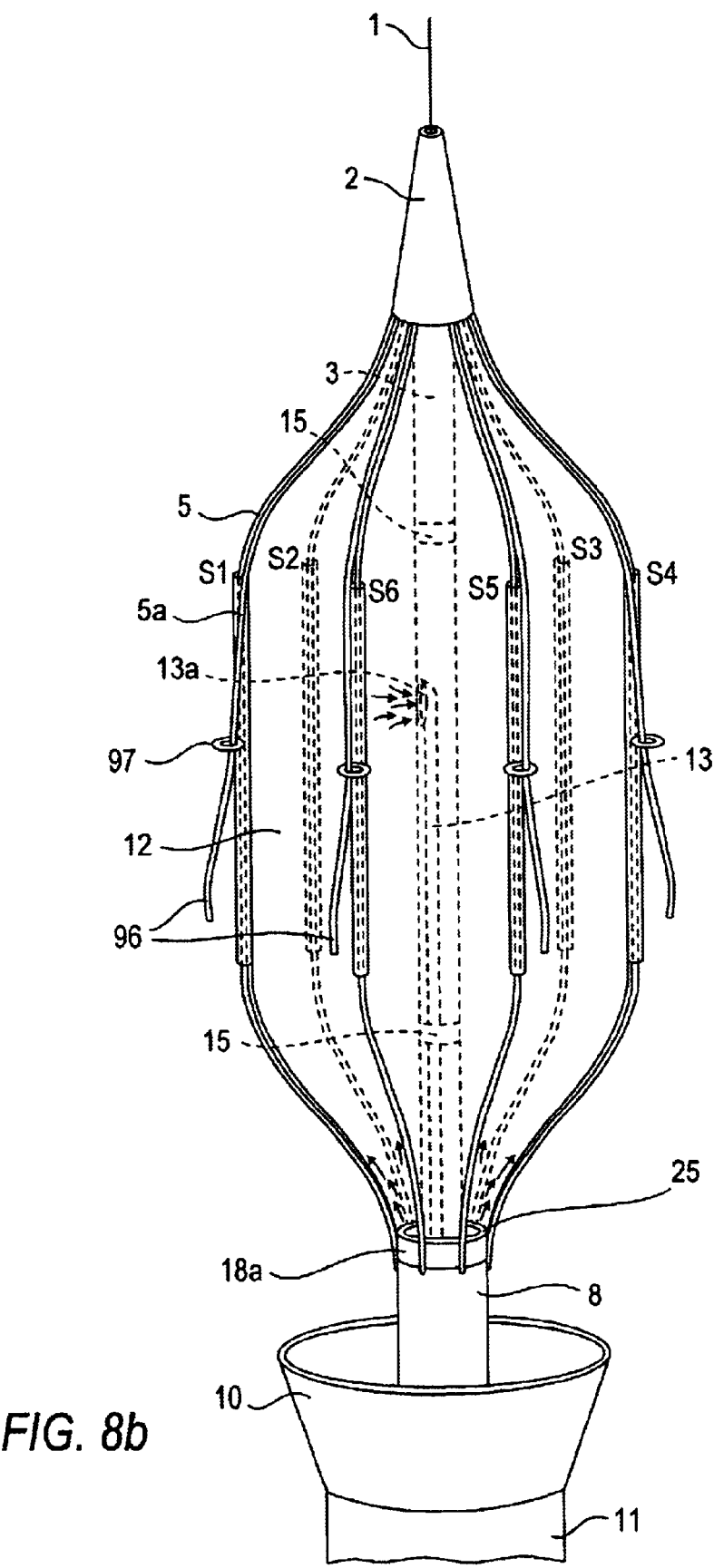
FIG. 8b is a perspective view of still another version of the second embodiment, with a third version of a stent-capturing device.

FIG. 8b demonstrates another modification of the second version of the second embodiment. The balloon and frame are similar to the second version of the second embodiment, but the stent-capturing mechanism consists of four capturing wires 96 which are molded to the inner core catheter at the base of the conus 2. The capturing wires 96 extend parallel to the frame wires 5, but outside the balloon 12 and pass through the rings 97 attached to the central portions of the frame wires 5. The mechanism of opening and closing of the capturing wires 96 is similar to the one described in FIG. 8a with the only difference that the capturing wires 96 pass through the rings 97 on the frame instead of extending under the bridging bars 98 between the parallel paired wires in FIG. 8a.

Figure 8C:
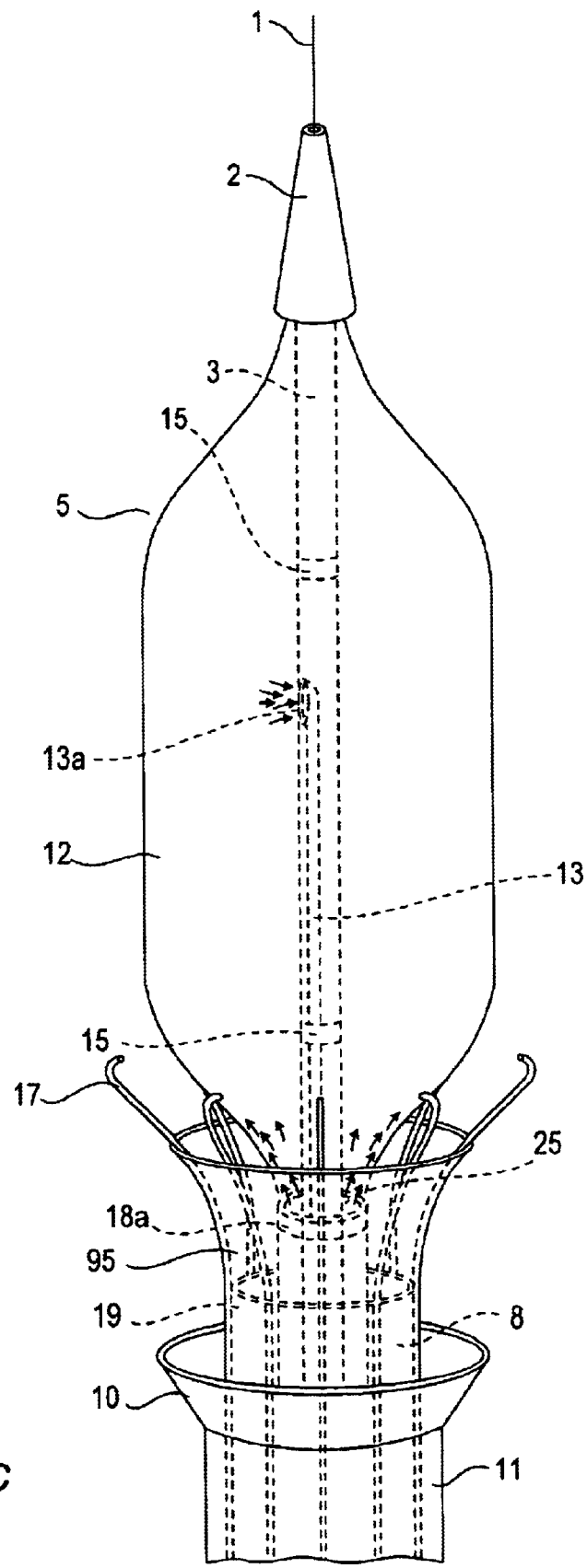
FIG. 8c is a perspective view of yet another version of the second embodiment which does not utilize a frame assembly.

Yet another modification of the second version of the second embodiment is illustrated in FIG. 8c, where the solid type balloon does not have any metallic frame, but has an inflow channel 25 and an outflow channel 13, and can be expanded and collapsed by relative motion of the inner movable core 3 along the outer core catheter 8 in conjunction with injection of the thermal fluid under pressure.

Figure 9C:
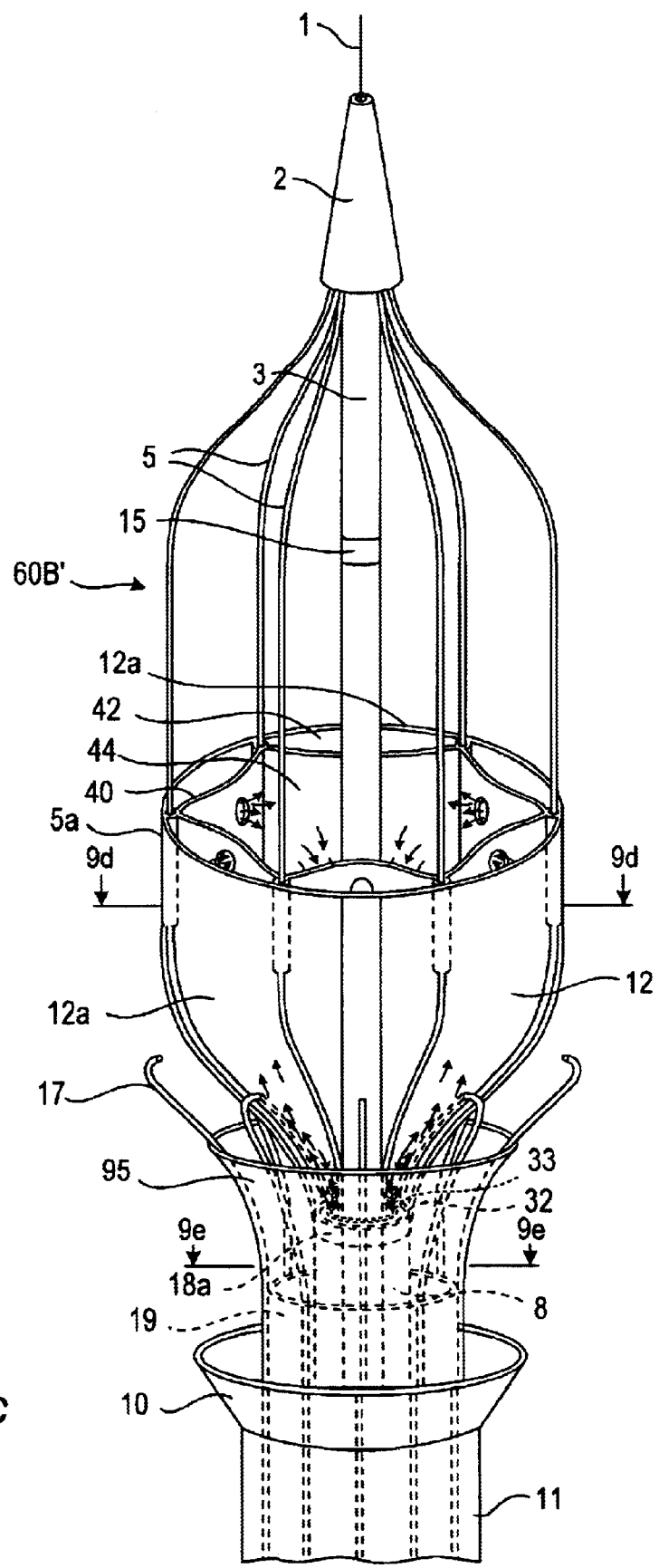
FIG. 9c is a perspective view of a modification of the second version of the second embodiment, but partially broken away to show the modification of the second version of the circulation arrangement.
Figure 9D:
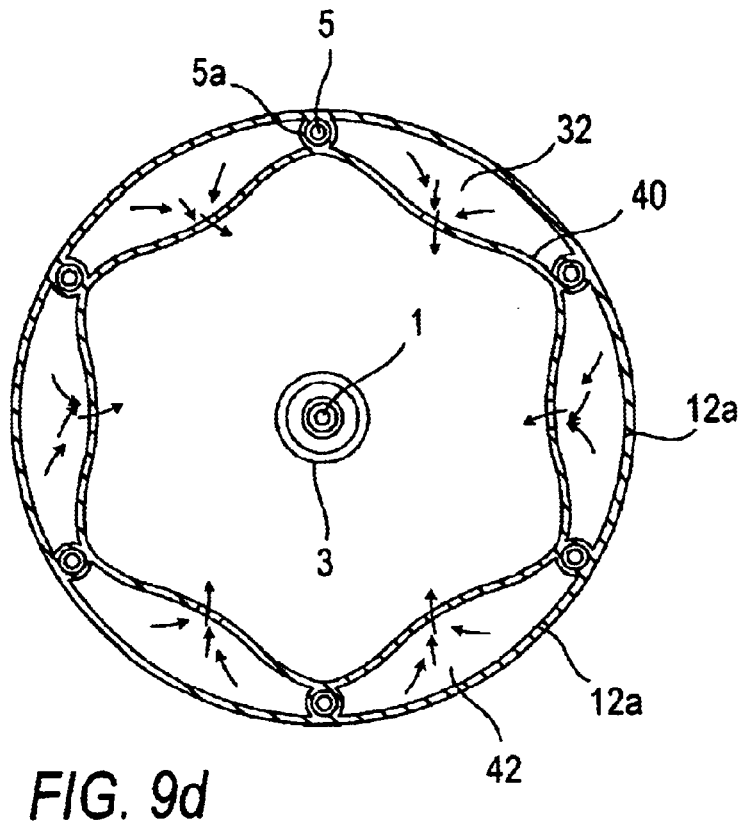
FIG. 9d is a section view taken along line D—D of FIG. 9c.
Figure 9E:
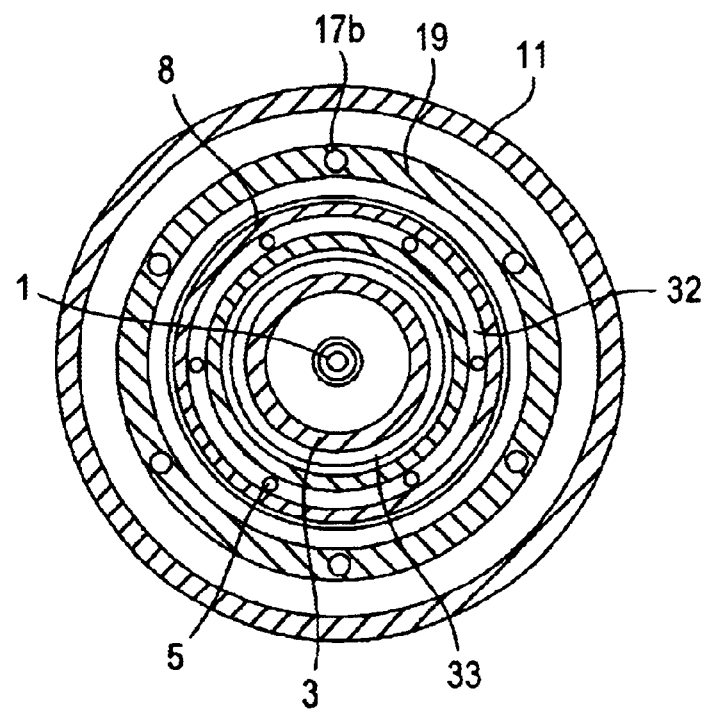
FIG. 9e is a section view taken along line E—E of FIG. 9c.

Referring to FIGS. 9c–9e, a modification of the second solid balloon embodiment of the invention is illustrated. In this embodiment, the thermal transfer device 60B comprises a balloon 12 having an outer wall 12a and an inner wall 40 attached to the inner surface of the outer wall 12a of the balloon at equally spaced locations, preferably at the wire sleeves 5a receiving the frame wires 5, as best seen in FIG. 9d. The inner wall 40 and outer wall 12a of the balloon define an outer chamber 42 between them while the inner wall 40 defines an inner chamber 44. The inflow of a thermal fluid into the outer chamber 42 is provided through channel 32. There are multiple perforations in the inner wall 40 of the balloon, and the thermal fluid escapes into the inner chamber 44 of the balloon after being transiently trapped between the inner and outer layers of the balloon for more efficient thermal transfer through the outer balloon wall 12a. The thermal fluid then escapes into the space between the outer core catheter 8 and the movable core catheter 33 and is collected into an attached bag at the proximal end of the catheter assembly outside the patient. All other components of the system and mechanisms of its delivery/retrieval and operation remain the same as described above in the embodiments of FIGS. 4, 5, 6 and 7.

The systems comprising the sleeve type balloon (FIGS. 1–3) and the solid type balloons (FIGS. 4–10), provided with the stent-capturing hooks 17, are beneficial for primary delivery, repositioning or removal of stents including stent-graft devices or covered/coated stents.

Referring to FIG. 11, a clinical scenario of primary stent delivery and deployment into a focal narrowing 80a of a vessel 80 is shown in stages. The stent is formed in accordance with the apparatus of the invention of either a one-way or two-way shape memory alloy having a first transition temperature at or below the body temperature. In utilizing the apparatus described above for primary stent delivery, a stent is initially mounted on the thermal transfer device in its collapsed condition and so that the stent is in thermal transfer relationship with the collapsed thermal transfer device. Preferably, the system is provided to the operator in a closed configuration (seen in FIG. 11b) in which the stent-receiving sheath 11 is in a forward position covering the collapsed stent 90, which has already been preloaded or mounted (such as by crimping) in contacting engagement over the collapsed balloon 12 and with the stent capturing hooks 17 secured to it. In the closed configuration, the distal end 11a of the stent-receiving sheath 11 is received in a groove 2a of conus 2 to seal the space within sheath 11 from the entry of blood or other body fluids in vessel 80 during delivery.

The system is introduced into the vessel and positioned under direct fluoroscopic guidance (with the assistance of positioning markers 15) such that the position 11b of the delivery system with the premounted stent 90 is situated in the area of narrowing 80a of vessel 80 (FIG. 11b). During this delivery, the stent-receiving sheath 11 at least partially thermally insulates the collapsed stent 90 from body heat thereby maintaining the temperature of the stent 90 below body temperature.

Figure 24B:
FIG. 24b is a perspective view of the third embodiment of the invention with a stent pre-mounted on the collapsed thermal transfer device.

Referring to FIG. 11c, deployment of stent 90 begins when the operator retracts or withdraws the stent-receiving sheath 11 exposing the collapsed stent 90 mounted on the collapsed balloon 12 to the vessel interior and to body heat (see FIG. 24b). The circulation of a cold liquid or gas through the chamber of balloon 12 is started at about the same time as the sheath 11 is withdrawn. For example a cool saline solution is infused from the proximal end of the catheter assembly 50A through inflow channel 14 into the balloon chamber through port 14a and recirculates back through port 13a and outflow channel 13. The temperature of the stent 90 is thereby maintained below the transition temperature preventing premature expansion of the stent by the local transfer of thermal energy through the wall of the balloon 12 into the thermal transfer fluid. The balloon 12 remains in its collapsed position at this time by maintaining the outflow channel 13 open. A precise positioning of stent 90 is enabled by controlling the expansion of stent 90 through the circulation of cooling thermal fluid even after the sheath 11 is retracted and the stent is exposed to body temperature. When the operator is satisfied that the stent 90 is precisely positioned in the desired location 80a of the focal narrowing of vessel 80, the stent-capturing hooks 17 are opened and disconnected from stent 90 by further withdrawing of the stent-receiving sheath 11 with respect to the stent-capturing sheath 19, and the infusion of the cooling thermal fluid is stopped. The opened hooks are withdrawn toward the stent-receiving sheath before the stent expands to avoid interference with the stent as it expands. The stent 90 then warms naturally to body temperature through contact with surrounding blood or other body fluids or gas, and expands towards its original predetermined shape (FIG. 11d). The stent is thus deployed into supporting engagement with the wall of vessel 80 and exerts an outward force against the wall to open the focal narrowing 80a of vessel 80.

Balloon angioplasty of the deployed stent can then be performed if clinically indicated. This can be achieved by closing the outflow channel 13 with a provided stop-cock. The balloon is expanded by expansion of the frame assembly 62 and infusion of a contrast material diluted in normal saline through the infusion port 14a, which allows visualization of the balloon under real time radiological control (FIG. 11e). Opening the frame assembly 62 is achieved by moving the outer core catheter 8 forward relative to inner core catheter 3 which helps expansion of the balloon 12. High pressure can be achieved inside the balloon 12, which is regulated and controlled by a pressure manometer connected to the inflow channel outside the patient. Angioplasty (FIG. 11e) can be performed sequentially several times if so desired clinically.

The balloon 12 is then deflated by opening the outflow channel 13 and the frame assembly 62 collapsed by moving the outer catheter 8 back (FIG. 11f). The collapsed balloon is then withdrawn back into the stent-receiving sheath 11 whereupon the system can be removed from the body, leaving the stent in place (FIG. 11g). As noted above, this system can be used for deployment of stents exhibiting one-way or two-way memory.

The same system can be used for delivery and precise positioning of stents which are formed of shape-memory alloys that have a transition temperature greater than body temperature and which therefore expand to their predetermined configurations at temperatures higher than body temperature. Such a stent is delivered in the area of interest in the collapsed state covered with the outer sheath 11 and then exposed by moving the sheath 11 backwards. No infusion of cold thermal transfer fluid is needed to keep the stent in its collapsed state since the temperature of the stent will only rise to body temperature which is below the transition temperature. The stent therefore remains mounted on the collapsed balloon 12 secured to the catheter assembly by stent-capturing hooks. When the position of the device is adjusted and the desired location of the stent is confirmed, the stent-capturing hooks 17 are opened by further withdrawing of the stent-receiving sheath 11, releasing the stent 90 and the infusion of a warm solution at least at the transition temperature which is higher than body temperature is started through the inflow channel 14. The frame assembly 62 is opened by moving the outer core catheter 8 forward. These maneuvers allow expansion of the mounted stent inside the area of stenosis providing high radial force on the walls of the vessel due to its heating to the transformation or transition temperature. If clinically indicated a primary stent placement can be supplemented with a balloon angioplasty with the help of the same delivery system. This can be achieved by closing the outflow channel and infusion of a diluted contrast material through the inflow channel in the manner described above.

Referring to FIG. 12, a clinical scenario is given when the stent 90 has been malpositioned inside the vessel only partially covering the area of stenosis (FIG. 12a) and it is desired to reposition the stent. In this case, the stent 90 is formed of a two-way shape memory alloy. For example, the alloy may have a first transition temperature equal to or below body temperature, and a second lower transition temperature in the range of between −10° C. to +35° C. The system is introduced with the balloon 12 in a collapsed state and covered with the stent-receiving outer sheath 11 (FIG. 12b) and positioned at the desired location such that the collapsed balloon 12 is situated within the lumen of stent 90 that is intended to be retrieved or repositioned. The outer sheath 11 is withdrawn, the distal end 11a obtaining a flared configuration, thereby exposing the frame assembly 62A and the collapsed balloon 12 (FIG. 12c). The metallic frame assembly is opened and the outer core catheter 8 advanced while the movable inner core catheter 3 is fixed in place (FIG. 12d). Expansion of the frame assembly 62A brings the outer wall of balloon 12 into close contact with the stent. At this time the infusion of a cold thermal fluid into the chamber of balloon 12 is started through the inflow channel 14 and the balloon 12 is inflated without creating high internal pressure within it due to an open outflow channel 13. The diameter of the open wire frame 62A matches the internal diameter of the stent and the cold balloon 12 moves into direct contact with the stent, causing its local cooling to the temperature at or below the second transition temperature, e.g. in the range of −10° C. to 35° C., through the thermal transfer wall forming balloon 12. The stent becomes soft and pliable at this temperature and reduces at least somewhat in diameter to separate from the wall of vessel 80. The next step includes slowly stretching the wire frame 62 to a smaller diameter by moving the outer core catheter 8 backwards and keeping the movable core catheter 3 of the system in the same position. Start this maneuver causes a slow collapse of the frame assembly (FIG. 12e).

Figure 12A:
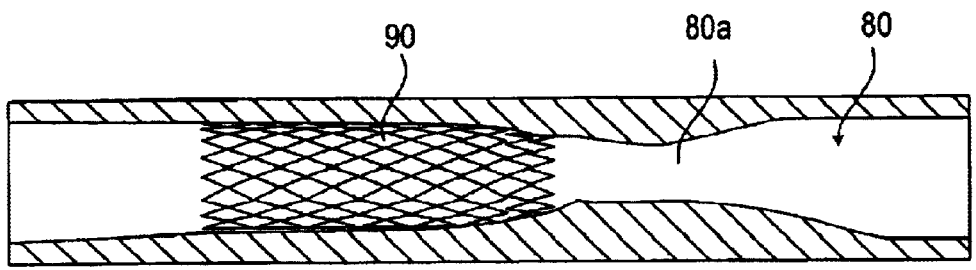
FIGS. 12(a)–12(l) are twelve perspective views showing sequential steps of operation of the first and second versions of the second embodiment of the invention in connection with repositioning and/or retrieving an already positioned stent.
Figure 12B:
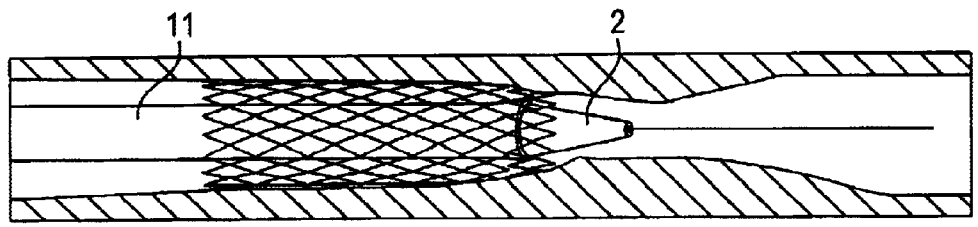
Figure 12C:
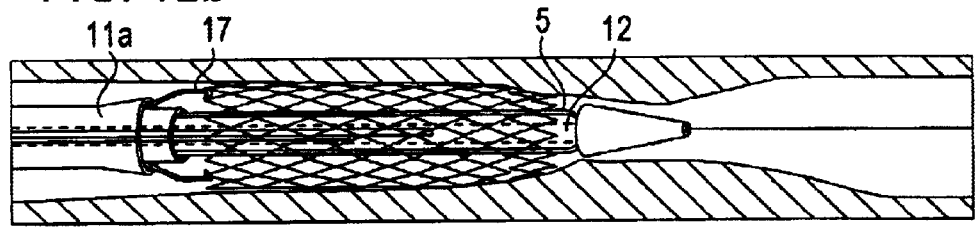
Figure 12D:
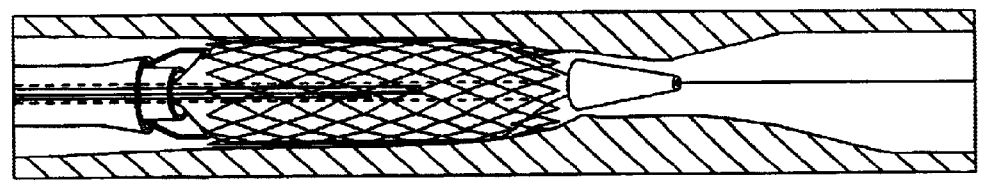
Figure 12E:
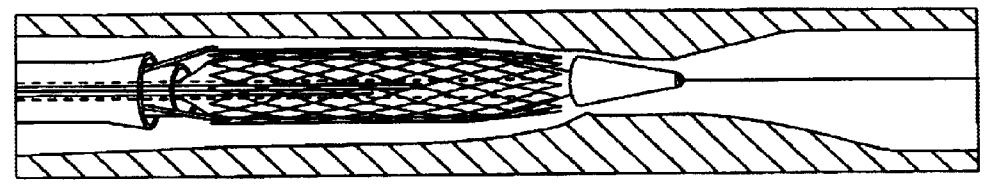
Figure 12F:
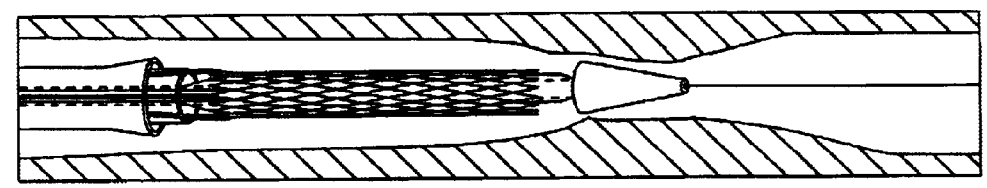
Figure 12G:
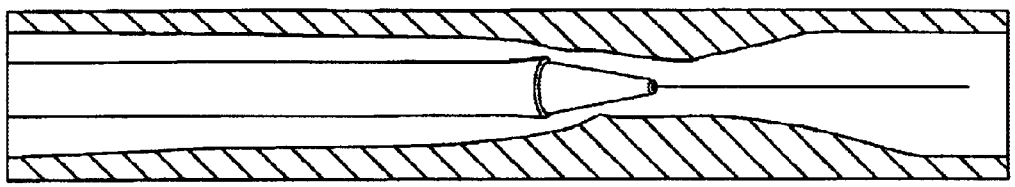

The infusion of cold thermal transfer fluid continues, but the balloon 12 moves away from the wall of the vessel 80 or other tubular structure due to stretching of the wire frame. The stent, or its proximal end in the case where the stent is designed to operate as such, begins to collapse inwardly "hugging" the outer wall of balloon 12 and the frame. At this time the stent-capturing hooks 17 are maneuvered to close over the collapsed proximal end of the stent by suitable manipulation of the stent-capturing sheath 19 (FIG. 12f). This causes secure fixation of the softened cooled stent to the catheter assembly. The stent is then drawn into the stent-receiving sheath 11 with a flared tip 11a and infusion of the cold solution/gas into the balloon 12 is terminated (FIG. 12g). Collapse of the proximal end of the stent prevents migration of the device and slippage over the balloon due to persistent contact of the distal two thirds of the stent with the vessel wall, even though the entire stent becomes very soft.

Figure 12H:
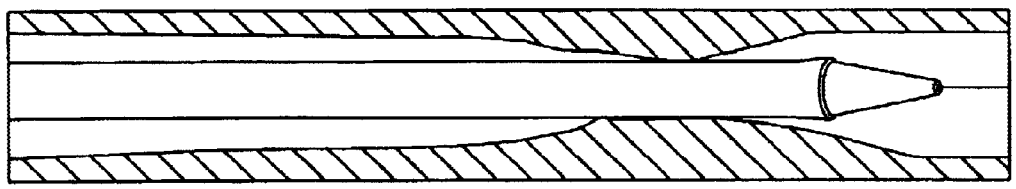
Figure 12I:
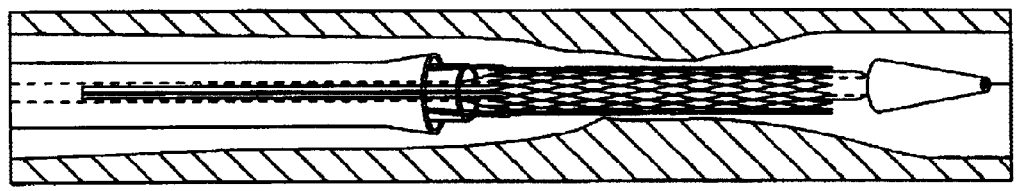
Figure 12J:
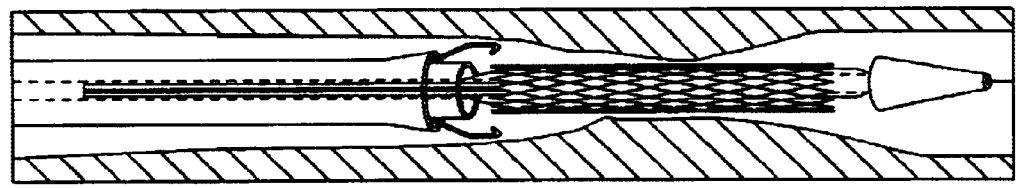
Figure 12K:
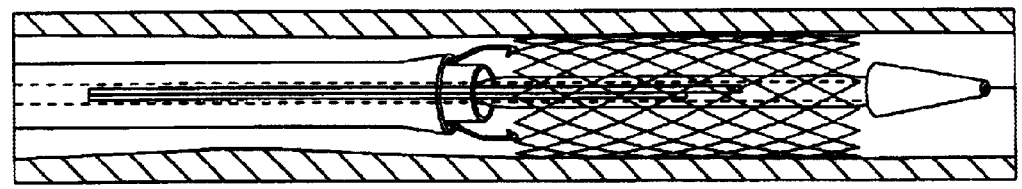
Figure 12L:
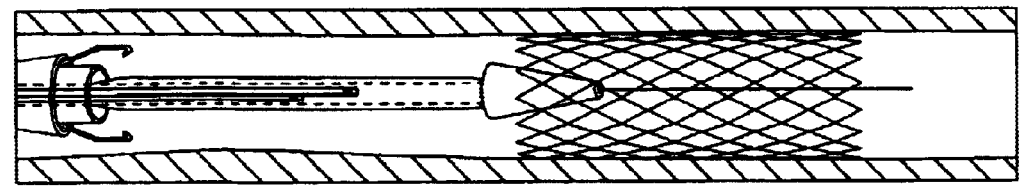
Figure 13:
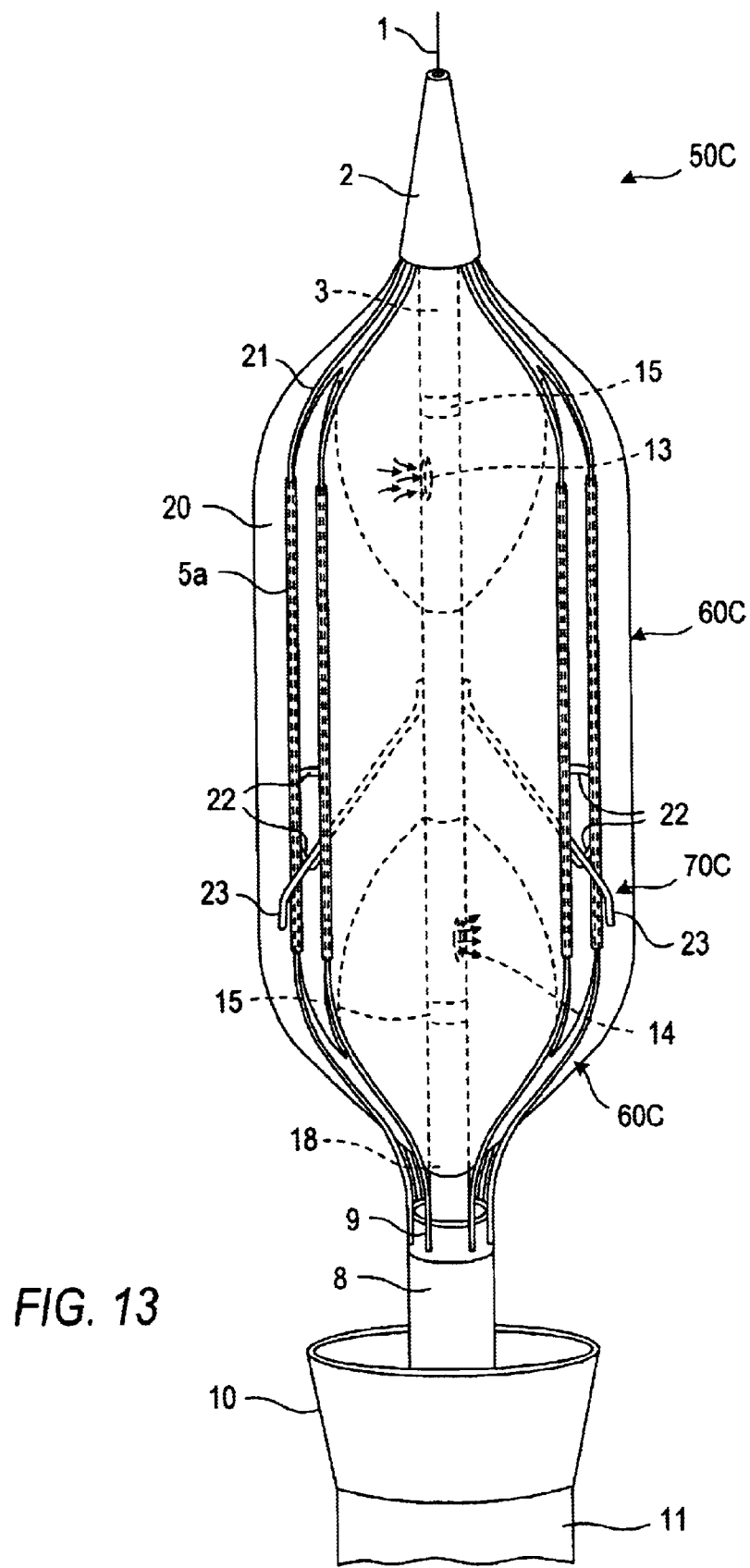
FIG. 13 is a perspective view of a first version of a third embodiment of a catheter assembly, including another version of a stent capturing device, and associated sectored thermal transfer device in its expanded position in accordance with the invention, with the first version of a thermal transfer fluid circulation arrangement.

The stent can be then completely removed from the body or repositioned while inside the stent-receiving sheath 11 into the proper location (FIG. 12h). In this latter case, the stent is then unsheathed (FIG. 12i), warms to body temperature and then expands into the original shape and diameter after the stent-capturing hooks are released (FIG. 12j and FIG. 12k). The reposition and retrieval system is then removed from the body and the repositioned stent remains in place (FIG. 12l). Stent retrieval is beneficial in patients where the indication for primary stent placement is an acute intimal dissection, where the stents are used as the vehicle for local delivery of medications or radioactive substances, or in the situations when repositioning of misplaced stent is required.

The same system can be used for retrieval or repositioning of a stent made from two-way shape memory alloy having a first transition temperature greater than body temperature and therefore a stent expanding to its original shape at higher than body temperature. These stents require cooling to a temperature below 37° C. in order to exhibit second way memory and partially collapse for safe retrieval, with all other steps similar to the ones described in connection with FIG. 12. If repositioning of such a stent is required after it has been recovered into the outer sheath, the position of the closed system is adjusted under direct fluoroscopic guidance. The mounted captured stent is unsheathed and stays in the collapsed state without infusion of a cold solution since the first transition temperature is greater than body temperature. After the stent is precisely positioned at the desired location, the stent-capturing hooks are opened by completely withdrawing the stent-receiving sheath 11, releasing the stent. A warm solution is infused into the balloon chamber through the infusion port 14a and the metallic frame 62 is opened by moving the outer core catheter forward along the fixed movable core. The steps of repositioning of such a stent are the same as for the primary delivery of the stent with the temperature of transformation, i.e. the transition temperature, higher than body temperature, which is described above and can be supplemented with an angioplasty in the same fashion if so desired clinically.

Figure 14:
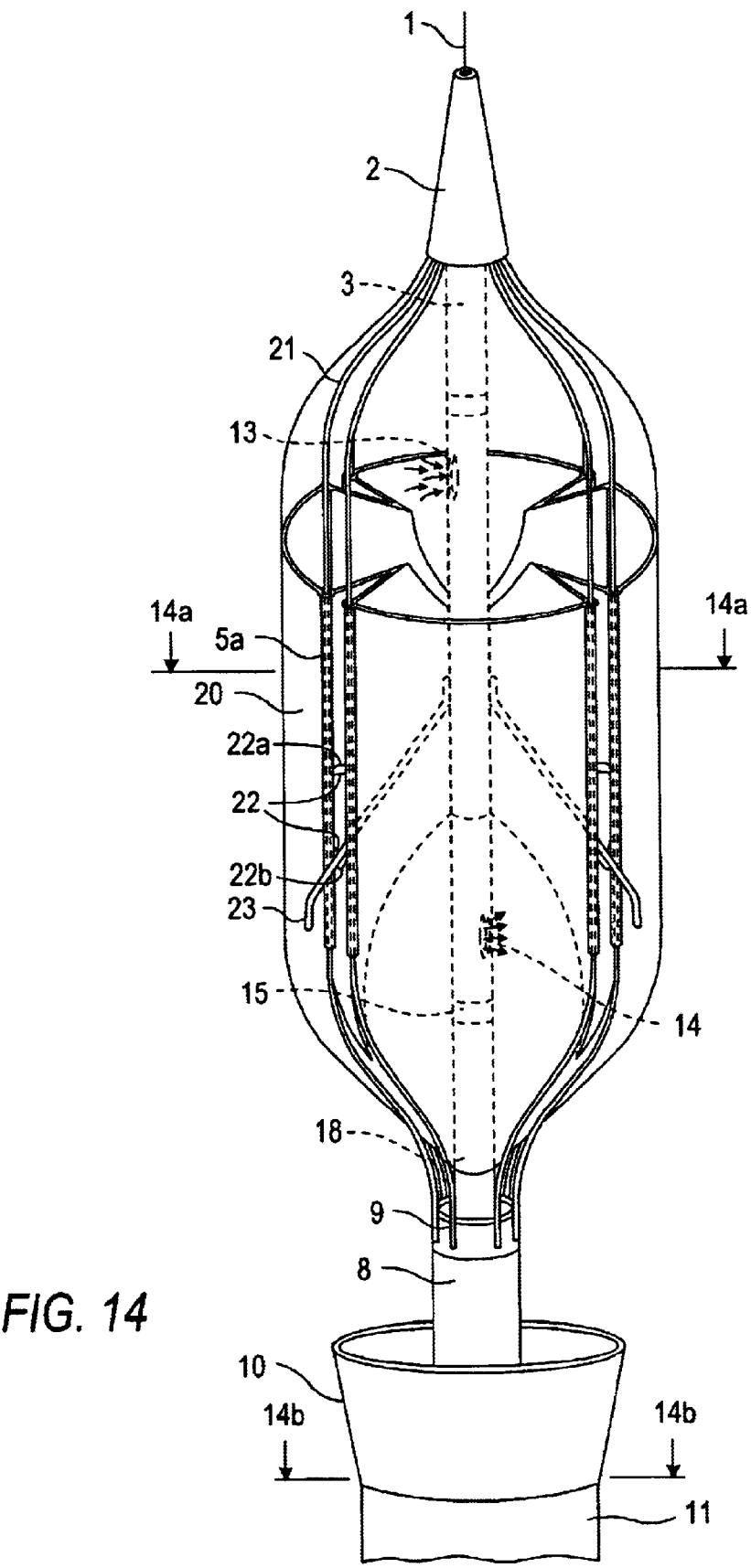
FIG. 14 is a perspective view of the first version of the third embodiment, partially broken away to show the first version of the circulation arrangement.
Figure 14A:
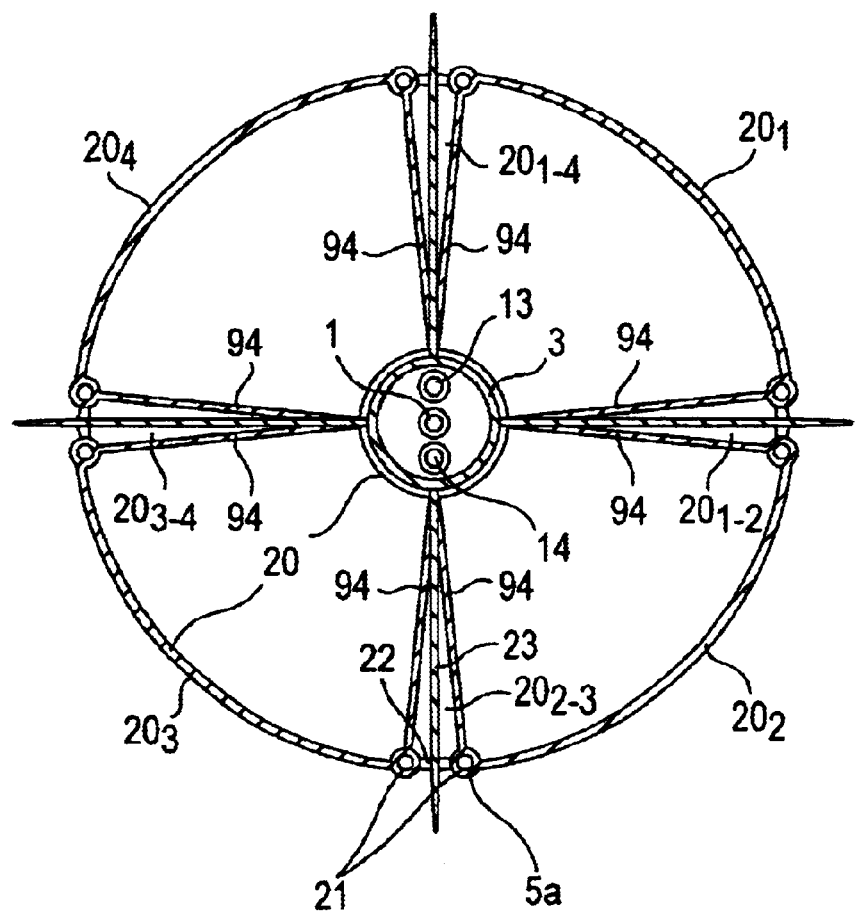
FIG. 14a is a section view taken along line A—A of FIG. 14.
Figure 14B:
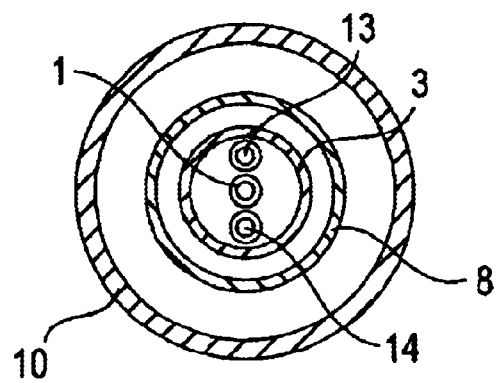
FIG. 14b is a section view taken along line B—B of FIG. 14.
Figure 15:
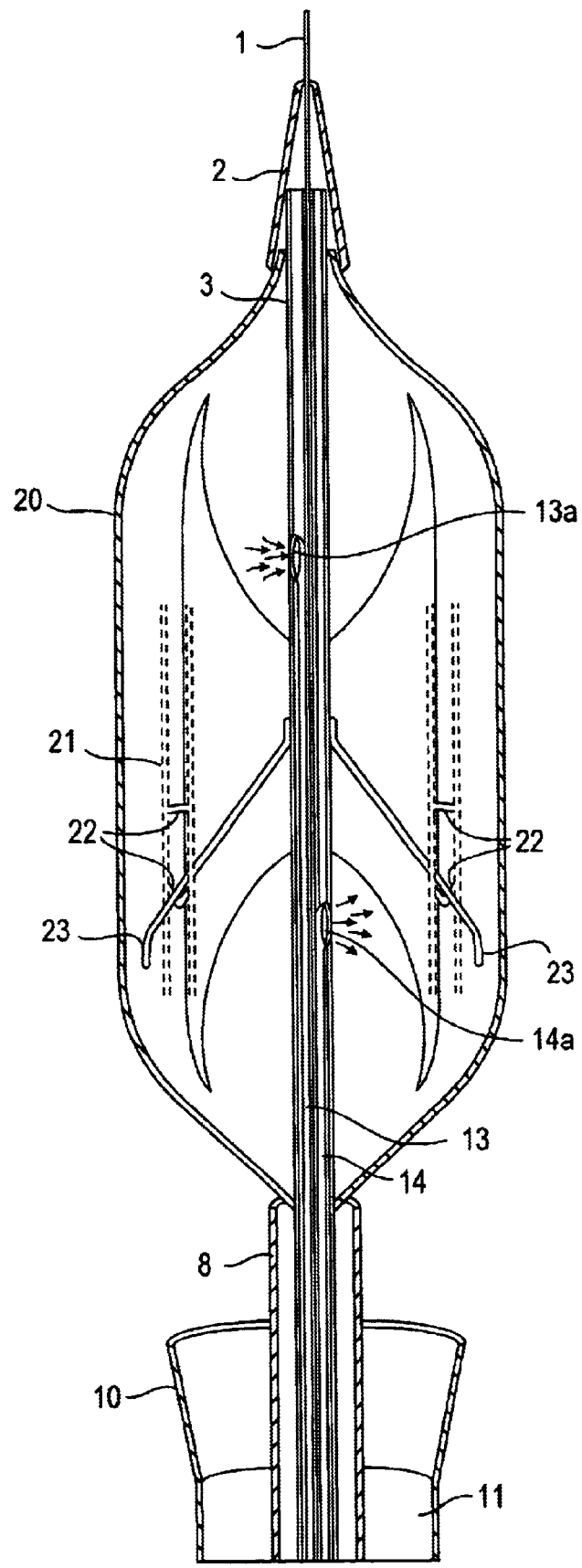
FIG. 15 is a longitudinal sectional view of the first version of the third embodiment.

Referring to FIGS. 13–16, a first version of a third embodiment of apparatus in accordance with the invention comprises a thermal transfer device 60C associated with a catheter assembly 50C and including a stent capturing device 70C. The thermal transfer device 60C comprises an inflatable and collapsible balloon 20 formed of the same type of material as that from which balloons 4 and 12 are made. The balloon 20 has a cloverleaf configuration in the cross sectional view (FIG. 14a). Balloon sectors $20_1$–$20_4$ merge with each other at the proximal and distal ends of the balloon (FIG. 14 and FIG. 15) and in the center of the balloon define radial spaces $20_{1-4}$, $20_{1-2}$, $20_{2-3}$ and $20_{3-4}$ between them (FIG. 14a). Each of the radial spaces are formed by a pair of opposed radially and axially extending wall members 94 extending between the outer wall of balloon 20 and the inner core catheter 3. The distal end of the balloon is attached to the inner core catheter 3 at the attachment of the cone 2 and the proximal end of the balloon is molded to the more proximal portion of the inner core catheter 3 at point 18.

The thermal transfer device 60C further includes a frame assembly 62C comprising four pairs of scaffolding wires 21, each wire having one end attached to the introducing conus 2, another end molded into the outer core catheter 8 at point 9 and a central region connected to balloon 20 by extending through passages 5a.

Figure 16:
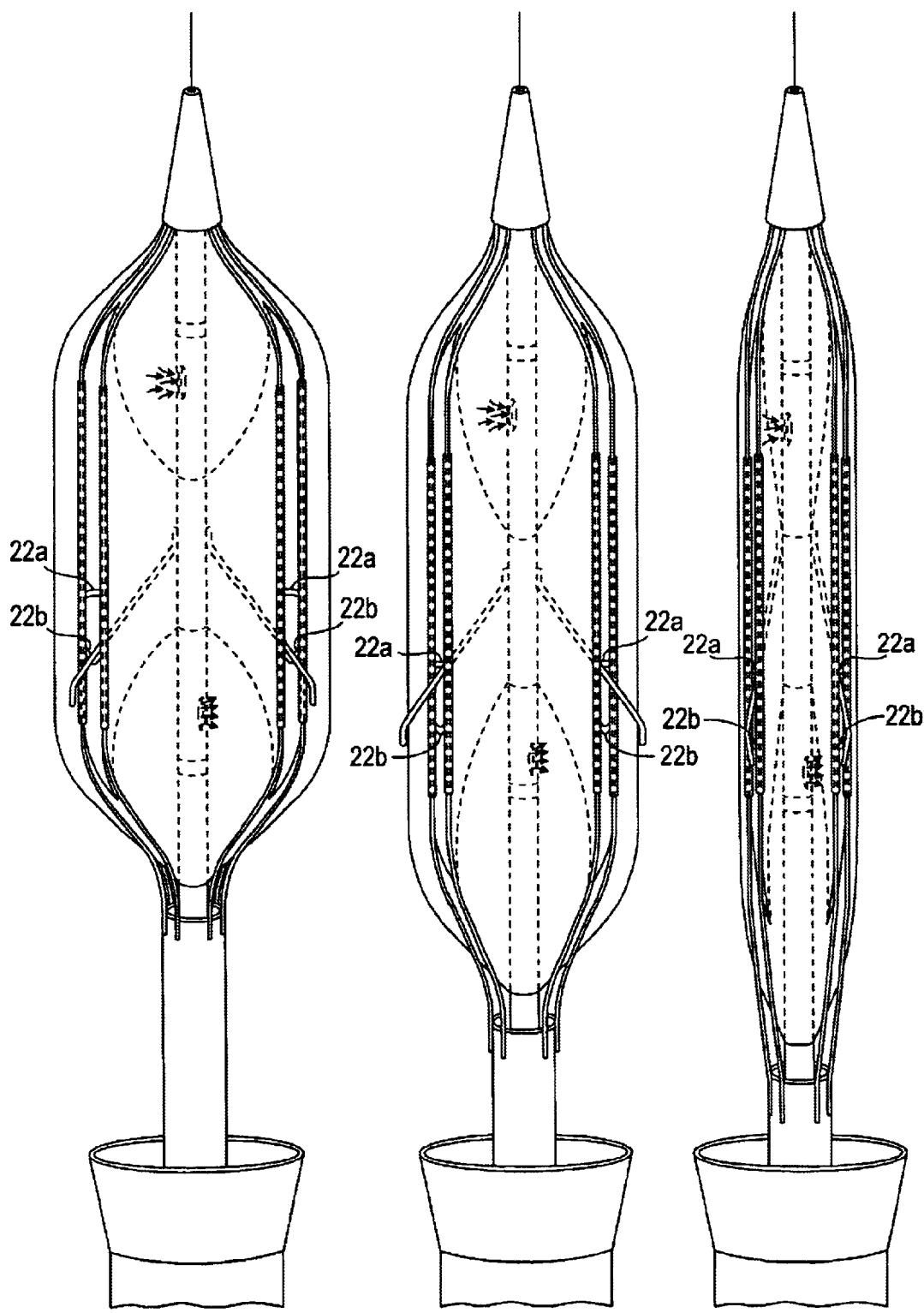
FIGS. 16a–c are three perspective views showing sequential steps of the collapse of the first version of the third embodiment of the thermal transfer device from its expanded diameter condition.
Figure 17:
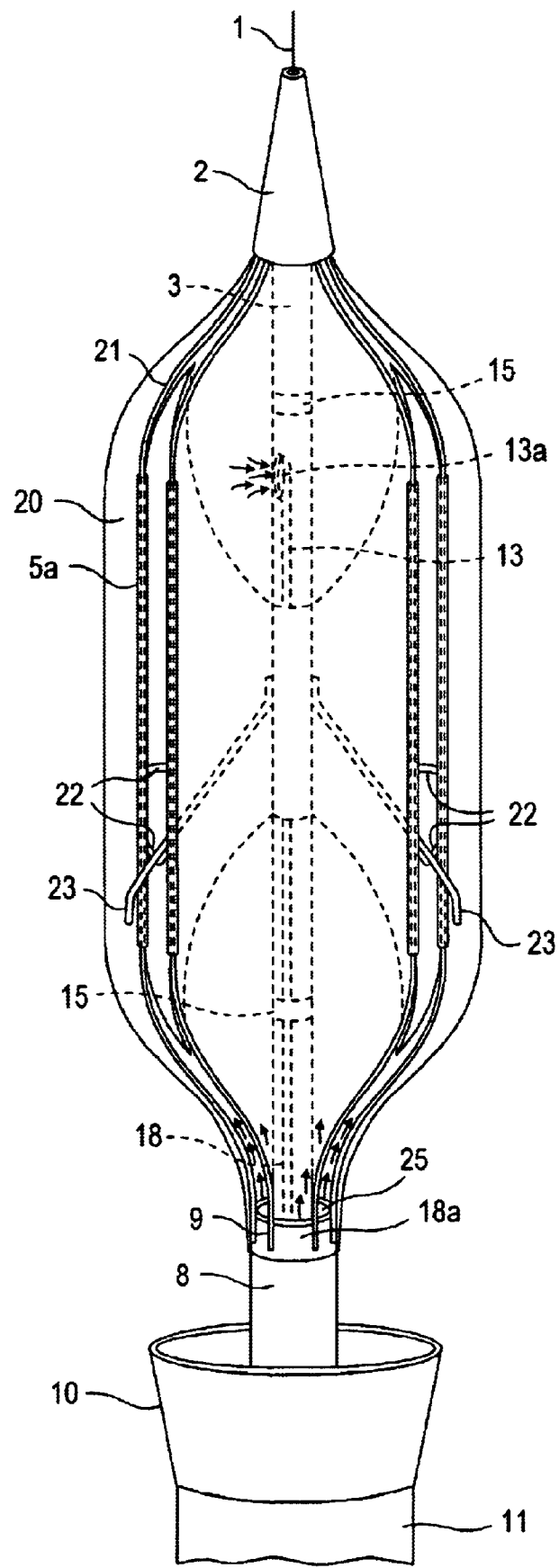
FIG. 17 is a perspective view of the second version of the third embodiment of the invention, with the second version of the thermal transfer fluid circulation arrangement.
Figure 18:
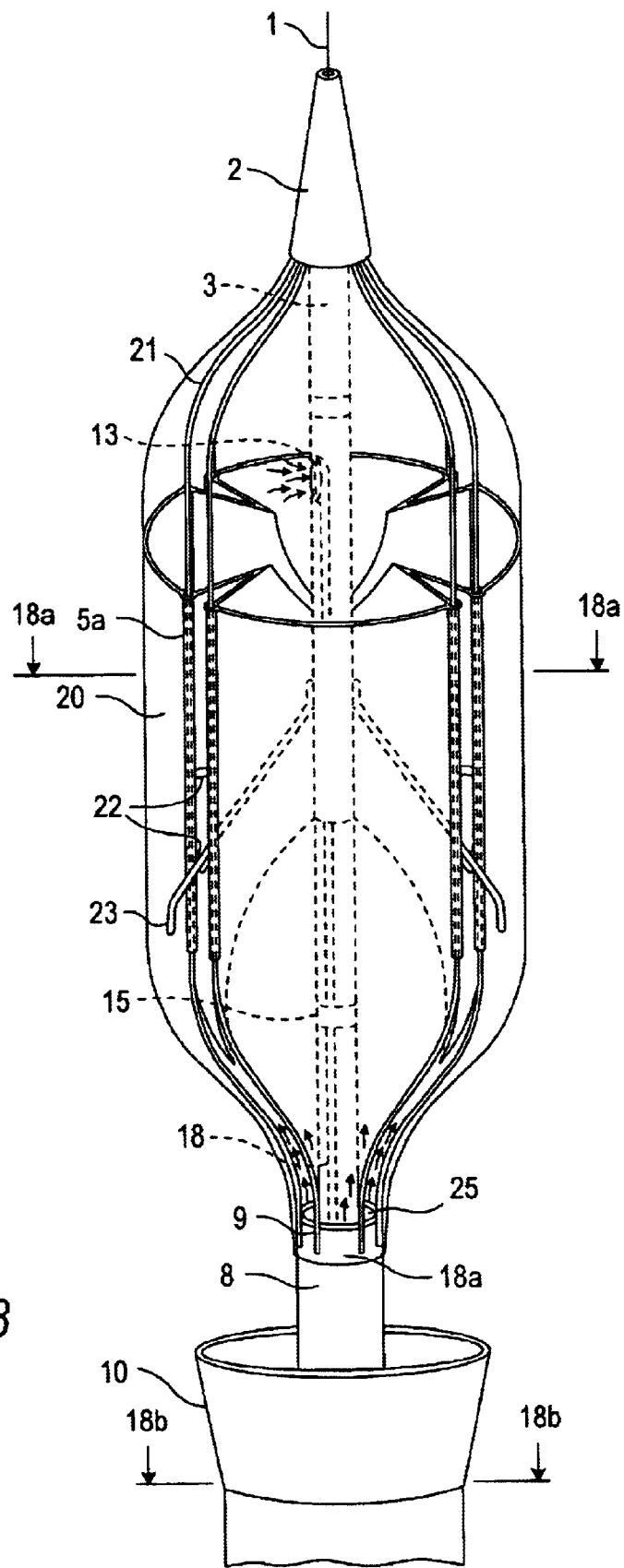
FIG. 18 is a perspective view of the second version of the third embodiment, partially broken away to show the second version of the circulation arrangement.
Figure 18A:
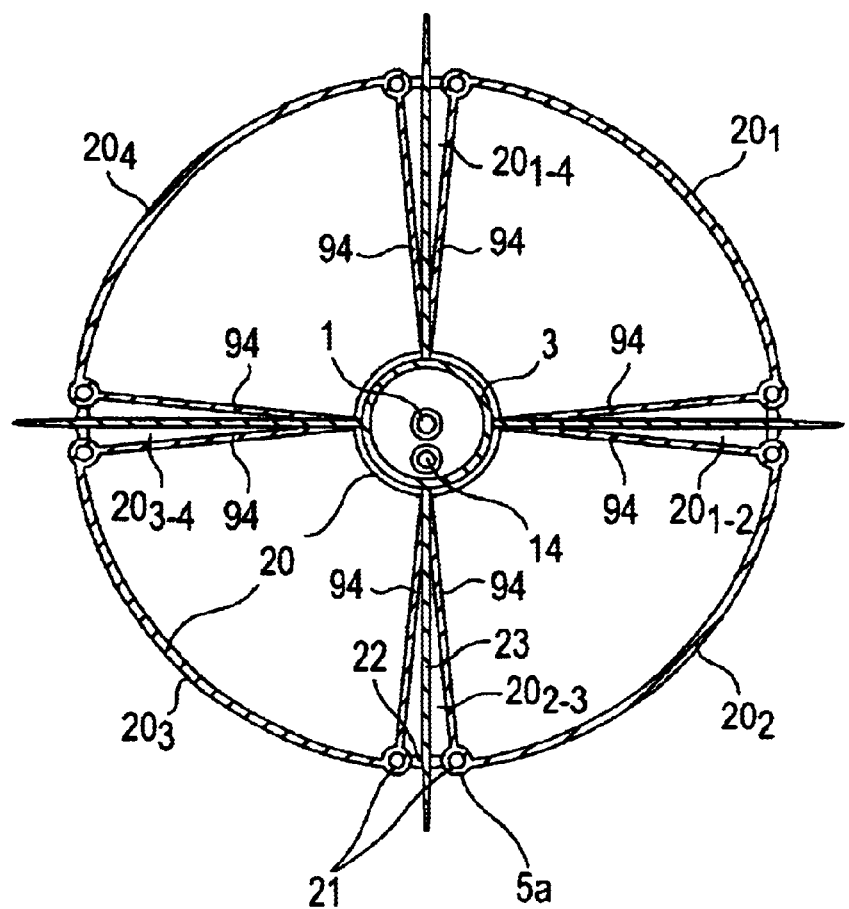
FIG. 18a is a section view taken along line A—A of FIG. 18.
Figure 18B:
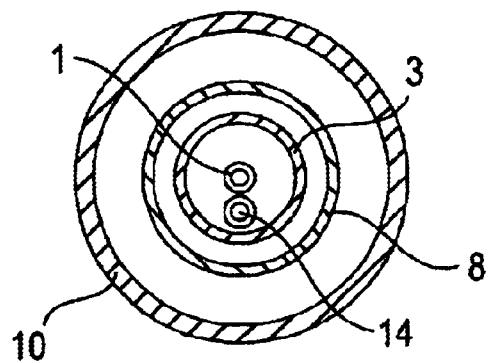
FIG. 18b is a section view taken along line B—B of FIG. 18.
Figure 19:
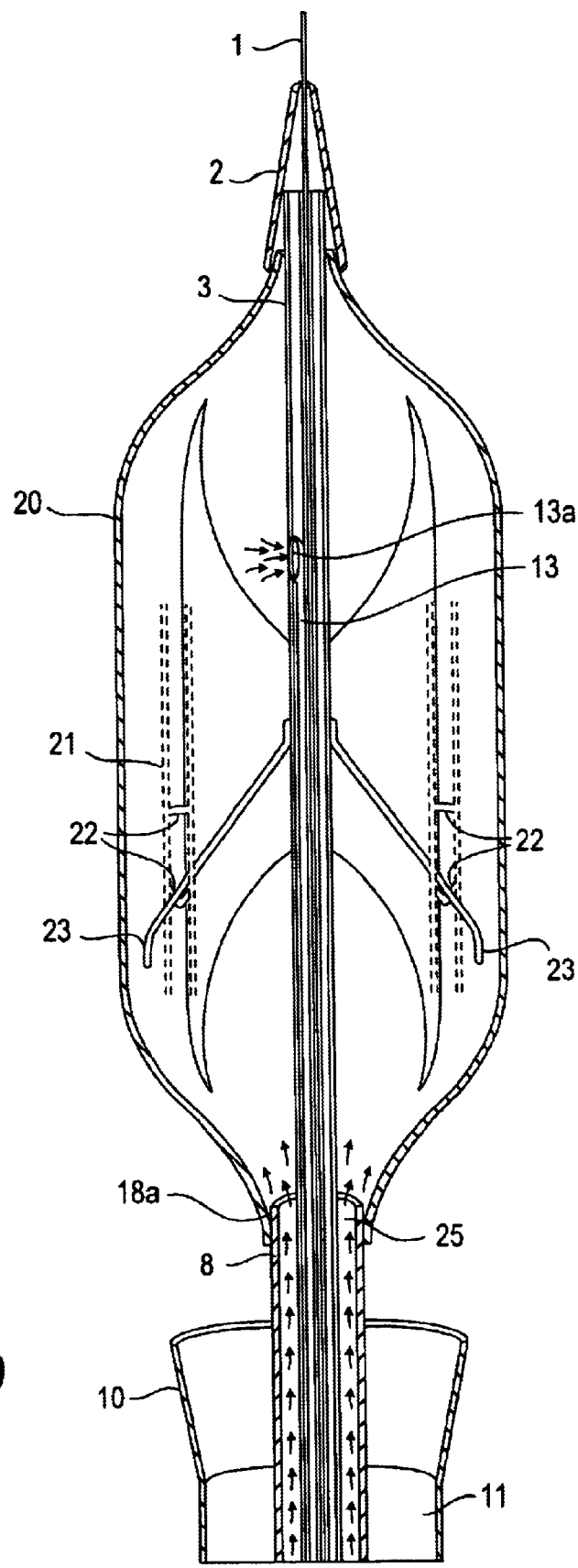
FIG. 19 is a longitudinal section view of the second version of the third embodiment.

The stent-capturing device 70C comprises capturing wire fingers 23 situated in respective radial spaces $20_{1-4}$, $20_{1-2}$, $20_{2-3}$ and $20_{3-4}$, each of which has one end attached to inner core catheter 3 and extends at an angle from the core catheter 3 between adjacent pairs of radial sectors $20_1$–$20_4$. A pair of connecting bars or bridging members 22a, 22b extend between each pair of the opposed walls 94 and captures a respective one of the capturing wires between them. As seen in FIG. 16, when the balloon 20 is collapsed, each capturing wire finger 23 will be engaged by the bridging member 22a to automatically close the capturing wire finger. On the other hand, when the balloon is expanded, each capturing wire finger 23 will be engaged by a bridging member 22b to automatically open the capturing wire finger.

In order to circulate thermal transfer fluid through the chamber of balloon 20 in the first version of the third embodiment shown in FIGS. 13–16, inflow and outflow channels 14 and 13 are formed in the inner core catheter 3 having inflow and outflow ports 14a and 13a.

Figure 25:
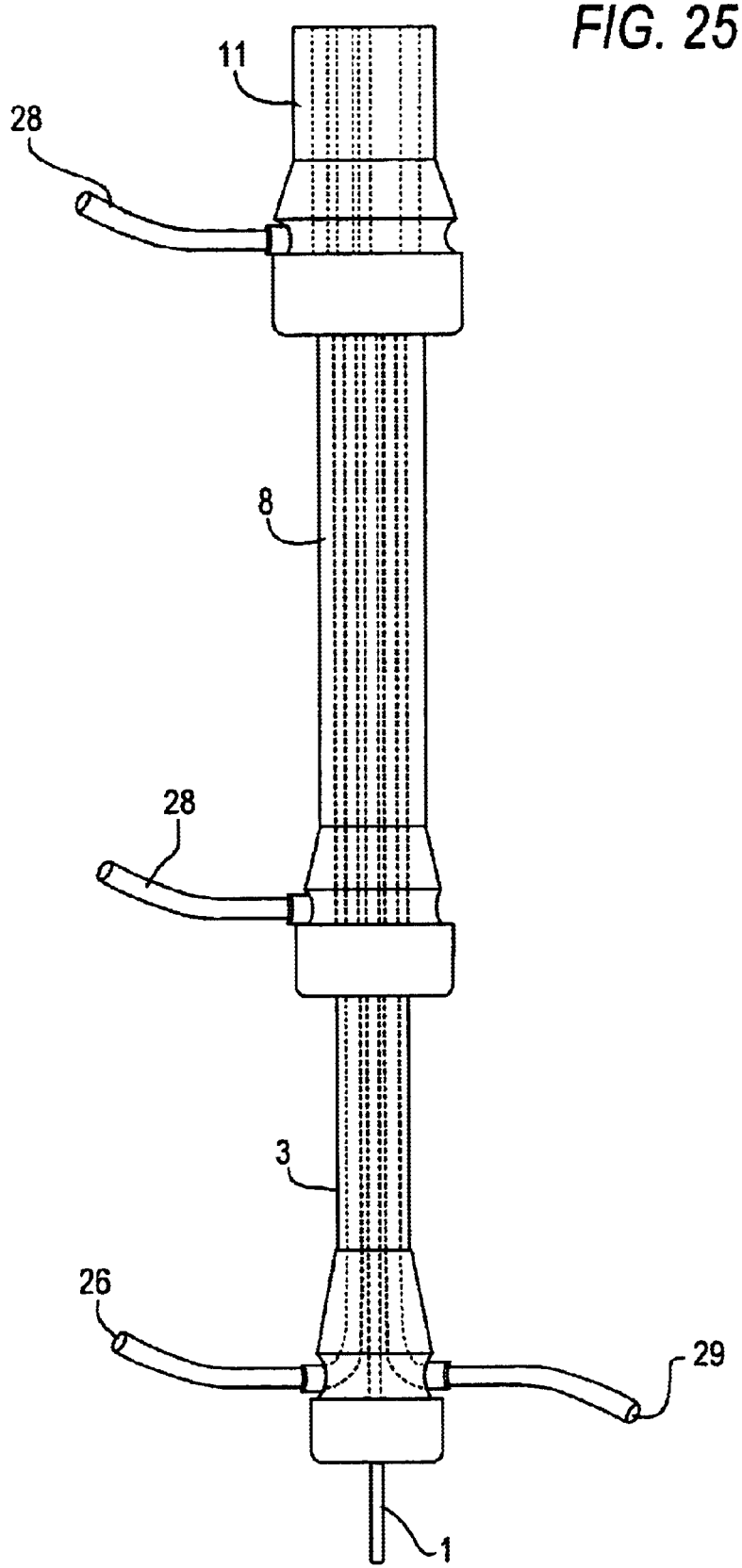
FIG. 25 is a perspective view of the proximal end of the catheter assembly of the first version of the third embodiment of the invention.

FIG. 25 shows the proximal end of the system of the first version of the third embodiment shown in FIGS. 13–16 outside the patient, where the stent receiving sheath 11 has a side arm port 28 for flushing of heparinized saline to prevent thrombus formation in the space between the stent receiving sheath 11 and the outer core catheter 8. The outer core catheter 8 has a side port 28 for flushing of heparinized saline to prevent thrombus formation between the outer core catheter 8 and the inner movable core catheter 3, which itself has two side ports: one port 29 for inflow of solution/gas into the inflow channel 14 of balloon 20 and the other port 26 for outflow of a solution/gas from the outflow channel 13, which is connected to the bag (not shown).

Referring to FIG. 17, FIG. 18, FIG. 19 and FIG. 20, the proximal end of the cloverleaf balloon 20 is attached to the outer core catheter 8 at point 18a. A second version of the third embodiment of the invention is illustrated wherein the space between the outer core catheter 8 and the movable core catheter 3 is used as an inflow channel 25 for infusion of a thermal solution or gas into the balloon. The movable core 3 has a central lumen for the guidewire 1 and channel 13 for outflow of circulating thermal solution or gas. The rest of the design of this system is identical to the system of FIGS. 13–16.

Figure 20D:
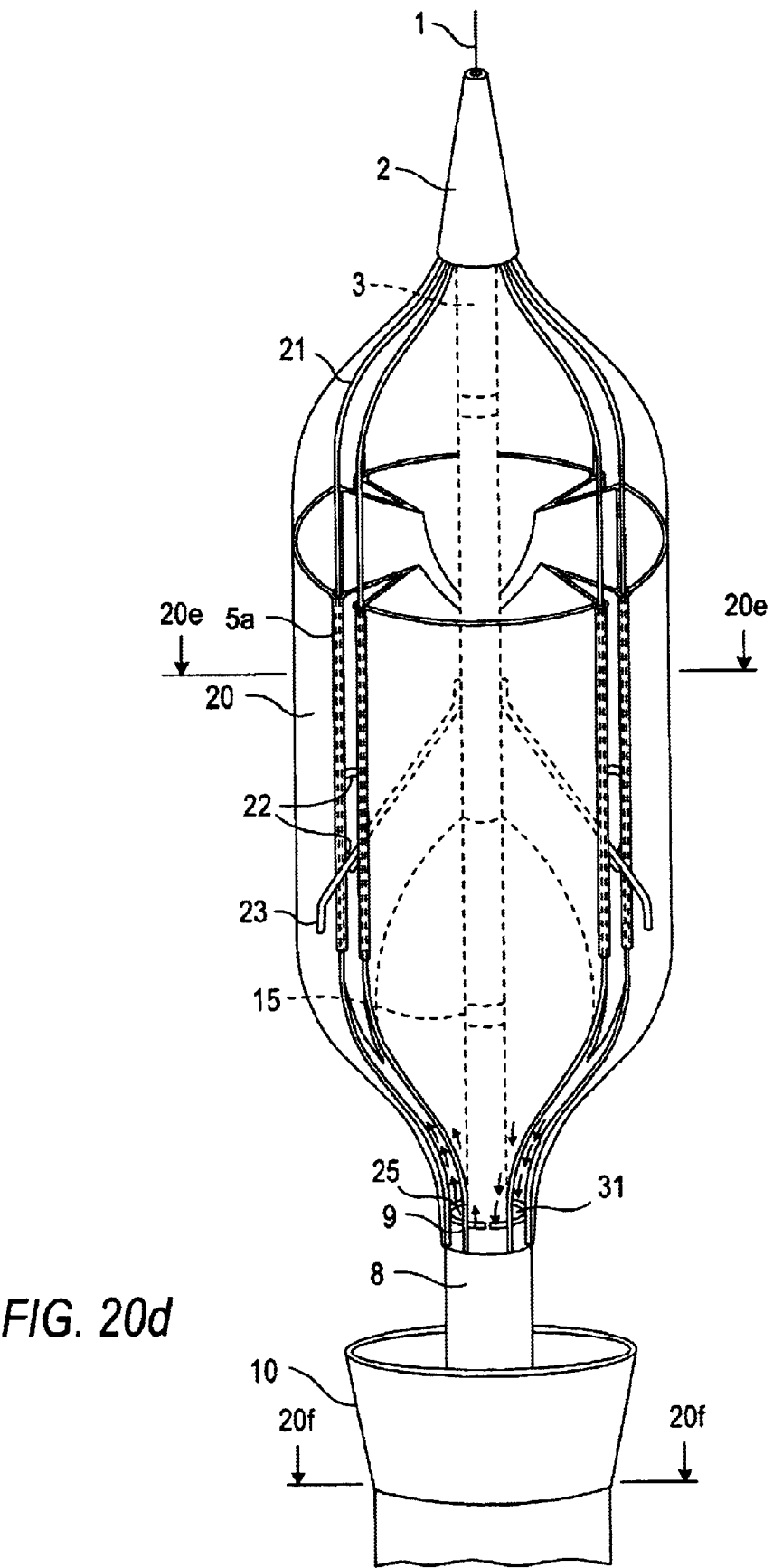
FIG. 20d is a perspective view of a modification of the second version of the third embodiment, partially broken away to show the modification of the second version of the circulation arrangement.
Figure 20E:
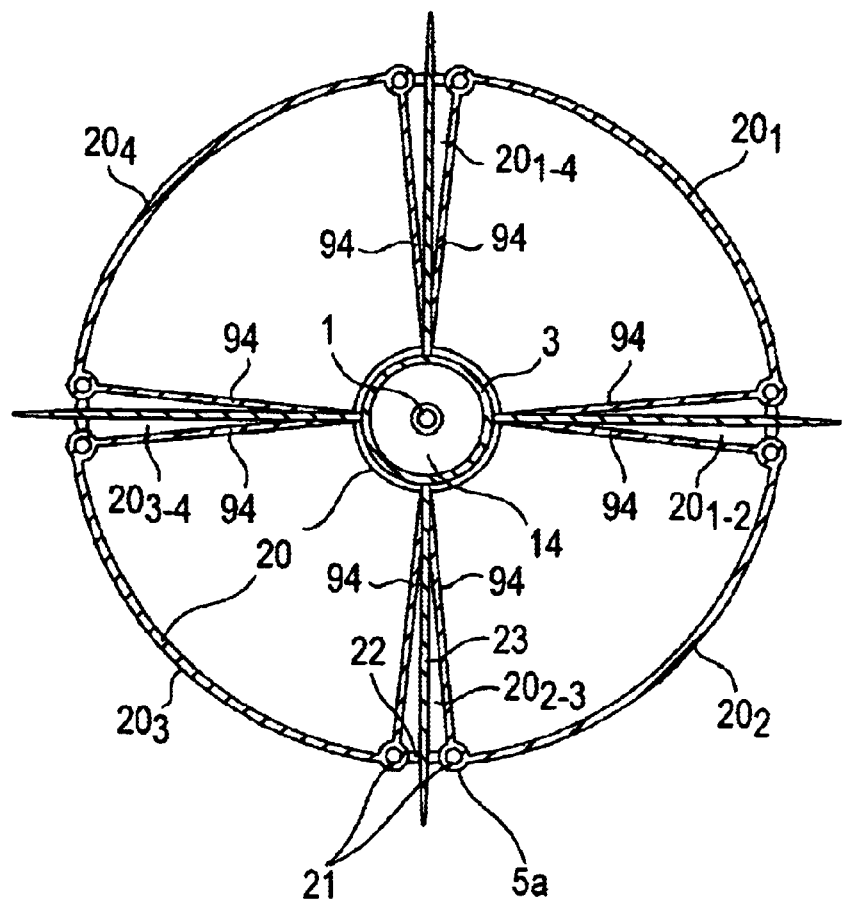
FIGS. 20e and 20f are section views of a modification of the second version of the third embodiment taken along lines E—E and F—F respectively in FIG. 20d.
Figure 20F:
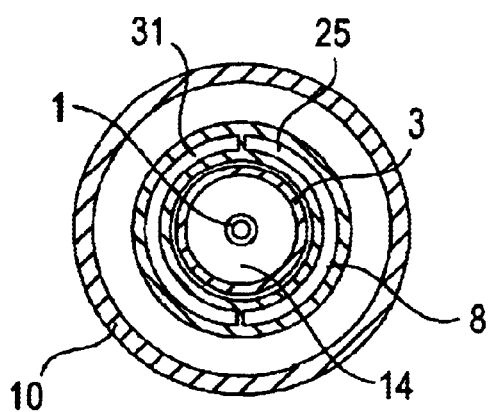

FIGS. 20D–F illustrate a modification of the system wherein both inflow and outflow channels 25 and 31 are provided through the space defined between the outer core catheter 8 and the movable core catheter 3. The channels are separated by two dividing partitions that extend along the entire length of the catheter.

Figure 26:
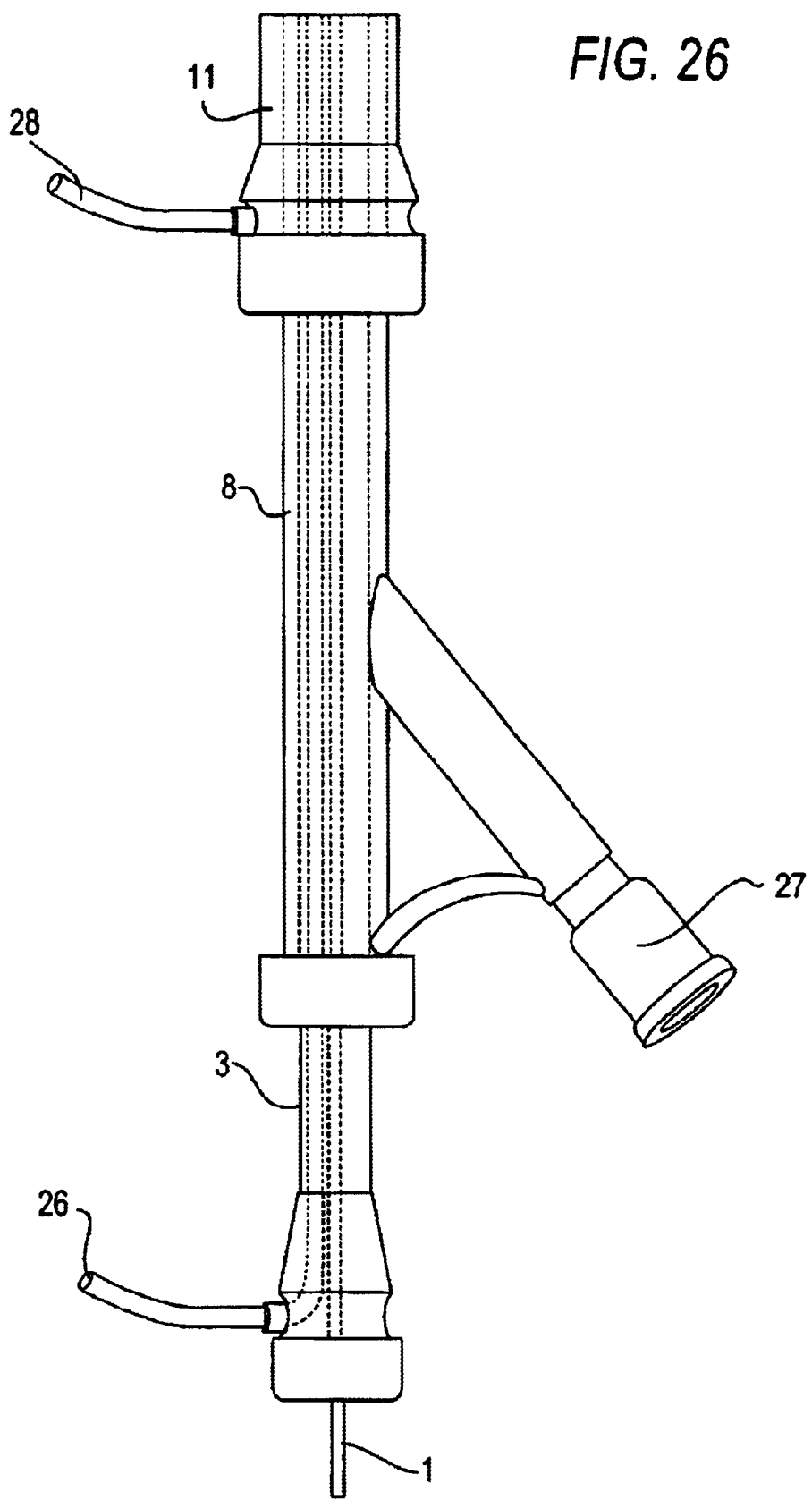
FIG. 26 is a perspective view of the proximal end of the catheter assembly of the second version of the third embodiment of the invention.

FIG. 26 illustrates the proximal end of the system shown in FIGS. 17–20 outside the patient, where the stent receiving sheath 11 has a side arm port 28 for flushing of heparinized saline to prevent thrombus formation in the space between the stent receiving sheath 11 and the outer core catheter 8. The outer core catheter 8 has a side arm port 27 for infusion of a thermal fluid into the cloverleaf type balloon. The movable core catheter 3 has an opening of an outflow channel 26 from the balloon and is connected to the collecting bag (not shown). A stop-cock is placed on the outflow channel 26 and is closed in cases of performing a balloon angioplasty.

Figure 21D:
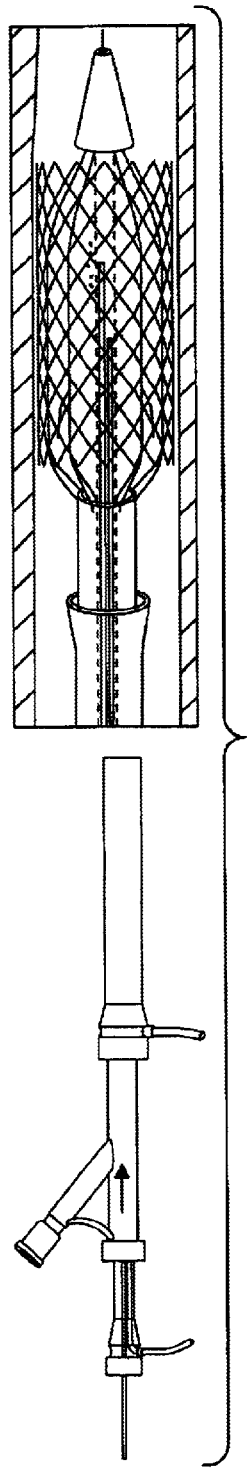
Figure 21E:
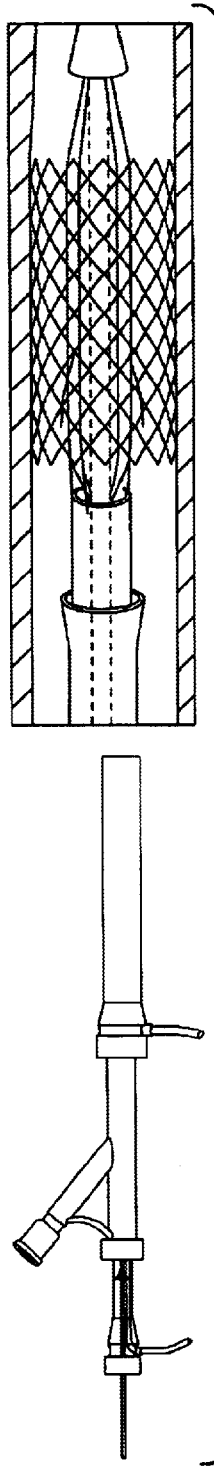
Figure 21F:
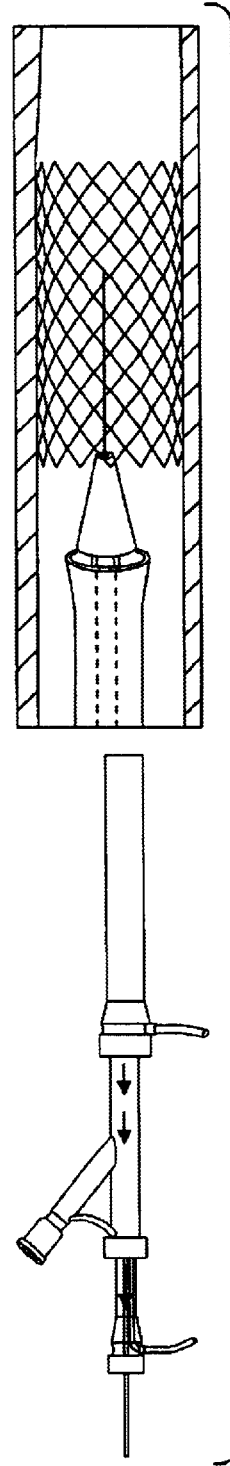

Referring to FIG. 21 a clinical scenario of primary stent deployment using the cloverleaf balloon system of FIGS. 17–20 is shown for deploying a stent made of a shape memory allow having a transition temperature at or below body temperature. The collapsed stent covered with the outer sheath is positioned inside the area of focal narrowing of the vessel under fluoroscopic guidance (FIG. 21a). The sheath is then withdrawn exposing the collapsed mounted stent and the infusion of a cold solution or gas is started immediately to control expansion of the stent (FIG. 21b). The collapsed stent is secured with the capturing wires or fingers, which together with the local cooling prevent premature expansion of the device. When the position of the system is precisely adjusted to the desired location under fluoroscopic guidance, the infusion of a cold thermal fluid is stopped and the metallic frame assembly is expanded by moving forward the outer core catheter along the fixed movable core (FIG. 21c). This allows natural heating of the stent to body temperature and its expansion to the original shape and diameter inside the area of stenosis, providing high radial force on the walls of the vessel and opening the narrowed region of the vessel. The primary stent deployment can be supplemented with a balloon angioplasty under high pressure, which is achieved by closing the outflow channel 13 and infusion of a diluted contrast material via the inflow channel (FIG. 21d). The pressure inside the balloon is regulated by the manometer attached to the inflow port outside the patient. The balloon is then deflated by stopping the infusion of the contrast material and opening the outflow channel, as well as collapsing the metallic frame by moving the movable core catheter forward along the fixed outer core catheter (FIG. 21e). This maneuver also causes the stent-capturing fingers or wires to slide out of the cellular spaces in the stent, releasing the stent from the physical restraint (FIG. 21e). The collapsed metallic frame and deflated balloon are then withdrawn back into the sheath and the entire system is removed from the body, leaving the stent in place (FIG. 21f).

The same system can be used for primary deployment of stents having a temperature of transformation higher than body temperature. Such stent is mounted on the balloon and delivered into the desired location inside the body covered with an outer sheath. It is then unsheathed, but does not expand until infusion of a warn solution at higher than body temperature is started via the inflow channel. The frame is then opened and the stent expands to its original shape and diameter, which it maintains after discontinuation of the infusion of a warm solution. The primary stent deployment can be supplemented with a balloon angioplasty in the same fashion as described above. The frame is then collapsed by moving the movable core forward along the fixed outer catheter, which provides sliding of the capturing wires out of the stent. The stent stays in place, exhibiting persistent radial force on the walls of the vessel or other tubular organ. The delivery system is then safely removed from the body.

Referring to FIG. 22 the steps of 2-way shape memory stent retrieval with the cloverleaf balloon design are shown.

Figure 22A:
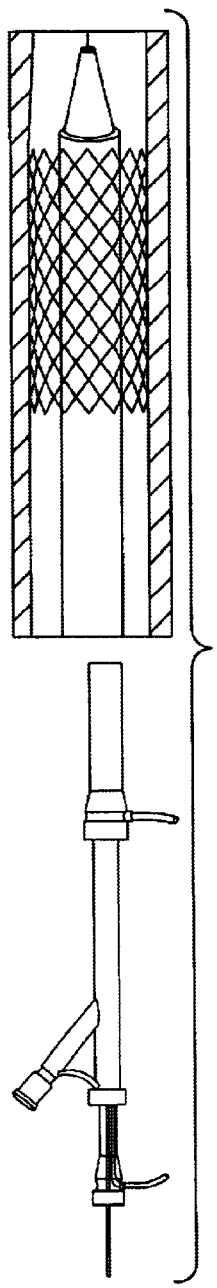
Figure 22B:
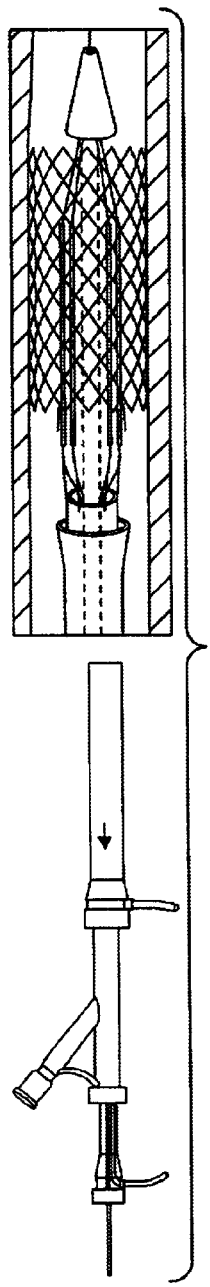
Figure 22C:
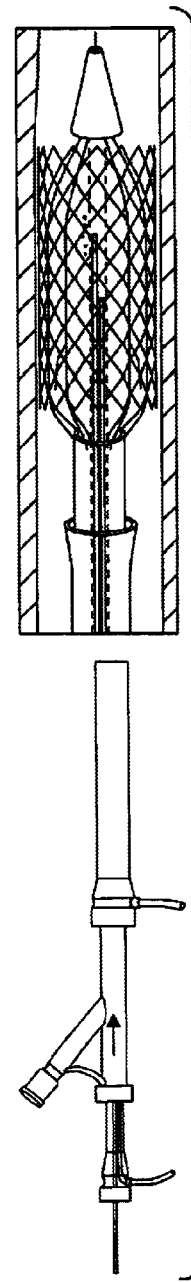
Figure 22D:
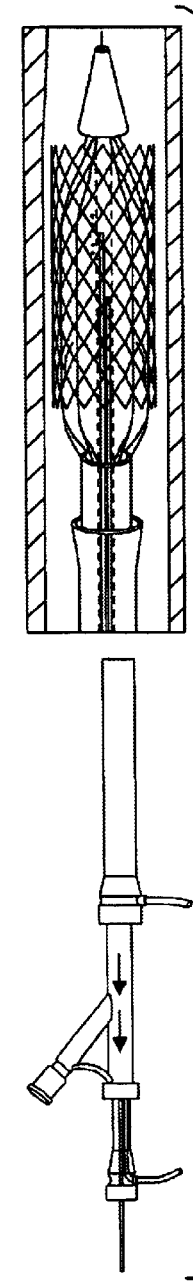

The closed system is introduced and positioned inside the stent, which has to be removed (FIG. 22a). The outer sheath is then withdrawn back and assumes a flared configuration after detaching from the introducing conus (FIG. 22b). The metallic frame opens by advancing the outer core catheter along the fixed movable core and the cold thermal transfer fluid is infused into the balloon to cool the stent to the desired temperature, which is lower for stents with the first transition temperature at or below body temperature and higher (but still lower than body temperature) for stents with the first transition temperature above body temperature (FIG. 22c). The outer core catheter 8 is then moved back while the movable core catheter 3 remains fixed in the same position, stretching the frame and collapsing the balloon. The stent, or at least its proximal end, collapses with reduction in diameter of the frame 62c, while the stent-capturing wires 23 stay open nearly touching the vessel wall (FIG. 22d). The stent, or at least its proximal end, collapses over the stent capturing wires 23, which protrude through the cells of the stent. The stent capturing wires 23 remain open until they meet the cross bars 22 bridging the spaces between the sectors $20_1$–$20_4$ of balloon 20. Further stretching of the frame 62C causes closure of the capturing wires 23 over the balloon 20 with the stent, or its proximal portion, caught between the capturing wires 23 and the balloon 20 (FIG. 22e). At this point the stent is easily drawn into the receiving sheath (FIG. 22f). The next step is complete removal of the recovered stent from the body (FIG. 22g) or adjustment of its position while the stent is still in the collapsed state within the sheath with subsequent re-deployment into the desired location, using the same sequence of the steps for primary stent deployment described above.

The above described methods prevent any motion of the delivery system during deployment. The entire stent uniformly expands at the same time inside the area of narrowing, exerting radial force on the diseased wall of the vessel and restoring the normal lumen and flow. All current self-expanding stents have to be unsheathed gradually, exposing immediately expanding small segments of the device at a time. Persistent pulling back of the sheath during opening of the stent inside the vessel can cause slight forward or backward motion of the device, potentially leading to misplacement of the stent proximal or distal to the area of interest. This problem is eliminated by the system described above.

Figure 23:
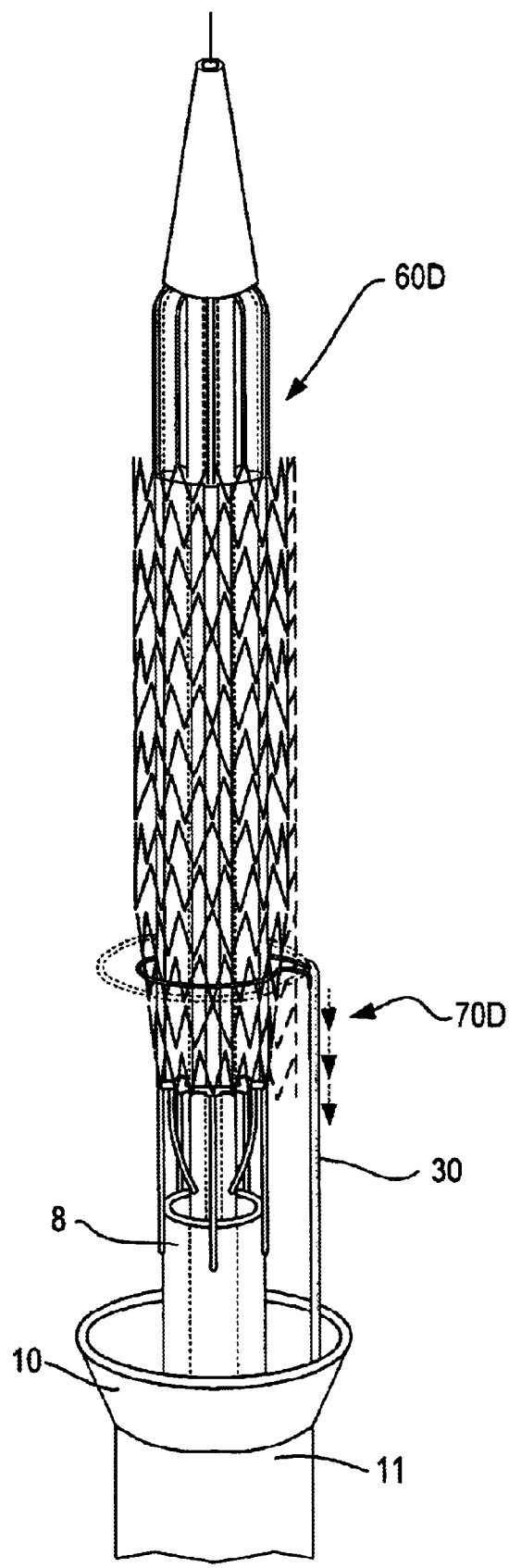
FIG. 23 is a perspective view of the first embodiment of the invention with the thermal transfer device in a collapsed condition and including a snare-type stent capturing device.

Referring to FIG. 23, another device 70D for capturing the stent is illustrated. As the stent is cooled by the thermal transfer device 60, and partially collapses, it is grabbed on the balloon by a snare loop 30. The loose snare loop 30 is advanced around the partially collapsed stent and then tightens into a smaller loop by sliding the thin catheter over it. This maneuver securely fixes the stent to the framed balloon and promotes further mechanical collapse of the stent for easy insertion into the outer sheath 11.

While the embodiments of the invention described above all utilize heated or cooled fluid circulating through the balloon chamber to transfer heat to or from the stent, the thermal transfer device may comprise means for directly heating the heat transfer surface of the device.

Figure 27:
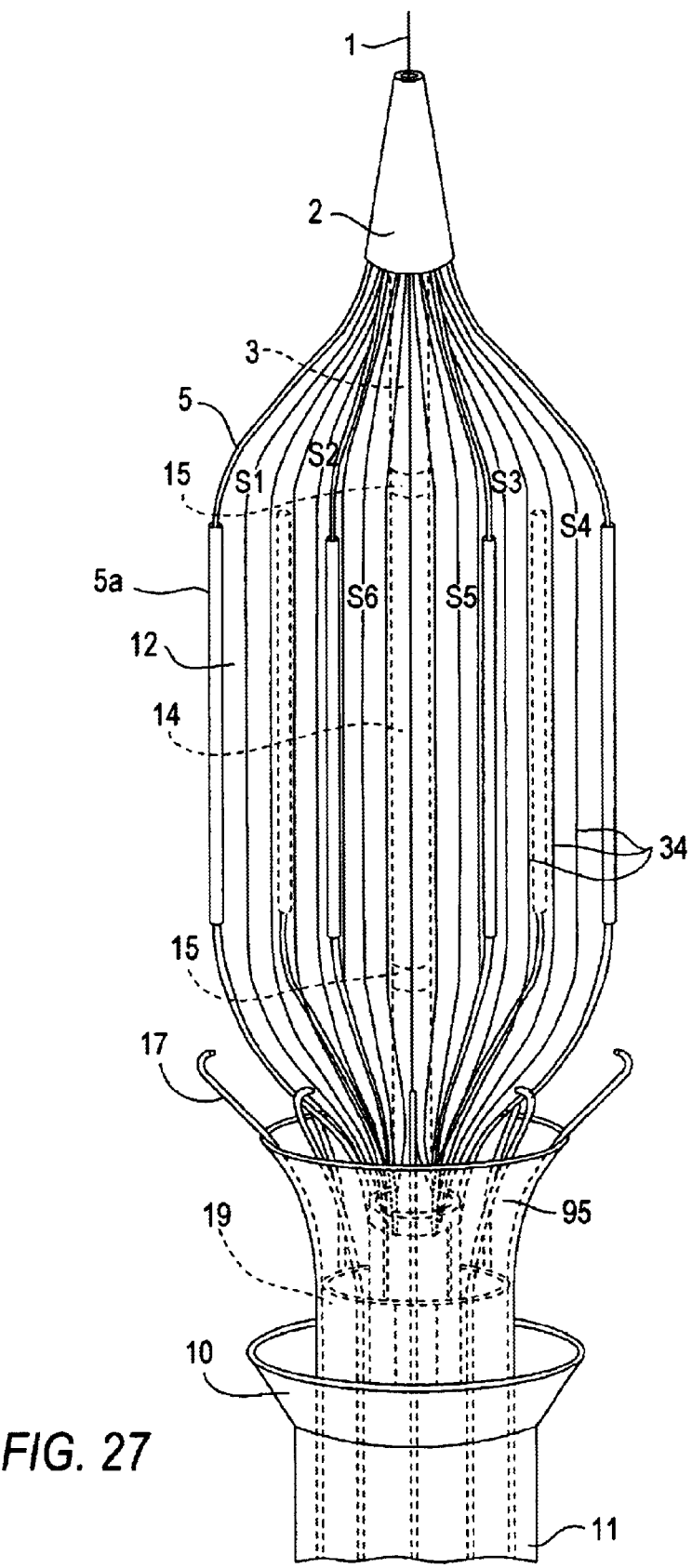
FIG. 27 is a perspective view of a fourth embodiment of the catheter assembly and associated thermal transfer device in accordance with the invention.

FIG. 27 illustrates a solid balloon system with multiple heating electrical resistance wires 34 provided on the surface of the balloon 12 to provide direct heating of the stent when an electrical current is passed through the wires. The wires 34 are connected to an electrical source outside the patient. This system can be beneficial for the deployment of stents having transition temperatures above body temperature.

Figure 28:
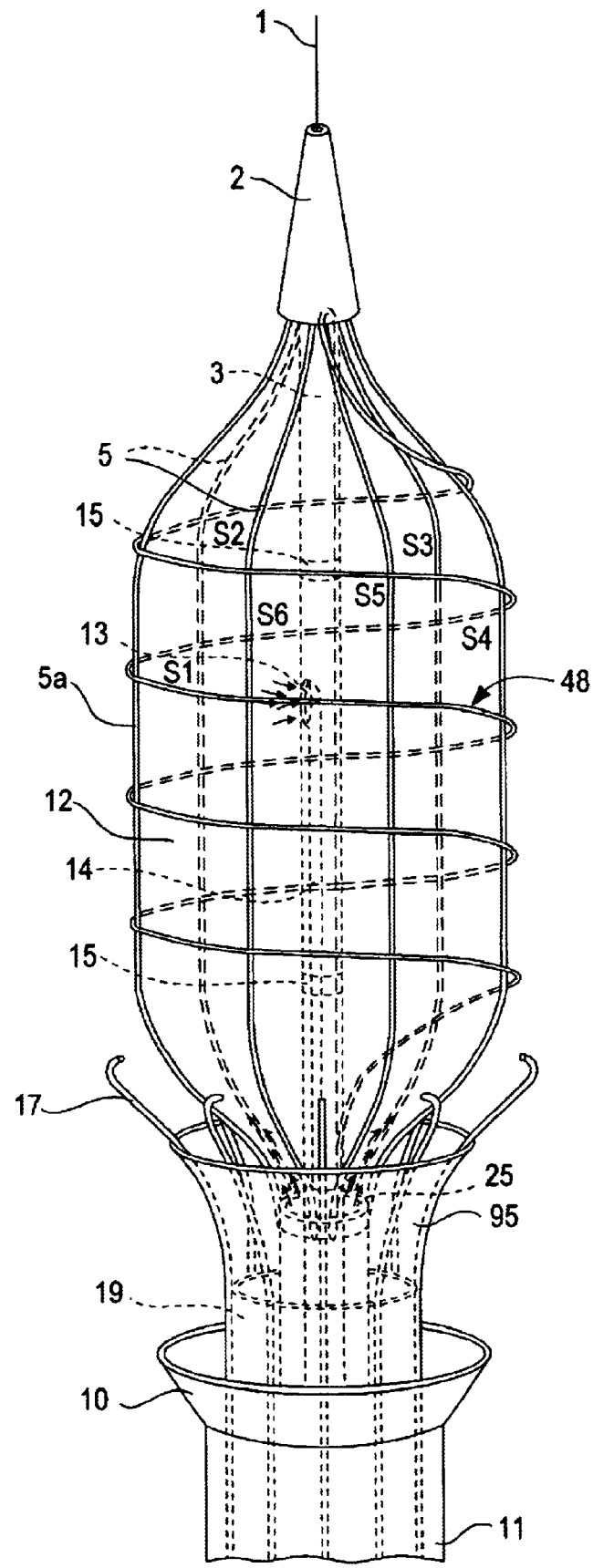
FIG. 28 is a perspective view of a fifth embodiment of a catheter assembly and associated thermal transfer device in accordance with the invention.

Referring to FIG. 28, the outer surface of the solid balloon 12 is provided with an electromagnetic coil 48, which is heated by generation of an electrical current from application of an external magnetic field. The electromagnetic balloon can be used for deployment of stents having transition temperatures higher than body temperature by direct heating of the stent or by heating fluid injected into the balloon. The same system can be used for retrieval or repositioning of the stents with transformation temperatures greater than body temperature by infusing a cooling solution/gas into the balloon.

While the first, second and third embodiments of the invention described above utilize thermal transfer fluid which is heated or cooled at the proximal end of the catheter assembly outside the body, other techniques for heating the thermal fluid may be employed.

Figure 29:
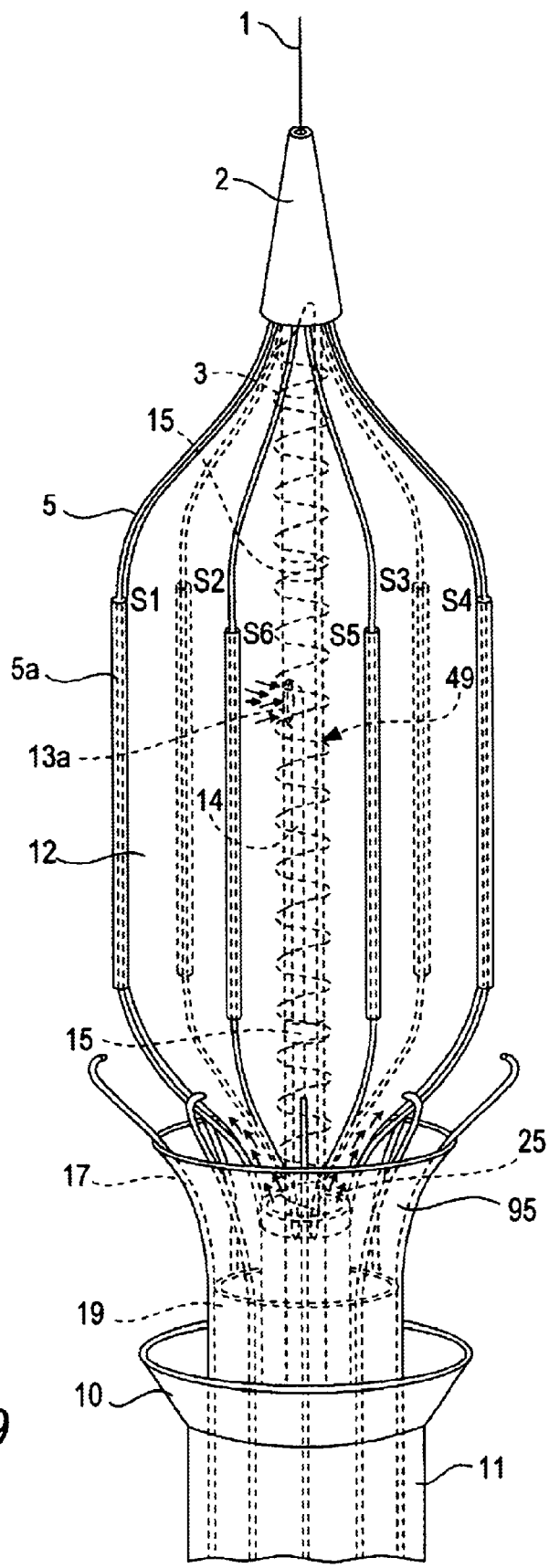
FIG. 29 is a perspective view of a sixth embodiment of a catheter assembly and associated thermal transfer device in accordance with the invention.

FIG. 29 illustrates a solid balloon system with an electromagnetic coil 49 inside the balloon (as opposed to outside the balloon as shown in FIG. 28) to provide heating of the fluid in the balloon chamber after application of an external magnetic field. It is applicable for the deployment, repositioning or retrieval of the stents with first transformation temperatures higher than body temperature.

Figure 30:
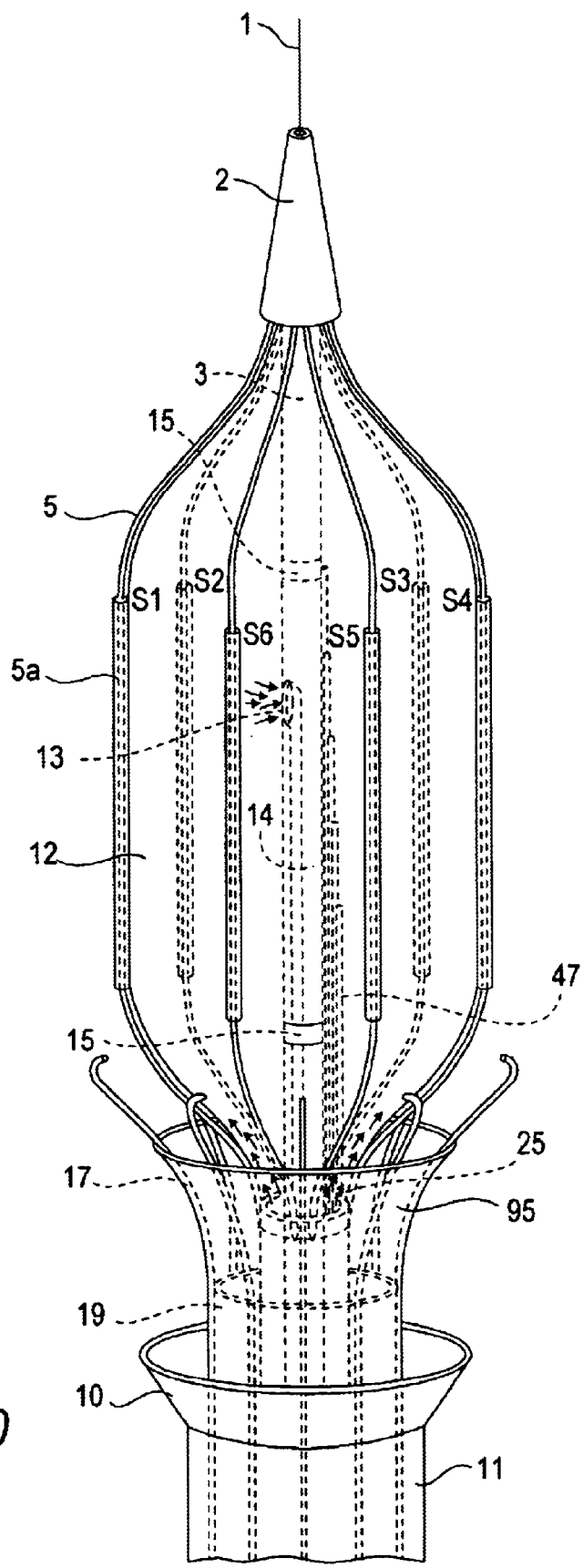
FIG. 30 is a perspective view of a seventh embodiment of a catheter assembly and associated thermal transfer device in accordance with the invention.

FIG. 30 illustrates a thermal transfer device provided with multiple optic fibers 47 inside the balloon for heating of the circulating fluid by a laser beam, which is connected to a source generator system on the proximal end outside the patient. The system can be used for the deployment, repositioning or retrieval of stents with first transformation temperatures higher than body temperature.

Figure 31:
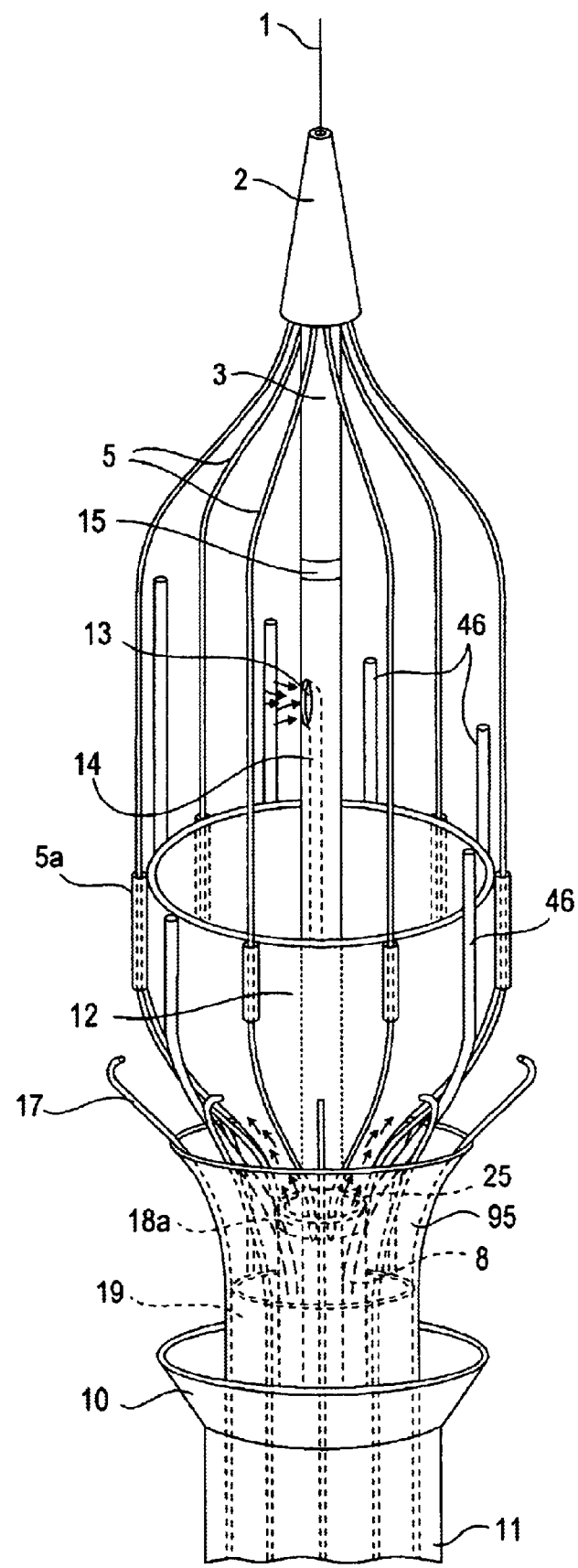
FIG. 31 is a perspective view of an eighth embodiment of a catheter assembly and associated thermal transfer device in accordance with the invention.

Referring to FIG. 31, optic fibers 46 are situated on the outer surface of the balloon and can be used for direct heating of the mounted stent or for heating of fluid circulating inside the balloon. The system can be used for the deployment, repositioning or retrieval of the stents with transition temperature higher than body temperature.

Figure 32:
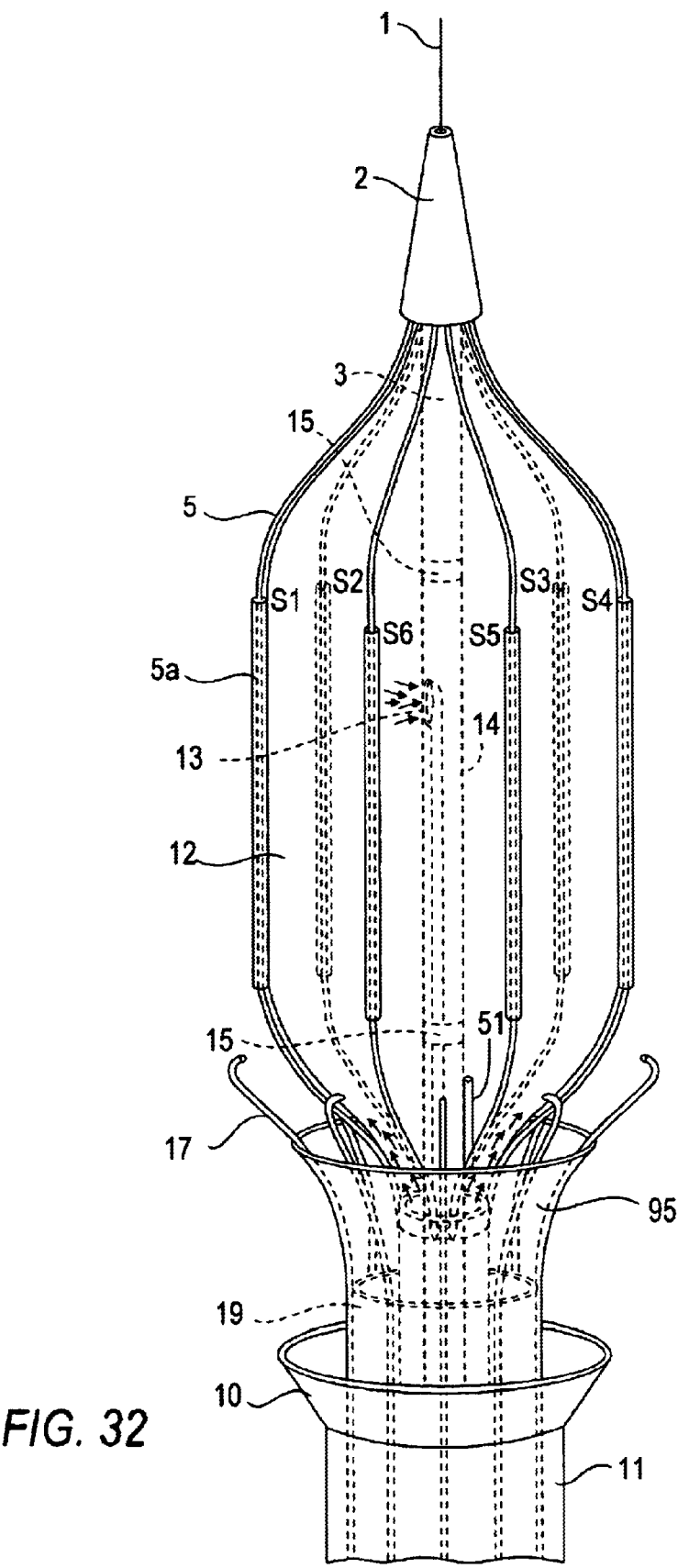
FIG. 32 is a perspective view of a ninth embodiment of a catheter assembly and associated thermal transfer device in accordance with the invention.

FIG. 32 demonstrates another system with an ultrasound probe 51 inside the balloon, which provides fast heating of the circulating fluid for the deployment of stents with transition temperatures higher than body temperature. An ultrasound generator is connected to the system on the proximal end outside the patient. The system can be also used for repositioning or retrieval of the same stents by circulation of cooling thermal fluid inside the balloon.

All currently available and all future stents and stent-grafts made from Nitinol or other materials with shape memory capabilities can be delivered with the above described systems and after training or heat/mechanical treatment can demonstrate second way memory effect, and can be retrieved from the body or repositioned into the desired location by using the systems that are described in this patent.

Obviously, numerous variations of the present invention are possible within the scope of the claims appended hereto. Accordingly, the invention may be practiced otherwise than as specifically described herein.

We claim:

1. Apparatus for deploying and/or retrieving and/or repositioning a stent having a shape memory, comprising:
    an elongate catheter assembly having a proximal end region and a distal end region;
    a thermal transfer device situated on said catheter assembly at said distal end region thereof defining a chamber having a thermal transfer wall, said thermal transfer device comprising an expandable member structured and arranged to expand and collapse between an expanded condition and a collapsed condition and a frame assembly coupled to said expandable member selectively actuatable from said proximal end region of said catheter assembly for expanding and collapsing said expandable member, said frame assembly including a plurality of flexible elongate frame members, each elongate frame member coupled to both said expandable member and said catheter assembly at said distal end region thereof; and means for providing an inflow of thermal transfer fluid into said chamber from said proximal end region of said catheter assembly for transferring thermal energy to said stent through said thermal transfer wall, to adjust the temperature of the stent.

2. Apparatus as recited in claim 1 wherein said catheter assembly comprises an inner core catheter and a relatively movable outer core catheter situated over said inner core catheter, said outer core catheter having a distal end which is situated proximally of the distal end of said inner core catheter so that a projecting portion of said inner core catheter extends beyond said distal end of said outer core catheter and wherein said wire frame comprises a plurality of wires, each wire having one end fixed to a distal end of said projecting portion of said inner core catheter, another end fixed to the distal end of said outer core catheter, and a central region attached to said expandable members; whereby relative movement of said inner and outer core catheters to shorten the projecting portion of said inner core bends said wires and expands said expandable member to its expanded condition while relative movement of said inner and outer core catheters to lengthen the projecting portion of said inner core straightens said wires and collapses said thermal transfer device to its collapsed condition.

3. Apparatus as recited in claim 2 wherein said expandable member comprises an inflatable balloon.

4. Apparatus as recited in claim 3 wherein said thermal transfer material forming said chamber comprises flexible sheet material.

5. Apparatus as recited in claim 4 wherein said thermal transfer material comprises a polymer material.

6. Apparatus as recited in claim 1 wherein said expandable member includes a balloon formed at least in part of said thermal transfer wall of said chamber.

7. Apparatus as recited in claim 1 wherein said means for providing an inflow of thermal transfer fluid into said chamber comprise passages formed at least in part in said elongate catheter assembly.

8. Apparatus as recited in claim 7 wherein said passages open from said catheter assembly into the interior of said chamber of said thermal transfer device.

9. Apparatus as recited in claim 8 wherein said elongate catheter assembly comprises an inner core catheter and a relatively movable outer core catheter situated over said inner core catheter, and wherein said opening of said passage comprises an axially facing annular opening defined between a distal end of said outer core catheter and said inner core catheter.

10. Apparatus as recited in claim 8 wherein said catheter assembly comprises an inner core catheter, and wherein said opening of said passage comprises a radially facing opening constituting a port formed in a side wall of said inner core catheter.

11. Apparatus for deploying, retrieving and/or repositioning a stent having a shape memory, comprising:

an elongate catheter assembly having proximal and distal end regions;

a thermal transfer device including a balloon member operatively connected to said catheter assembly defining a chamber having a thermal transfer wall, at least a part of which constitutes a thermal transfer material;

a stent capturing device including at least one elongate member coupled to said catheter assembly at said distal end region thereof, said at least one elongate member having a free end portion situated proximate to said balloon member for releasably holding a stent situated on said balloon member during deployment, and for releasably grasping said stent during retrieval and/or repositioning; and circulation means for providing an inflow of thermal transfer fluid into the interior of said chamber for transferring thermal energy to a stent through said outer thermal transfer wall to adjust the temperature of the stent, and for providing an outflow of thermal transfer fluid from the interior of said chamber to said proximal end region of said catheter assembly.

12. Apparatus as recited in claim 11 wherein said catheter assembly comprises at least one core catheter, and wherein said balloon member has a distal end sealed in fluid sealing relationship around the circumference of said core catheter and a proximal end also sealed in fluid sealing relationship around the circumference of said core catheter.

13. Apparatus for deploying, retrieving and/or repositioning a stent having a shape memory, comprising:

an elongate catheter assembly having proximal and distal end regions;

a thermal transfer device comprising an expandable member situated on said catheter assembly defining a chamber having a thermal transfer wall, at least a portion of which constitutes a heat transfer material, said expandable member being expandable and collapsible between expanded and collapsed conditions;

circulation means for providing an inflow of thermal transfer fluid from the proximal end region of said catheter assembly into the interior of said chamber and for providing an outflow of thermal transfer fluid from the interior of said chamber to the proximal end region of said catheter assembly; and a stent capturing device including at least one elongate member coupled to said catheter assembly at said distal end region thereof, said at least one elongate member having a free end portion situated proximate to said expandable member for releasably holding a stent situated on said expandable member during deployment, and/or for releasably grasping said stent during retrieval and/or repositioning.

14. Apparatus as recited in claim 13 wherein said stent capturing device comprise hook members situated in the region of said expandable member and structured and arranged to hold the stent during delivery, and/or grab the stent during retrieval and/or repositioning.

15. Apparatus as recited in claim 14 wherein said hook members are structured and arranged to capture the stent in a collapsed condition and to continue to capture the stent as it expands radially from said collapsed condition during deployment.

16. Apparatus for deploying, repositioning and/or retrieving a stent, comprising:

a catheter assembly having a proximal end region and a distal end region;

a thermal transfer device comprising an expandable member comprising a chamber which in its expanded condition has a circular disk shape transverse cross-section, said expandable member having an outer wall formed at least in part of heat transfer material;

means for selectively expanding and collapsing said expandable member, said means including at least one member affixed to said expandable member and said distal end region of said catheter assembly, said means being operable from said proximal end region of said catheter assembly;

thermal fluid circulating means for circulating a thermal transfer fluid from the proximal end region of said catheter assembly into said chamber of said expandable member and back to said proximal end region of said catheter assembly; and stent-capturing means situated at said distal end region of said catheter assembly for releasably capturing said stent during deployment, retrieval and/or repositioning.

17. Apparatus as recited in claim 16, comprising:

an inner core catheter and a relatively movable outer core catheter situated over said inner core catheter, said outer core catheter having a distal end which is situated proximally of the distal end of said inner core catheter, so that a projecting portion of said inner core catheter extends beyond said distal end of said outer core catheter; and wherein said mechanical means for expanding and collapsing said expandable member comprises a frame assembly comprising a plurality of wires, each wire having one end fixed to a distal end of said projecting portion of said inner core catheter, another end fixed to the distal end of said outer core catheter and a central region attached to said expandable member, whereby relative movement of said inner and outer core catheters to shorten the projecting portion of said inner core bends said wires and expands said expandable member while relative movement of said inner and outer core catheters to lengthen the projecting portion of said inner core catheter straightens said wires and collapses said balloon member.

18. Apparatus as recited in claim 16 wherein said stent-capturing means comprise a stent-capturing sheath situated over said outer core catheter and a stent-receiving sheath situated over said stent-capturing sheath; and stent-capturing hooks affixed to a distal end of said stent-capturing sheath which engage said stent-receiving sheath to move in a radial direction in response to relative movement between said stent-capturing sheath and said stent-receiving sheath.

19. Apparatus for deploying, retrieving and/or repositioning a stent, comprising:

an elongate catheter assembly having proximal and distal end regions;

a thermal transfer device operatively connected to said catheter assembly, said thermal transfer device comprising a collapsible balloon comprising a chamber which in its expanded condition comprises an outer chamber portion having an outer wall formed at least in part of heat transfer material, and an inner chamber portion in fluid communication with said outer chamber portion;

means for selectively expanding and collapsing said balloon, said means including at least one member affixed to said balloon and said distal end region of said catheter assembly, said means being operable from said proximal end region of said catheter assembly;

thermal fluid circulating means for circulating a thermal fluid from the proximal end of said catheter assembly into said outer chamber portion of said balloon and back to said proximal end region of said catheter assembly from said inner chamber portion of said balloon; and stent-capturing means situated at said distal end region of said catheter assembly for releasably capturing said stent during deployment, retrieval and/or repositioning.

20. Apparatus as recited in claim 19 wherein said catheter assembly comprises an inner core catheter and a relatively movable outer core catheter situated over said inner core catheter, said outer core catheter having a distal end which is situated proximally of the distal end of said inner core catheter, so that a projecting portion of said inner core catheter extends beyond said distal end of said outer core catheter; and wherein said mechanical means for expanding and collapsing said balloon member comprises a frame assembly comprising a plurality of wires, each wire having one end fixed to the distal end of said projecting portion of said inner core catheter, another end fixed to the distal end of said outer core catheter and a mid-region attached to said balloon member, whereby relative movement of said inner and outer core catheters to shorten the projecting portion of said inner core bends said wires and expands said balloon member while relative movement of said inner and outer core catheter to lengthen the projecting portion of said inner core catheter straightens said wires and collapses said balloon member.

21. Apparatus as recited in claim 19 wherein said stent-capturing means comprise a relatively movable stent-capturing sheath situated over said outer core catheter and a relatively moveable stent-receiving sheath situated over said stent-capturing sheath; and hook members affixed to a distal end of said stent-capturing sheath which engage said stent receiving sheath to move in a radial direction in response to relative movement between said stent-capturing sheath and said stent-receiving sheath.

22. Apparatus for deploying and/or retrieving and/or repositioning a stent having a shape memory, comprising an elongate catheter assembly having a proximal end region and a distal end region; and a thermal transfer device operatively associated with said catheter assembly, said thermal transfer device comprising an expandable member for effecting local heat transfer with a stent being deployed, retrieved and/or repositioned by said apparatus to control the temperature of the stent; and means operable from said proximal end region of said catheter assembly including at least one member affixed to said expandable member and said catheter assembly for selectively expanding and collapsing said expandable member.

23. Apparatus as recited in claim 22 further including a stent-capturing device operatively associated with said catheter assembly, said stent-capturing device comprising means for releasably holding a stent during its deployment and/or grabbing during repositioning and/or retrieving.

24. Apparatus as recited in clam 22 wherein said thermal transfer device includes a thermal transfer surface, and means for positioning said thermal transfer surface in local thermal transfer relationship with a stent during its deployment, retrieval and/or repositioning.

25. Apparatus as recited in claim 24 wherein said thermal transfer device includes a chamber defined at least in part by a thermal transfer wall having said thermal transfer surface.

* * * * *